(12) United States Patent
Driguez et al.

(10) Patent No.: US 9,012,413 B2
(45) Date of Patent: Apr. 21, 2015

(54) FGF RECEPTOR-ACTIVATING N-ACYL OCTASACCHARIDES, PREPARATION THEREOF, AND THERAPEUTIC USE THEREOF

(75) Inventors: Pierre Alexandre Driguez, Paris (FR); Philippe Duchaussoy, Paris (FR); Pierre Fons, Paris (FR); Corentin Herbert, Paris (FR); Gilbert Lassalle, Paris (FR)

(73) Assignee: Sanofi, Paris (FR)

( * ) Notice: Subject to any disclaimer, the term of this patent is extended or adjusted under 35 U.S.C. 154(b) by 564 days.

(21) Appl. No.: 13/369,675

(22) Filed: Feb. 9, 2012

(65) Prior Publication Data

US 2012/0214754 A1    Aug. 23, 2012

Related U.S. Application Data

(63) Continuation of application No. PCT/FR2010/051703, filed on Aug. 12, 2010.

(30) Foreign Application Priority Data

Aug. 14, 2009    (FR) ..................... 09 03968

(51) Int. Cl.
    A61K 31/737         (2006.01)
    A61K 31/7028        (2006.01)
    A61K 31/715         (2006.01)
    (Continued)

(52) U.S. Cl.
    CPC ............ *C08B 37/0063* (2013.01); *A61K 31/737* (2013.01); *C07H 11/00* (2013.01); *C07H 15/04* (2013.01); *C07H 15/203* (2013.01); *C08B 37/0075* (2013.01)

(58) Field of Classification Search
    USPC ........... 514/25, 54; 536/4.1, 55.1, 123.1, 122, 536/120, 121, 17.5
    See application file for complete search history.

(56) References Cited

U.S. PATENT DOCUMENTS 5,514,659 A    5/1996  Petitou et al.
6,528,497 B1   3/2003  Basten et al.
(Continued)

FOREIGN PATENT DOCUMENTS

EP    0300099    1/1989
EP    0529715    3/1993
(Continued)

OTHER PUBLICATIONS

Basten et al. (Bioorganic & Medicinal Chemistry Letters (1992), 2(9), 901-904) (abstract sent).*
Duchaussoy et al. (Bioorganic & Medicinal Chemistry Letters (1991), 1(2), 99-102) (abstract sent).*
Powers et al. (Endocrine-Related Cancer (2000) 7 165-197).*
Van Boeckel, et al., The Unique Antithrombin III Binding Domain of Heparin: A Lead to New Synthetic Antithrombotics, Angewandte Chemie, International Edition in English, vol. 32, No. 12, (1993), pp. 1671-1690.
Alavi, et al., Role of Raf in Vascular Protection from Distinct Apoptotic Stimuli, Science, vol. 301, No. 94, (2003), pp. 94-96.
Andrade, et al., Sponge-Induced Angiogenesis in Mice and the Pharmacological Reactivity of the Neovasculature Quantitated by a Fluorimetric Method, Microvascular Research, vol. 54, pp. 253-261, (1997).
Boons, Strategies in Oligosaccharide Syntheis, Tetrahedron, vol. 52, No. 4, pp. 1095-1121, (1996).
Codee, et al., The Synthesis of Well-Defined Heparin and Heparan Sulfate Fragments, Drug Discovery Today: Technologies, vol. 1, No. 3, (2004), pp. 317-326

(Continued)

*Primary Examiner* — Shaojia Anna Jiang
*Assistant Examiner* — Michael C Henry
(74) *Attorney, Agent, or Firm* — Ronald G. Ort

(57) ABSTRACT

The invention relates to FGF receptor-activating N-acyl octasaccharides having Formula (I), wherein: $R_1$ is an O-alkyl group optionally replaced by one or more aryl or cycloalkyl groups, $R_2$ is an $OSO_3^-$ or hydroxyl group, $R_3$ is an alkyl, cycloalkyl, or alkyl-cycloalkyl group, $R_4$ is a disaccharide having Formula (II), $R_6$ is a disaccharide having Formula (III), and $R_8$ is a disaccharide having Formula (IV), where $R_5$, $R_7$, and $R_9$ are $OSO_3^-$ or hydroxyl groups. The invention further relates to the preparation of said octasaccharides and to the therapeutic use thereof.

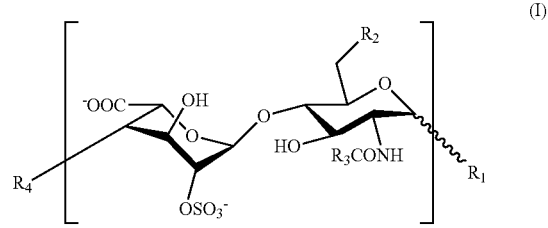

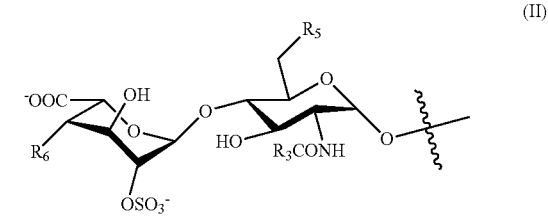

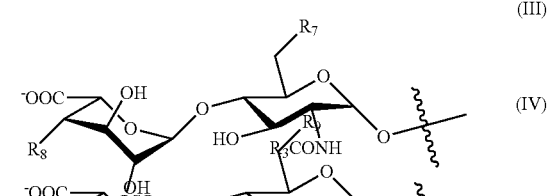

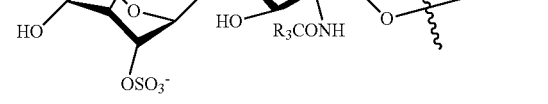

11 Claims, No Drawings

(51) Int. Cl.
| C07H 15/18 | (2006.01) |
| C07H 15/04 | (2006.01) |
| C08B 37/00 | (2006.01) |
| C07H 11/00 | (2006.01) |
| C07H 15/203 | (2006.01) |

(56) References Cited

U.S. PATENT DOCUMENTS

| 6,534,481 B1 | 3/2003 | Driguez et al. |
| 6,617,316 B1 | 9/2003 | Mourier et al. |
| 2004/0068108 A1 | 4/2004 | Duchaussoy et al. |
| 2006/0079483 A1 | 4/2006 | Hung et al. |
| 2007/0270354 A1 | 11/2007 | Petitou et al. |

FOREIGN PATENT DOCUMENTS

| EP | 0621282 | 10/1994 |
| EP | 0649854 | 4/1995 |
| FR | 2800074 | 4/2001 |
| WO | WO 92/18546 A1 | 10/1992 |
| WO | WO 98/03554 A1 | 1/1998 |
| WO | WO 99/36443 A1 | 7/1999 |
| WO | WO 2006/021653 A2 | 3/2006 |
| WO | WO 2011/018588 A3 | 2/2011 |

OTHER PUBLICATIONS

Cuevas, et al., Basic Fibroblast Growth Factor (FGF) Promotes Cartilage Repair In Vivo, Biochemical and Biophysical Research Communications, pp. 611-618, vol. 156, No. 2, (1988).
Faktorovich, et al., Basic Fibroblast Growth Factor and Local Injury Protect Photoreceptors from Light Damage in the Rat, The Journal of Neuroscience, vol. 12, No. 9, pp. 3554-3567, (1992).
Fibbi, et al., Growth Factor-Dependent Proliferation and Invasion of Muscle Satellite Cells Require the Cell-Associated Fibrinolytic System, Biol. Chem., vol. 383, pp. 127-136, (2002).
Hamacher, et al., Tumor Necrosis Factor-a and Angiostatin Are Mediators of Endothelial Cytotoxicity in Bronchoalveolar Lavages of Patients With Acute Respiratory Distress Syndrome, Am. J. Respir. Crit. Care Med., vol. 166, pp. 651-656, (2002).
Hendel, et al., Effect of Intracoronary Recombinant Human Vascular Endothelial Growth Factor on Myocardial Perfusion : Evidence for a Dose-Dependent Effect, Circulation, (2000). vol. 101, pp. 118-121.
Kato, et al., Sulfated Proteoglycan Synthesis by Confluent Cultures of Rabbit Costal Chondrocytes Grown in the Presence of Fibroblast Growth Factor, The Journal of Cell Biology, vol. 100 (1985), pp. 477-485.
Kawaguchi, et al., Acceleration of Fracture Healing in Nonhuman Primates by Fibroblast Growth Factor-2, The Journal of Clinical Endocrinology & Metabolism, vol. 86, No. 2, pp. 875-880, (2001).
Khurana, et al., Insights from Angiogenesis Trials Using Fibroblast Growth Factor For Advanced Arteriosclerotic Disease, Trends Cardiovasc. Med., vol. 13, pp. 116-122, (2003).
Klimaschewski, et al., Fibroblast Growth Factor Isoforms Promote Axonal Elongation and Branching of Adult Sensory Neurons In Vitro, Neuroscience, vol. 126, (2004), pp. 347-353.
Koshida, et al., Synthesis and Biological Activity of Oligomer-Model Compounds Containing Units of a Key Platelet-Binding Disaccharide of Heparin, Tetrahedron Letters, vol. 40, (1999), pp. 5725-5728.
Kovensky, et al., Binding of Heparan Sulfate to Fibroblast Growth Factor-2 Total Synthesis of a Putative Pentasaccharide Binding Site, Tetrahedron: Asymmetry, vol. 7, No. 11, pp. 3119-3128, (1996).
Laham, et al., Intracoronary Basic Fibroblast Growth Factor (FGF-2) in Patients With Severe Ischemic Heart Disease: Results of a Phase I Open-Label Dose Escalation Study, Journal of the American College of Cardiology, vol. 36, No. 7, (2000), pp. 2132-2139.
Laham, et al., Local Perivascular Delivery of Basic Fibroblast Growth Factor in Patients Undergoing Coronary Bypass Surgery: Results of a Phase I Randomized, Double-Blind, Placebo-Controlled Trial, Circulation, vol. 100, pp. 1865-1871, (1999).
Lahdenranta, et al., An Anti-Angiogenic State in Mice and Humans With Retinal Photoreceptor Cell Degeneration, PNAS, (2001), vol. 98, No. 18. pp. 10368-10373.
Lazarous, et al., Basic Fibroblast Growth Factor in Patients With Intermittent Claudication: Results of a Phase I Trial, Journal of the American College of Cardiology, vol. 36, No. 4, (2000). pp. 1239-1244.
Neuhaus, et al., Reduced Mobility of Fibroblast Growth Factor (FGF)-Deficient Myoblasts Might Contribute to Dystrophic Changes in the Musculature of FGF2/FGF6/Mdx Triple-Mutant Mice, Mol. Cell. Biol., (2003). vol. 23, No. 17, pp. 6037-6048.
Noti, et al., Preparation and Use of Microarrays Containing Synthetic Heparin Oligosaccharides for the Rapid Analysis of Heparin-Protein Interactions, Chem. Eur. J., (2006), vol. 12, pp. 8664-8686.
Orita, et al., Highly Efficient Deacetylation by Use of the Neutral Organotin Catalyst [tBu2SnOH(Cl)]2, Chem. Eur. J., (2001), vol. 7, No. 15, pp. 3321-3327.
Paulsen, et al., Advances in Selective Chemical Syntheses of Complex Oligosaccharides. Angewandte Chemie International Edition in English, vol. 21, No. 3, pp. 155-224, (1962).
Petitou, et al., Synthesis of Heparin Fragments: A Methyl a-Pentaoside With High Affinity for Antithrombin III, Carbohydrate Research, vol. 167, (1987), pp. 67-75.
Post, et al., Therapeutic Angiogenesis in Cardiology Using Protein Formulations, Cardiovascular Research, vol. 49, (2001), pp. 522-531.
Sakurai, et al., The Efficient Prevascularization Induced by Firboblast Growth Factor 2 With a Collagen-Coated Device Improves the Cell Survival of a Bioartificial Pancreas, Pancreas, vol. 28, No. 3, (2004), pp. e70-e79.
Sapieha, et al., Fibroblast Growth Factor-2 Gene Delivery Stimulates Axon Growth by Adult Retinal Ganglion Cells After Acute Optic Nerve Injury. Molecular and Cellular Neuroscience, vol. 24, (2003), pp. 656-672.
Sherer, et al., Angiogenesis During Implantation, and Placental and Early Embryonic Development, Placenta, (2001), vol. 22, pp. 1-13.
Simons, et al., Pharmacological Treatment of Coronary Artery Disease With Recombinant Fibroblast Growth Factor-2 Double-Blind, Randomized, Controlled Clinical Trial, Circulation, (2002), vol. 106, pp. 788-793.
Tabeur, et al., L-Iduronic Acid Derivatives as Glycosyl Donors, Carbohydrate Research, vol. 281, (1996), pp. 253-276.
Tabeur, et al., Oligosaccharides Corresponding to the Regular Sequence of Heparin: Chemical Synthesis and Interaction With FGF-2, Bioorganic & Medicinal Chemistry, vol. 7, (1999), pp. 2003-2012.
Takafuji, et al., Regeneration of Articular Cartilage Defects in the Temporomandibular Joint of Rabbits by Firbroblast Growth Factor-2: A Pilot Study, Int. J. Oral Maxillofac. Surg., (2007), vol. 36, pp. 934-937.
Unger, et al., Effects of a Single Intracoronary Injection of Basic Fibroblast Growth Factor in Stable Angina Pectoris, The American Journal of Cardiology, vol. 85, (2000), pp. 1414-1419.
Van Belle, et al., Accelerated Endothelialization by Local Delivery of Recombinant Human Vascular Endothial Growth Factor Reduces In-Stent Intimal Formation, Biochemical and Biophysical Research Communications, vol. 235, pp. 311-316, (1997).
Van Boeckel, et al., Synthesis of a Pentasaccharide Corresponding to the Antithrombin III Binding Fragment of Heparain, J. Carbohydrate Chemistry, vol. 4, No. 3, pp. 293-321, (1985).

* cited by examiner

FGF RECEPTOR-ACTIVATING N-ACYL OCTASACCHARIDES, PREPARATION THEREOF, AND THERAPEUTIC USE THEREOF

The present invention relates to N-acyl octasaccharides that are agonists of the FGF/FGFR system, and to their preparation and therapeutic use.

Angiogenesis is a process of generation of new blood capillaries. During the blockage of a blood vessel, angiogenesis, combined with arteriogenesis (dilation of the capillaries), improves the revascularization of the blocked area. It has been shown in vitro and in vivo that several growth factors, such as Fibroblast Growth Factors (FGFs), stimulate the neovascularization process.

FGFs are a family of 23 members. FGF2 (or basic FGF) is an 18 kDa protein. FGF2 induces, in endothelial cells in culture, their proliferation and migration and the production of proteases. in vivo, FGF2 promotes neovascularization. FGF2 interacts with endothelial cells via two classes of receptors, the high-affinity receptors with tyrosine kinase activity (FGFRs) and the low-affinity receptors of heparan sulfate proteoglycan (HSPG) type.

It is known that cell surface receptors with tyrosine kinase activity associate in dimeric form with a complex formed from two ligand molecules and one heparan sulfate molecule. The formation of this complex triggers a cascade of intracellular signals resulting in activation of cell proliferation and migration, which are two key processes involved in angiogenesis.

Thus, FGF2 and its receptors represent very pertinent targets for therapies directed towards activating or inhibiting angiogenesis processes.

Synthetic oligosaccharides have also been the subject of studies of interactions with the FGF receptors (C. Tabeur et al., *Bioorg. & Med. Chem.*, 1999, 7, 2003-2012; C. Noti et al., *Chem. Eur. J.*, 2006, 12, 8664-8686).

We have now found novel synthetic oligosaccharides that are capable of facilitating the formation of the FGF/FGFR complex and of thus promoting the in vitro survival of endothelial cells and of increasing the in vitro and in vivo formation of new blood vessels.

One subject of the present invention is novel octasaccharide compounds corresponding to formula (I):

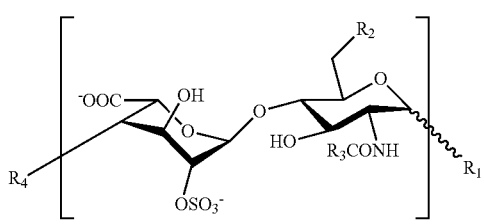

in which:
the wavy line denotes a bond located either below or above the plane of the pyranose ring of the glucosamine unit,
$R_1$ represents a group O-alkyl, in which the said alkyl group comprises from 1 to 16 carbon atoms and is optionally substituted with one or more (for example 1 or 2) groups, which may be identical or different, chosen from aryl and cycloalkyl groups,
$R_2$ represents either a group $OSO_3^-$ or a hydroxyl group,
$R_3$ represents an alkyl, cycloalkyl or alkyl-cycloalkyl group, and
$R_4$ represents a disaccharide of formula (II):

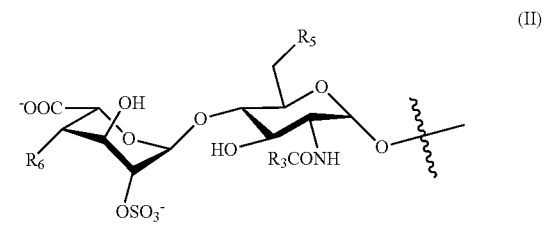

in which:
$R_3$ is as defined above,
$R_5$ represents either a group $OSO_3^-$ or a hydroxyl group, and
$R_6$ represents a disaccharide of formula (III):

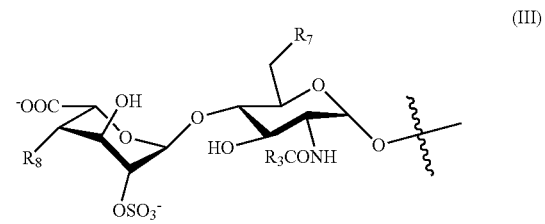

in which:
$R_3$ is as defined above,
$R_7$ represents either a group $OSO_3^-$ or a hydroxyl group, and
$R_8$ represents a disaccharide of formula (IV):

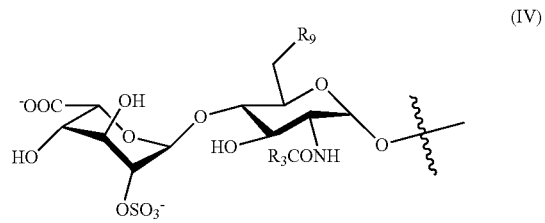

in which:
$R_3$ is as defined above,
$R_9$ represents either a group $OSO_3^-$ or a hydroxyl group.

In the context of the present invention, and unless otherwise mentioned in the text, the following definitions apply:
alkyl group: a linear or branched saturated aliphatic group. Unless otherwise indicated in the text, such an alkyl group advantageously comprises between 1 and 6 carbon atoms. Examples that may be mentioned include methyl, ethyl, propyl, isopropyl, butyl, isobutyl, tert-butyl, pentyl, etc. groups;
cycloalkyl group: a cyclic alkyl group comprising from 3 to 6 carbon atoms, for example a cyclopentyl or cyclohexyl group;
alkyl-cycloalkyl group: an alkyl group which is itself substituted with a cycloalkyl group, the said alkyl and cycloalkyl groups being as defined above; and
aryl group: a cyclic aromatic group comprising between 5 and 10 carbon atoms, such as a phenyl group. Such an aryl group is optionally substituted with one or more groups such as halogen atoms and alkyl, alkoxy, thioalkyl, trifluoromethyl and phenyl groups.

The octasaccharides according to the invention are synthetic octasaccharides, i.e. they are compounds obtained by total synthesis starting from intermediate synthons, as will be described in detail in the text hereinbelow. In this respect, they differ from oligosaccharides obtained by depolymerization or isolation from complex mixtures of polysaccharides, such as heparins or low molecular weight heparins. In particular, the compounds according to the invention have a well-defined structure resulting from their chemical synthesis and are in the form of pure octasaccharides, i.e. they are free of other octasaccharide species.

The invention encompasses the compounds of formula (I) in acid form or in the form of any pharmaceutically acceptable salt thereof. In the acid form, the functions —COO$^-$ and —SO$_3^-$ are, respectively, in —COOH and —SO$_3$H form.

The term "pharmaceutically acceptable salt of the compounds of the invention" means a compound in which one or more of the functions —COO$^-$ and/or —SO$_3^-$ are ionically linked to a pharmaceutically acceptable cation. The preferred salts according to the invention are those in which the cation is chosen from alkali metal cations, especially the Na$^+$ cation.

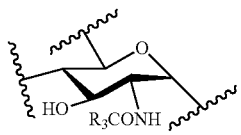

The other type of saccharide unit present in the compounds according to the invention is a uronic acid, more specifically an iduronic acid, corresponding to the following formula:

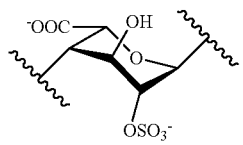

Thus, the compounds of formula (I) according to the invention, which are octasaccharides, may also be represented according to formula (I') as follows, in which the iduronic units and the glucosamine units succeed each other and in which $R_1$, $R_2$, $R_3$, $R_5$, $R_7$ and $R_9$ are as defined previously:

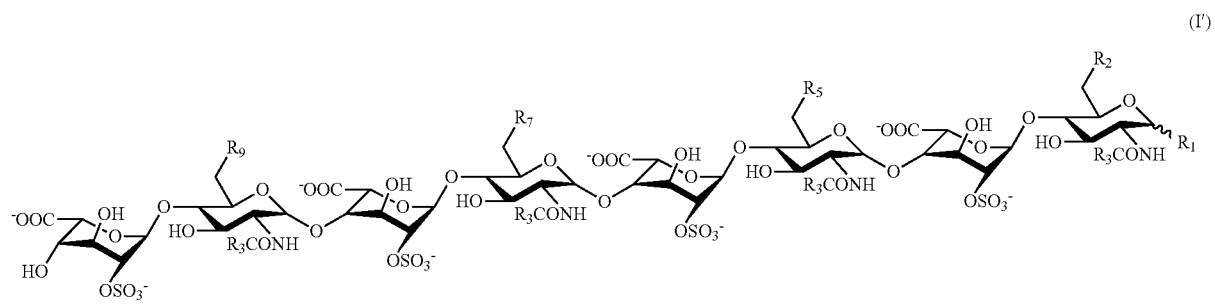

(I')

The compounds of formula (I) according to the invention also comprise those in which one or more hydrogen or carbon atoms have been replaced with a radioactive isotope, for example tritium or carbon $^{14}$C. Such labelled compounds are useful in research, metabolism or pharmacokinetic studies, as ligands in biochemical tests.

In formula (I) of the compounds according to the present invention, it is understood that:
- the disaccharide of formula (II) is linked to the disaccharide unit represented in formula (I) via the oxygen atom located in position 1 of its glucosamine unit,
- similarly, the disaccharide of formula (III) is linked to the disaccharide of formula (II) via the oxygen atom located in position 1 of its glucosamine unit,
- similarly, the disaccharide of formula (IV) is linked to the disaccharide of formula (III) via the oxygen atom located in position 1 of its glucosamine unit.

The term "glucosamine unit" means the monosaccharide unit having the following formula:

Among the compounds of formula (I)/(I') that are subjects of the invention, mention may be made of a subgroup of compounds in which $R_1$ represents:
- either a group O-alkyl, in which the said alkyl group comprises from 5 to 16 carbon atoms and advantageously from 5 to 12 carbon atoms (for example a group —O-pentyl, —O-undecyl or 2-propylpentyl),
- or a group O-alkyl, in which the said alkyl group comprises from 1 to 8 carbon atoms and advantageously from 3 to 6 carbon atoms (for example a group —O-propyl or —O-pentyl), and is substituted with 1 or 2 groups, which may be identical or different, chosen from aryl and cycloalkyl groups (for example phenyl and cycloalkyl groups, such as cyclohexyl).

Among the compounds of formula (I)/(I') that are subjects of the invention, mention may be made of another subgroup of compounds, in which $R_3$ represents either an alkyl group comprising from 2 to 6 carbon atoms (for example a propyl or pentyl group) or a cycloalkyl group (for example a cyclopentyl group).

Among the compounds of formula (I)/(I') that are subjects of the invention, mention may be made of another subgroup of compounds, in which at least one of the groups $R_2$, $R_5$, $R_7$ and $R_9$ represents a hydroxyl group.

Another subgroup of compounds that are subjects of the invention is such that at least one of the groups $R_2$, $R_5$, $R_7$ and $R_9$ represents a hydroxyl group and at least one of the groups $R_2$, $R_5$, $R_7$ and $R_9$ represents a group $OSO_3^-$.

Other subgroups of octasaccharides according to the invention may have several of the characteristics listed above for each of the subgroups defined previously.

Mention may be made in particular of the subgroup of compounds of formula (I) in which:

$R_1$ represents:
  either a group O-alkyl, in which the said alkyl group comprises from 5 to 16 carbon atoms and advantageously from 5 to 12 carbon atoms (for example a group —O-pentyl, —O-undecyl or 2-propylpentyl),
  or a group O-alkyl, in which the said alkyl group comprises from 1 to 8 carbon atoms and advantageously from 3 to 6 carbon atoms (for example a group —O-propyl or —O-pentyl), and is substituted with 1 or 2 groups, which may be identical or different, chosen from aryl and cycloalkyl groups (for example phenyl and cycloalkyl groups, such as cyclohexyl), $R_3$ represents either an alkyl group comprising from 2 to 6 carbon atoms (for example a propyl or pantyl group) or a cycloalkyl group (for example a cyclopentyl group), and at least one of the groups $R_2$, $R_5$, $R_7$ and $R_9$ represents a hydroxyl group.

Among the compounds of the invention, mention may be made especially of the following octasaccharides:

Pentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyl-uronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 1);

Pentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-2-deoxy-2-(1-oxobutyl)amino-6-O-sodium sulfonato-β-D-glucopyranoside (No. 2);

Pentyl (sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-2-deoxy-2-(1-oxohexyl)amino-6-O-sodium sulfonato-β-D-glucopyranoside (No. 3);

Pentyl (sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-2-[(cyclopentylcarbonyl)amino]-2-deoxy-6-O-sodium sulfonato-β-D-glucopyranoside (No. 4);

Undecyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 5);

5-phenylpentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 6);

Methyl (sodium 2-O-sodium sulfonato-α-L-idopyranosyluronate)-(1→4)-(2-acetamido-2-deoxy-6-O-sodium sulfonato-α-D-glucopyranosyl)-[(1→4)-(sodium 2-O-sodium sulfonato-α-L-idopyranosyluronate)-(1→4)-(2-acetamido-2-deoxy-6-O-sodium sulfonato-α-D-glucopyranosyl)]$_2$-(1→4)-(sodium 2-O-sodium sulfonato-α-L-idopyranosyluronate)-(1→4)-2-acetamido-2-deoxy-6-O-sodium sulfonato-α-D-glucopyranoside (No. 7);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 8);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O- sodium sulfonato-α-L-idopyranosyluronate)-(1→4)-2-acetamido-2-deoxy-6-O-sodium sulfonato-α-D-glucopyranoside (No. 9);

Methyl (sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (No. 10);

Methyl (sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 11);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (No. 12);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 13);

5-phenylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 14);

2-propylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 15);

3-cyclohexylpropyl (sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-α-D-glucopyranosyl)-(1→4)-(sodium 2-O-sodium sulfonato-α-L-idopyranosyluronate)-(1→4)-2-deoxy-2-acetamido-β-D-glucopyranoside (No. 16);

3-cyclohexylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 17);

3,3-diphenylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyl uronate)-(1→4)-2-deoxy-2-(1-oxobutyl)amino-β-D-glucopyranoside (No. 18); and 5-phenylpentyl (sodium 2-O-sodium sulfonato-α-L-idopyranosyluronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(3-methyl-1-oxobutyl)amino-α-D-glucopyranosyl)-(1→4)-(sodium 2-O-sodium sulfonato-α-L-idopyranosyluronate)-(1→4)-2-deoxy-2-(3-methyl-1-oxobutyl)amino-β-D-glucopyranoside (No. 19).

In its principle, the process for preparing the compounds according to the invention uses di- or oligosaccharide synthons prepared as reported previously in the literature. Reference will be made especially to the patents or patent applications EP 0 300 099, EP 0 529 715, EP 0 621 282 and EP 0 649 854, and also to the publication by C. Van Boeckel and M. Petitou published in *Angew. Chem. Int. Ed. Engl.*, 1993, 32, 1671-1690. These synthons are then coupled together so as to give an entirely protected equivalent of an octasaccharide according to the invention. This protected equivalent is then converted into a compound according to the invention. In the coupling reactions mentioned above, a "donor" di- or oligosaccharide, activated on its anomeric carbon, reacts with an "acceptor" di- or oligosaccharide, bearing a free hydroxyl.

The specific synthetic schemes will be described in the detailed examples that follow.

The present invention thus relates to a process for preparing octasaccharides of formula (I)/(I'), characterized in that:
in a first phase, a fully protected equivalent of the desired octasaccharide (I) is synthesized,
in a second phase, the positions that are to bear sulfonate groups on the final molecule are deprotected and then O-sulfated,
in a third phase, the whole compound is deprotected, and
in a fourth phase, the N-acyl groups are introduced (introduction of groups the $R_3$—CO—).

The synthesis of the fully protected equivalent of the desired octasaccharide (I) is performed according to reactions that are well known to those skilled in the art, and using methods for the synthesis of oligosaccharides (for example G. J. Boons, *Tetrahedron* (1996), 52, 1095-1121 and patent applications WO 98/03554 and WO 99/36443), in which a glycoside bond-donating oligosaccharide is coupled with a glycoside bond-accepting oligosaccharide to give another oligosaccharide whose size is equal to the sum of the sizes of the two reactive species. This sequence is repeated until the compound of formula (I) is obtained, optionally in protected form. The nature and profile of the charge of the final desired compound determine the nature of the chemical species used in the various synthetic steps, according to the rules well known to those skilled in the art. Reference may be made, for example, to C. Van Boeckel and M. Petitou, *Angew. Chem. Int. Ed. Engl.* (1993), 32, 1671-1690 or alternatively to H. Paulsen, "Advances in selective chemical syntheses of complex oligosaccharides", *Angew. Chem. Int. Ed. Engl.* (1982), 21, 155-173.

The compounds of the invention may naturally be prepared using various strategies known to those skilled in the art of oligosaccharide synthesis. The process described above is the preferred process of the invention. However, the compounds of formula (I)/(I') may be prepared via other well-known methods of sugar chemistry, described, for example, in "Monosaccharides, their chemistry and their roles in natural products", P. M. Collins and R. J. Ferrier, J. Wiley & Sons (1995) and by G. J. Boons in *Tetrahedron* (1996), 52, 1095-1121.

The protecting groups used in the process for preparing the compounds of formula (I)/(I') are those that make it possible firstly to protect a reactive function such as a hydroxyl or an amine during a synthesis, and secondly to regenerate the intact reactive function at the end of the synthesis. The protecting groups commonly used in sugar chemistry, as described, for example, in "Protective Groups in Organic Synthesis", Greene et al., 3rd edition (John Wiley & Sons, Inc., New York) are used to perform the process according to the invention. The protecting groups are chosen, for example, from acetyl, methyl, pentenyl, benzoyl, levulinyl, benzyl, substituted benzyl, azide, benzyl carbamate, tert-butyldimethylsilyl (tBDMS) and tert-butyldiphenylsilyl (tBDPS) groups.

Activating groups may also be used; these are the groups conventionally used in sugar chemistry, for example according to G. J. Boons, *Tetrahedron* (1996), 52, 1095-1121. These activating groups are chosen, for example, from imidates and thioglycosides.

The process described above allows the compounds of the invention to be obtained in the form of salts, advantageously in the form of the sodium salt. To obtain the corresponding acids, the compounds of the invention in salt form may be placed in contact with a cation-exchange resin in acidic form. The compounds of the invention in acid form may then be neutralized with a base to obtain the desired salt. For the preparation of the salts of the compounds of formula (I)/(I'), any mineral or organic base that gives pharmaceutically acceptable salts with the compounds of formula (I)/(I') may be used.

A subject of the invention is also the compounds of formula (V) below, in which Alk represents an alkyl group, $R_1$ is as defined previously in relation with the compounds of formula (I)/(I'), and Pg, Pg' and Pg", which may be identical or different, represent protecting groups:

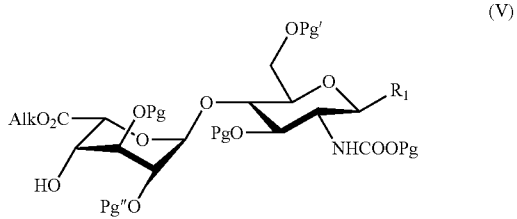

(V)

Such compounds are useful as intermediates in the synthesis of the compounds of formula (I)/(I').

In particular, a subject of the invention is the compounds (V) in which Alk represents a methyl group and Pg, Pg' and Pg" represent, respectively, benzyl, tBDPS and acetyl groups. More particularly, among these compounds of formula (V), the invention is directed towards those in which $R_1$ is chosen from the following groups: —O-methyl, —O—$(CH_2)_5$-phenyl, —O—$CH_2$—$CH(C_3H_7)_2$, —O—$(CH_2)_3$—$C_6H_{11}$ and —O—$(CH_2)_2$—$CH(phenyl)_2$.

Such compounds correspond to disaccharides 58, 131, 132, 133 and 134 illustrated in the synthetic schemes below, which are useful for the synthesis of compounds 10, 11 and 14 to 19 according to the invention, as will be detailed hereinbelow.

A subject of the invention is also the compounds of formula (VI) below, in which Alk represents an alkyl group and Pg, Pg' and Pg", which may be identical or different, represent protecting groups:

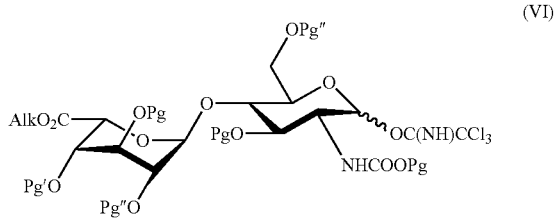

(VI)

Such compounds are useful as intermediates in the synthesis of the compounds of formula (I)/(I').

In particular, a subject of the invention is compound (VI) in which Alk represents a methyl group and Pg, Pg' and Pg" represent, respectively, benzyl, levulinyl and acetyl groups. Such a compound corresponds to disaccharide 24 illustrated in the synthetic schemes below, which is useful for the synthesis of compounds 1 to 4 according to the invention, as will be detailed hereinbelow.

The examples that follow describe the preparation of certain compounds in accordance with the invention. These compounds are not limiting, but serve merely to illustrate the present invention. The starting compounds and the reagents, when their mode of preparation is not expressly described, are commercially available or described in the literature, or else may be prepared according to methods that are described therein or that are known to those skilled in the art.

The following abbreviations are used:

[α]$_D$: optical rotation
Ac: acetyl
Bn: benzyl
TLC: thin-layer chromatography
DDQ: 2,3-dichloro-5,6-dicyano-1,4-benzoquinone
ESI: Electron-Spray Ionization
h: hours
LC-MS (*): liquid chromatography coupled to mass spectrometry
Lev: levulinyl
min: minutes
Me: methyl
PMB: para-methoxybenzyl Rf: Retardation factor (retention time measured on TLC relative to the solvent migration front)
tBDMS: tert-butyldimethylsilyl
tBDPS: tert-butyldiphenylsilyl
TFA: trifluoroacetic acid
T$_R$: retention time measured by LC-MS*
Z: benzyloxycarbonyl

*The LC-MS are acquired on a Waters brand ZQ4000 machine. The column used is a Symmetry C18 3.5 μm (2.1× 50 mm). Eluent A is formed from H$_2$O+0.005% TFA, pH 3.15. Eluent B is formed from acetonitrile+0.005% TFA. The gradient ranges from 0 to 90% of eluent B over 10 (or 30) minutes+5 minutes at 90% of eluent B. The flow rate is 0.4 mL/min.

Preparation of the Synthetic Intermediates

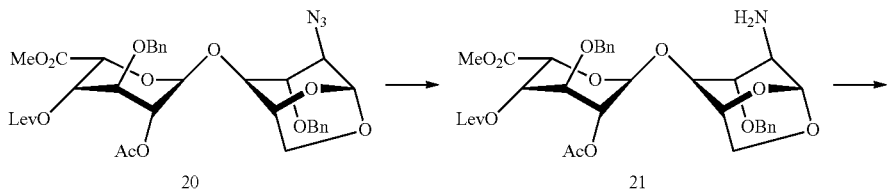

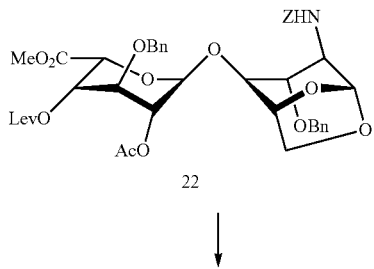

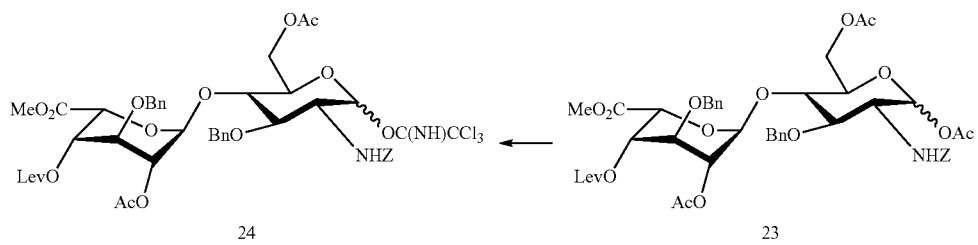

Preparation of (methyl 2-O-acetyl-3-O-benzyl-4-O-levulinoyl-α-L-idopyranosyl-uronate)-(1→4)-2-amino-1,6-anhydro-3-O-benzyl-2-deoxy-β-D-glucopyranose (No. 21)

To a solution of compound 20 (21.6 g, 31 mmol) (C. A. A. Van Boeckel et al., J. Carbohydr. Chem., 4 (1985) 293-321) in N,N-dimethylformamide (155 mL) is added triethylamine (Et$_3$N) (65 mL, 15 molar equivalents), followed by addition of 1,3-propanedithiol (47 mL, 15 molar equivalents). After 17 hours of magnetic stirring, the reaction mixture is diluted with ethyl acetate, washed with water, dried (Na$_2$SO$_4$), filtered and concentrated, and then purified on silica gel (acetone-cyclohexane) to give 21 (15.8 g, 76%).

LC-MS m/z 672.2 [(M+H)$^+$]. T$_R$=0.94 min

Preparation of (methyl 2-O-acetyl-3-O-benzyl-4-O-levulinoyl-α-L-idopyranosyluronate)-(1→4)-1,6-anhydro-3-O-benzyl-2-deoxy-2-[(benzyloxy)carbonyl]amino-β-D-glucopyranose (No. 22)

To a solution of compound 21 (128.12 g, 190.7 mmol) in dichloromethane (240 mL) is added saturated aqueous sodium hydrogen carbonate solution (240 mL), followed by addition, at 0° C., of benzyloxycarbonyl chloride (35.5 mL, 1.3 molar equivalents). After 15 minutes of vigorous magnetic stirring at 0° C., the reaction mixture is diluted with dichloromethane, washed with water to neutrality, dried (Na$_2$SO$_4$), filtered and concentrated. The crude product is used in the following step without purification.

LC-MS m/z 806.2 [(M+H)$^+$]. T$_R$=1.55 min

Preparation of (methyl 2-O-acetyl-3-O-benzyl-4-O-levulinoyl-α-L-idopyranosyluronate)-(1→4)-1,6-di-O-acetyl-3-O-benzyl-2-deoxy-2-[(benzyloxy)carbonyl]amino-α,β-D-glucopyranose (No. 23)

The residue obtained in the preceding step is dissolved in acetic anhydride (1.05 L), followed by addition, at 0° C. and over 15 min, of trifluoroacetic acid (TFA) (105 mL). The reaction mixture is stirred for 10 minutes at 0° C. and for 18 hours at room temperature, and is then concentrated, co-evaporated with toluene, and purified on silica gel (cyclohexane-acetone), to give compound 23 (138.9 g, 80%, 2 steps).

LC-MS m/z 930.3 [(M+Na)$^+$]. T$_R$=21.68/21.84 min

Preparation of (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)carbonyl]amino-α,β-D-glucopyranose trichloroacetimidate (No. 24)

To a solution of compound 23 (25 g, 27.5 mmol) in diethyl ether (1.1 L) is added, at 0° C., benzylamine (BnNH$_2$) (109 mL, 36 molar equivalents). After stirring for 1 hour at 0° C., and then for 4.5 hours at room temperature, the reaction mixture is diluted with ethyl acetate, and then neutralized with cold 1N HCl (0-4° C.), washed with water, dried (Na$_2$SO$_4$), filtered and concentrated, and purified on silica gel (acetone-cyclohexane) to give (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)carbonyl]amino-α,β-D-glucopyranose (18.5 g, 78%).

LC-MS m/z 888.3 [(M+Na)$^+$]. T$_R$=19.95/20.60 min

To a solution of the compound thus obtained (18.5 g, 21.4 mmol) in dichloromethane (405 mL) is added, under argon and at 0° C., cesium carbonate (Cs$_2$CO$_3$) (11.1 g, 1.6 molar equivalents) and trichloroacetonitrile (CCl$_3$CN) (14.8 mL, 5.0 molar equivalents). After stirring for 1 hour at room temperature, the reaction mixture is filtered and then concentrated. The residue is purified on silica gel (acetone-yclohexane+0.1% triethylamine) to give 24 (17.2 g, 80%).

Rf=0.47 (7/3 ethyl acetate/cyclohexane).

Chemical shifts of anomeric protons (500 MHz, CDCl$_3$) δ 5.17 IdoUA$^H$, 6.28 Glc$^I$α

LC-MS m/z 866.3 [(M+Na)$^+$]. T$_{R1}$=19.91 min

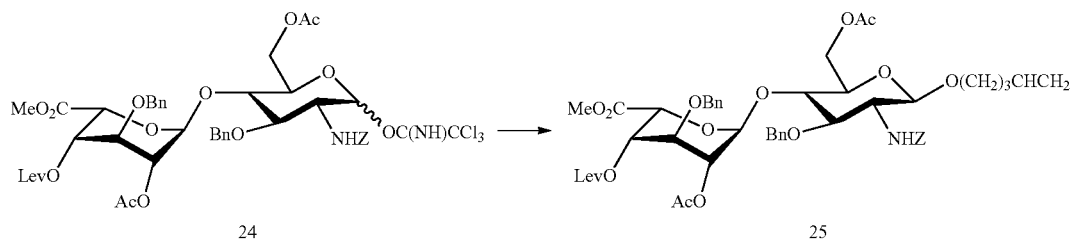

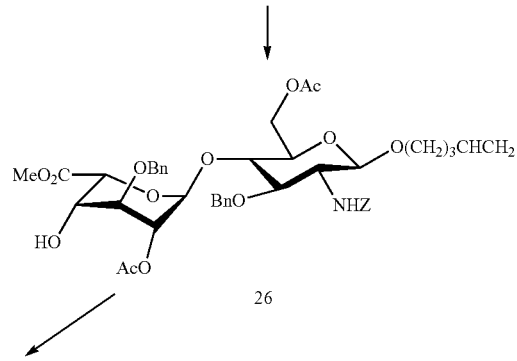

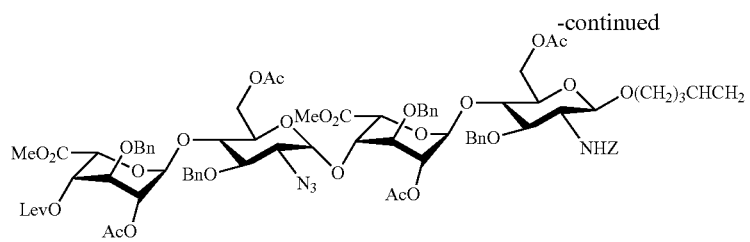
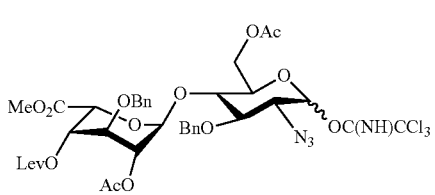
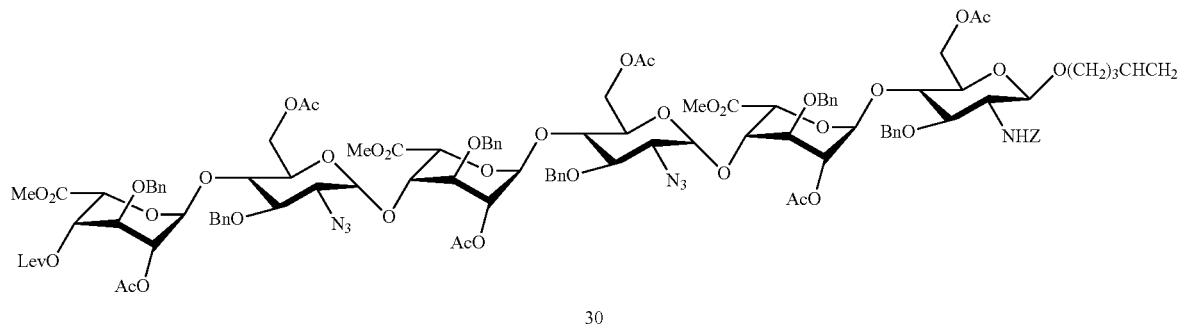
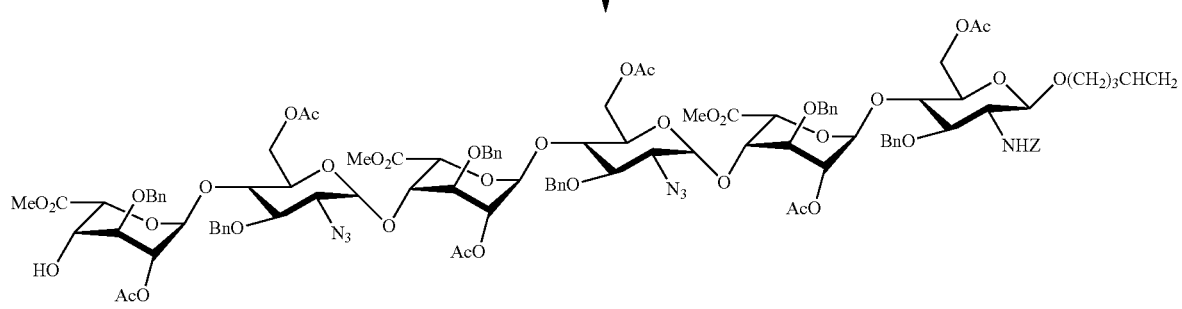

Preparation of 4-pentenyl (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)carbonyl]-amino-β-D-glucopyranoside (No. 25)

A solution of tert-butyldimethylsilyl triflate in dichloromethane (1M, 0.2 mol per mole of imidate) is added, under argon and at −20° C., to a solution of the imidate 24 (13.7 g, 13.56 mmol) and of allyl alcohol (6.8 mL, 5 molar equivalents) in dichloromethane (590 mL) in the presence of 4 Å molecular sieves (17.6 g). After 20 minutes of stirring (TLC), saturated aqueous sodium hydrogen carbonate solution is added. After filtering, washing with water, drying ($Na_2SO_4$), filtering and evaporating to dryness, the mixture is purified on silica gel to give compound 25 (10.7 g, 85%).

LC-MS m/z 934.5 [(M+H)$^+$]. $T_R$=24.00 min

Preparation of 4-pentenyl (methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 26)

To a solution of compound 25 (10.6 g, 11.35 mmol) in a 1:2 mixture of toluene/ethanol (1.2 L) is added hydrazine acetate (5.2 g, 5 molar equivalents). After 2.5 hours of magnetic stirring, the mixture is concentrated under vacuum and then purified on silica gel to give compound 26 (6.98 g, 74%).

LC-MS m/z 858.4 [(M+Na)$^+$]. $T_R$=22.62 min

Preparation of 4-pentenyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 28)

A solution of tert-butyldimethylsilyl triflate in dichloromethane (1M, 0.15 mol per mole of imidate) is added, under argon and at −20° C., to a solution of the imidate 27 (9.0 g, 9.98 mmol) (C. Tabeur et al., BioOrg. Med. Chem. (1999) 7, 2003-2012) and of the glycosyl acceptor 26 (6.95 g, 8.32 mmol) in dichloromethane (350 mL) in the presence of 4 Å molecular sieves (7.5 g). After 18 hours at −20° C. (TLC), solid sodium hydrogen carbonate is added. After filtering, washing with aqueous 2% sodium hydrogen carbonate solution, with water, drying ($Na_2SO_4$), filtering and evaporating to dryness, the residue is purified on silica gel to give 28 (9.04 g, 69%).

Rf=0.38 (1/4 acetone/toluene).

Preparation of 4-pentenyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 29)

To a solution of compound 28 (9.0 g, 5.7 mmol) in a 1:2 mixture of toluene/ethanol (570 mL) is added hydrazine acetate (2.6 g, 5 molar equivalents). After 1 hour of magnetic stirring, the mixture is concentrated under vacuum and then purified on silica gel to give compound 29 (7.15 g, 85%).

Rf=0.29 (1/4 acetone/toluene).

Preparation of 4-pentenyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 30)

A solution of tert-butyldimethylsilyl triflate in dichloromethane (1M, 0.15 mol per mole of imidate) is added, under argon and at −20° C., to a solution of the imidate 27 (4.80 g, 5.32 mmol) and of the glycosyl acceptor 29 (7.15 g, 4.84 mmol) in dichloromethane (180 mL) in the presence of 4 Å molecular sieves (3.99 g). After 18 hours at −20° C. (TLC), solid sodium hydrogen carbonate is added. After magnetic stirring at room temperature (30 minutes), filtering, washing with aqueous 2% sodium hydrogen carbonate solution, and then with water, drying ($Na_2SO_4$) and evaporating to dryness, the residue is purified on silica gel to give 30 (5.23 g, 49%).

Rf=0.18 (1/4 acetone/diisopropyl ether).

Preparation of 4-pentenyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]-amino-β-D-glucopyranoside (No. 31)

To a solution of compound 30 (5.21 g, 2.35 mmol) in a 1:2 mixture of toluene/ethanol (180 mL) is added hydrazine acetate (1.08 g, 5 molar equivalents). After 1 hour 10 minutes of magnetic stirring, the mixture is concentrated under vacuum and then purified on silica gel to give compound 31 (4.78 g, 96%).

Rf=0.47 (1/3 acetone/diisopropyl ether).

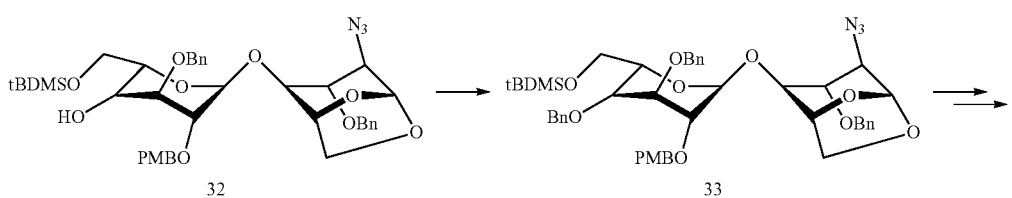

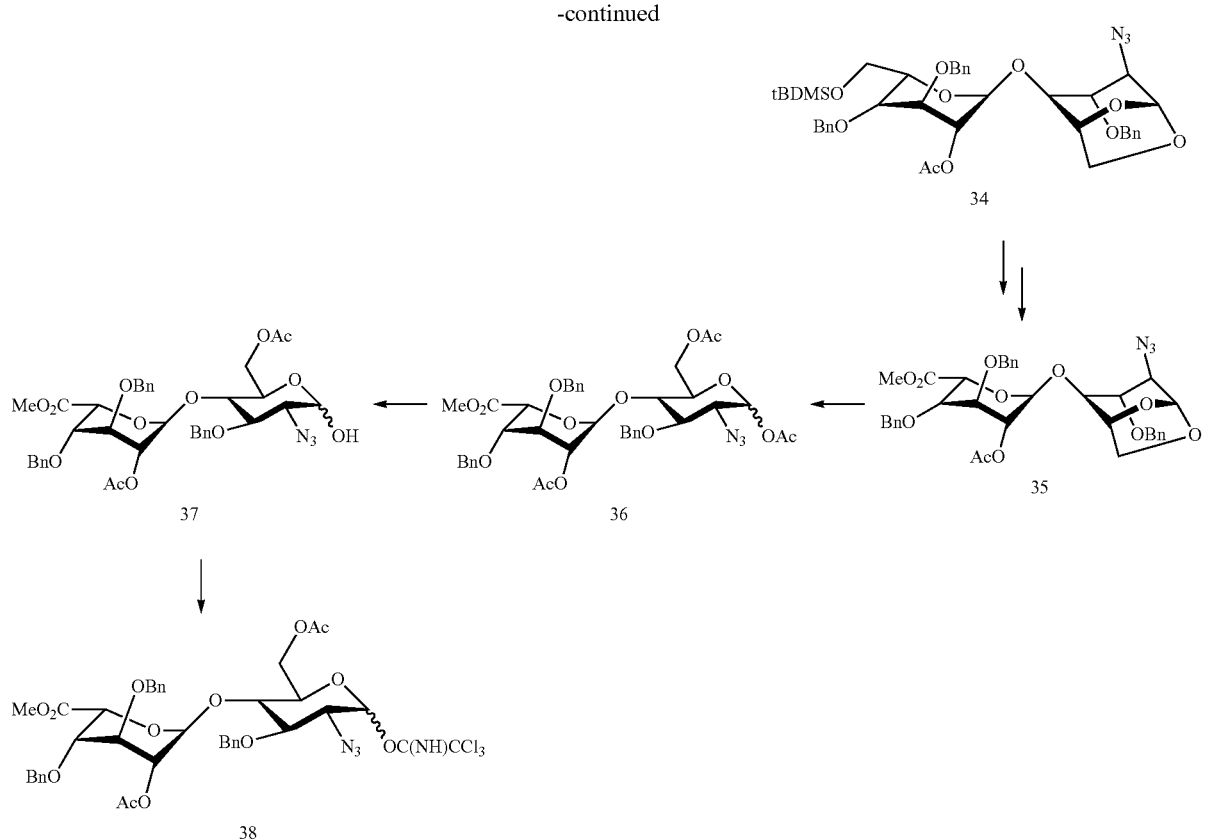

Preparation of (3,4-di-O-benzyl-2-O-(4-methoxy) benzyl-6-O-tert-butyldimethylsilyl-α-L-idopyranosyl)-(1→4)-1,6-anhydro-2-azido-3-O-benzyl-2-deoxy-β-D-glucopyranose (No. 33)

To a solution of compound 32 (32.3 g, 42.2 mmol) (WO 2006/021 653) in N,N-dimethylformamide (210 mL) is added, at 0° C. and under argon, benzyl bromide (25 mL, 5 molar equivalents), followed by addition of 55% NaH (3 g, 1.5 molar equivalents). After 20 minutes of magnetic stirring, methanol is added (30 mL), the reaction medium is concentrated under vacuum, and the crude reaction product is diluted with ethyl acetate, washed with water and then with saturated aqueous sodium chloride solution, dried ($Na_2SO_4$), filtered and concentrated. The residue obtained is used in the following step without purification.

LC-MS m/z 871.7 [(M+NH$_4$)$^+$]. T$_R$=13.86 min

Preparation of (2-O-acetyl-3,4-di-O-benzyl-6-O-tert-butyldimethylsilyl-α-L-idopyranosyl)-(1→4)-1,6-anhydro-2-azido-3-O-benzyl-2-deoxy-β-D-glucopyranose (No. 34)

To a solution of crude 33 (38.6 g) in dichloromethane (1.6 L) is added water (80 mL), followed by addition, at 0° C., of DDQ (14.2 g, 1.5 molar equivalents). After 4 hours 45 minutes of stirring at 0° C., the medium is diluted with dichloromethane and sodium hydrogen carbonate solution is added. The organic phase is then washed with water, dried ($Na_2SO_4$), filtered and concentrated. The compound obtained is used in the following step without purification.

The residue obtained is dissolved in dichloromethane (350 mL), followed by addition of triethylamine (13 mL), 4-dimethylaminopyridine (2 g) and acetic anhydride (60 mL). After magnetic stirring for 10 minutes at 0° C. and then for 1 hour 45 minutes at room temperature, the reaction mixture is diluted with dichloromethane and then washed successively with aqueous 10% potassium hydrogen sulfate solution and water, and the organic phase is then dried ($Na_2SO_4$), filtered and concentrated.

The residue obtained is purified on silica (ethyl acetate-cyclohexane) to give 34 (26.8 g, 83%, 3 steps).

LC-MS m/z 798.3 [(M+Na)$^+$]. T$_R$=12.97 min

Preparation of (methyl 2-O-acetyl-3,4-di-O-benzyl-α-L-idopyranosyluronate)-(1→4)-1,6-anhydro-2-azido-3-O-benzyl-2-deoxy-β-D-glucopyranose (No. 35)

To a solution of 34 (26.3 g, 33.9 mmol) in acetone (1.4 L) is added, at 0° C., a solution of $CrO_3$ (10.5 g, 3.1 molar equivalents) in aqueous 3.5 M $H_2SO_4$ (47 mL). After mechanical stirring for 4 hours at 0° C., the reaction medium is diluted with dichloromethane, washed with water to neutrality, and the organic phase is then dried ($Na_2SO_4$), filtered and concentrated. The compound obtained is used in the following step without purification.

The residue obtained is dissolved in N,N-dimethylformamide (210 mL), and potassium hydrogen carbonate (17 g, 5 molar equivalents) and methyl iodide (21 mL, 10 molar equivalents) are added. The reaction mixture is stirred at room temperature for 16 hours, and then concentrated under vacuum. The residue is diluted with ethyl acetate and then washed with water, with saturated aqueous sodium thiosulfate solution, with saturated aqueous sodium chloride solution, and then dried (Na$_2$SO$_4$), filtered and concentrated. The compound obtained is used in the following step without purification.

LC-MS m/z 707.3 [(M+NH$_4$)$^+$]. T$_R$=10.37 min

Preparation of (methyl 2-O-acetyl-3,4-di-O-benzyl-α-L-idopyranosyluronate)-(1→4)-1,6-di-O-acetyl-2-azido-3-O-benzyl-2-deoxy-α,β-D-glucopyranose (No. 36)

The crude residue obtained in the preceding step is dissolved in acetic anhydride (177 mL), followed by addition of trifluoroacetic acid (TFA) (17.7 mL). The reaction mixture is stirred for 16 hours, and is then concentrated, co-evaporated with toluene, and purified on silica gel (cyclohexane-ethyl acetate), to give compound 36 (17.4 g, 65%, 3 steps).

LC-MS m/z 809.3 [(M+NH$_4$)$^+$]. T$_R$=10.81 min

Preparation of (methyl 2-O-acetyl-3,4-di-O-benzyl-α-L-idopyranosyluronate)-(1→4)-6-O-acetyl-2-azido-3-O-benzyl-2-deoxy-α,β-D-glucopyranose (No. 37)

To a solution of compound 36 (7 g, 8.84 mmol) in diethyl ether (303 mL) is added, at 0° C. and under argon, benzylamine (BnNH$_2$) (29.7 mL, 36 molar equivalents). After 1 hour of magnetic stirring at 0° C. and then 6 hours at room temperature, the reaction mixture is neutralized with cold (0-4° C.) 1N HCl, washed with water, dried (Na$_2$SO$_4$), filtered and concentrated, and purified on silica gel (ethyl acetate-cyclohexane) to give 37 (5.95 g, 90%).

LC-MS m/z 767.7 [(M+NH$_4$)$^+$]. T$_R$=1.64 min

Preparation of (methyl 2-O-acetyl-3,4-di-O-benzyl-α-L-idopyranosyluronate)-(1→4)-6-O-acetyl-2-azido-3-O-benzyl-2-deoxy-α,β-D-glucopyranose trichloroacetimidate (No. 38)

To a solution of compound 37 (5.94 g, 7.9 mmol) in dichloromethane (150 mL) is added, under argon, cesium carbonate (Cs$_2$CO$_3$) (4.1 g, 1.6 molar equivalents), followed by addition of trichloroacetonitrile (CCl$_3$CN) (3.9 mL, 5.0 molar equivalents). After stirring for 45 minutes at room temperature, the reaction mixture is filtered and then concentrated. The residue is purified on silica gel (ethyl acetate-cyclohexane+0.1% triethylamine) to give 38 (5.7 g, 81%).

LC-MS m/z 912.0 [(M+NH$_4$)$^+$]. T$_R$=1.81 min

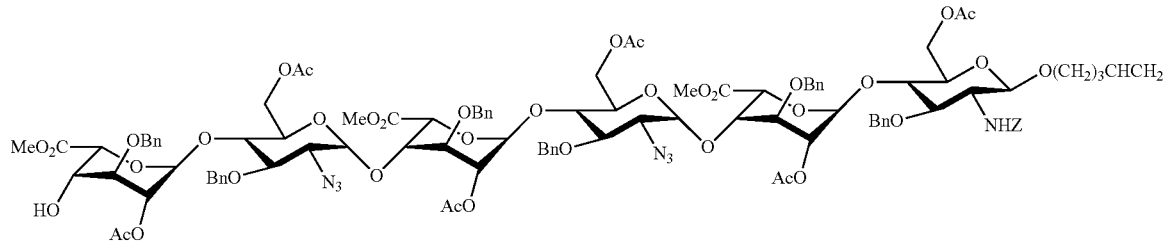

31

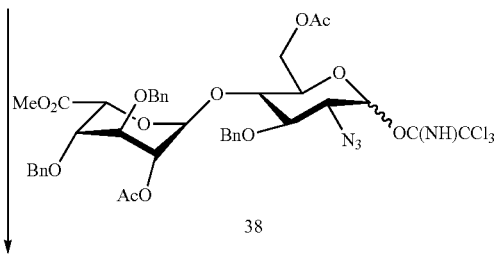

38

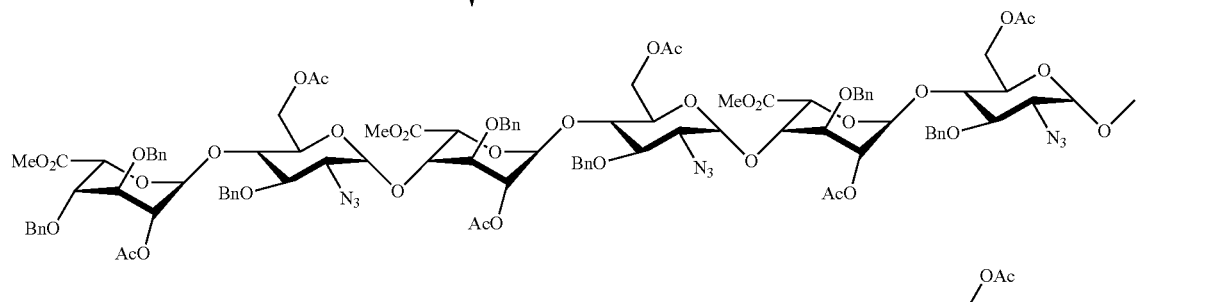

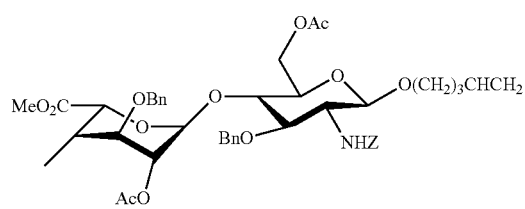

39

Preparation of 4-pentenyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 39)

A solution of tert-butyldimethylsilyl triflate in dichloromethane (1M, 0.1 mol per mole of imidate) is added, under argon and at −15° C., to a solution of the imidate 38 (2.61 g, 2.92 mmol) and of the glycosyl acceptor 31 (4.78 g, 2.25 mmol) in dichloromethane (146 mL) in the presence of 4 Å molecular sieves (1.99 g). After 2 hours of magnetic stirring at −15° C. (TLC), imidate 38 is again added at time intervals of between 15 and 30 minutes, to maximum consumption of the acceptor 31. At the end of the reaction (TLC), solid sodium hydrogen carbonate is added to neutralize, and after magnetic stirring at room temperature (15 minutes), filtering, washing with aqueous 2% sodium hydrogen carbonate solution, and then with water, drying ($Na_2SO_4$) and evaporating to dryness, the residue is purified on silica gel to give 39 (3.71 g, 58%).

Rf=0.21 (15/85 acetone/toluene).

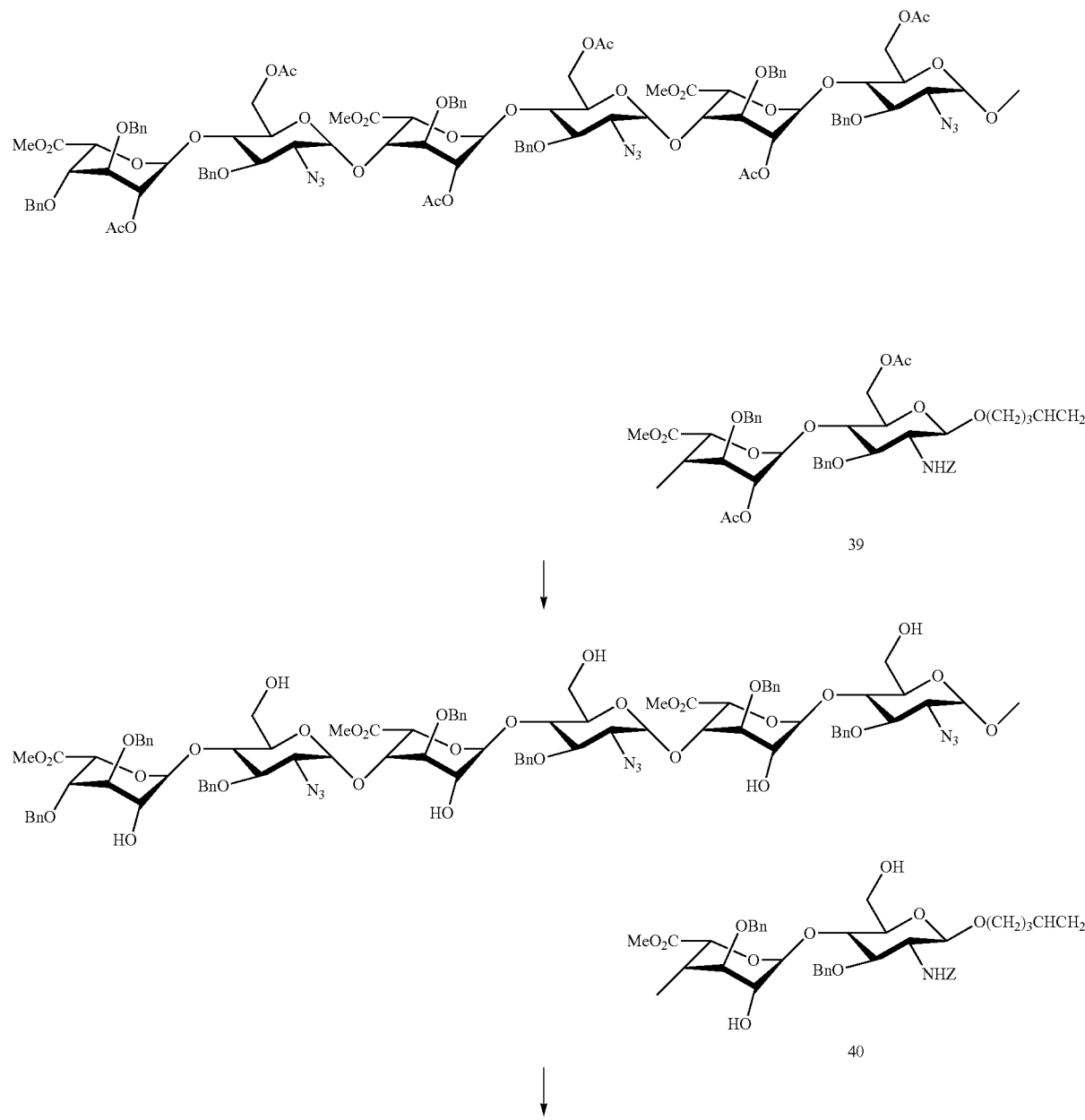

-continued
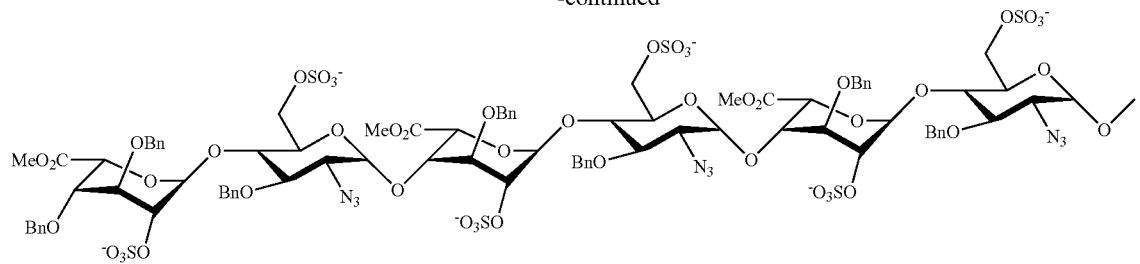
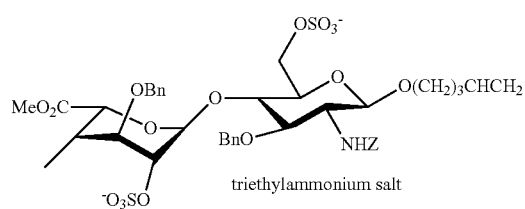
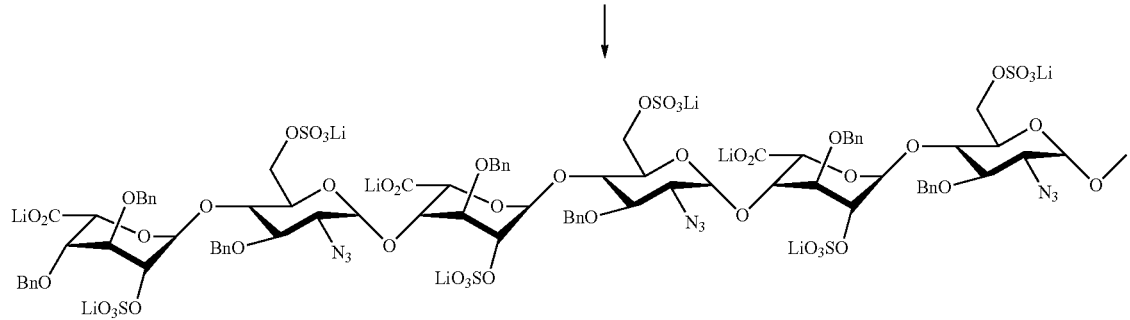
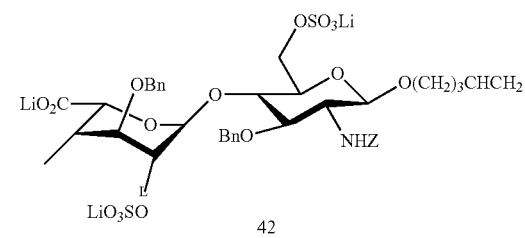
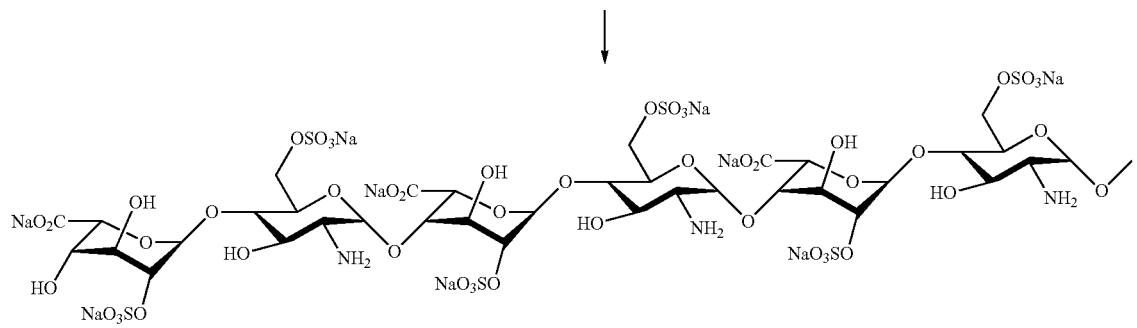
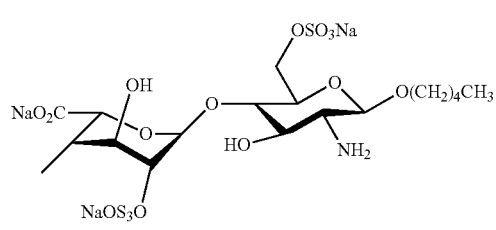

Preparation of 4-pentenyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-deoxy-2-[(benzyloxy)carbonyl]amino-β-D-glucopyranoside (No. 40)

To a solution of 39 (300 mg, 0.105 mmol) in a 3/2 mixture of methanol/dichloromethane (31 mL) is added, at 0° C., a 1M a methanolic solution of sodium methoxide (0.31 mL), in the presence of 3 Å molecular sieves. After stirring at 0° C. for 1 hour and at room temperature for 15 hours, the mixture is neutralized with H+ Dowex 50WX4 resin. After filtering and partially concentrating, the reaction mixture is purified on an LH-20 exclusion column using a 1:1 methanol/dichloromethane mixture as eluent, and, after pooling the fractions containing the product and concentrating under vacuum, the residue is purified on silica gel with a dichloromethane/ethyl acetate/ethanol mixture to give compound 40 (185 mg, 69%).
Rf=0.22 (9/1/0.3 $CH_2Cl_2$/EtOAc/EtOH).

Preparation of 4-pentenyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-β-D-glucopyranoside (No. 41)

Triethylamine/sulfur trioxide complex (513 mg, 5 mol per hydroxyl function) is added to a solution in N,N-dimethylformamide (6.3 mL, 90 L/mol) of compound 40 (178 mg, 70.8 μmol). After 17 hours of magnetic stirring at 55° C. sheltered from light, methanol is added at 0° C. and, after stirring for 30 minutes at 0° C. and then for 30 minutes at room temperature, the reaction medium is purified by means of an LH-20 column, using a 9:1 mixture of methanol/N,N-dimethylformamide as eluent. The fractions containing the product are then concentrated under high vacuum to give the desired compound 41 (241 mg, 87%).
Rf=0.33 (11/7/1.6/4 EtOAc/pyridine/AcOH/$H_2O$).

Preparation of 4-pentenyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-6-O-lithium sulfonato-β-D-glucopyranoside (No. 42)

To a solution of compound 41 (238 mg, 60 μmol) in a 1/1 mixture of methanol/tetrahydrofuran (9.6 mL) is added, at 0° C., a molar aqueous LiOH solution. After stirring for 1 hour at 0° C. and then for 16 hours at room temperature, the reaction medium is purified by means of an LH-20 column, using a 9:1 mixture of methanol/N,N-dimethylformamide as eluent. The fractions containing the product are then concentrated under high vacuum to give the desired compound 42.
Rf=0.42 (11/7/1.6/4 EtOAc/pyridine/AcOH/$H_2O$).

Preparation of pentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyl uronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyl uronate)-(1→4)-2-amino-2-deoxy-6-O-sodium sulfonato-β-D-glucopyranoside (No. 43)

To a solution in a 1/1 mixture of tert-butanol/water (14 mL) of compound 42 obtained previously are successively added ammonium formate (617 mg, 9.8 mmol) and then 10% Pd/C (1.55 g). After stirring vigorously for 4 hours at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 43 (123 mg, 61% (2 steps)).
Chemical shifts of the anomeric protons (600 MHz, $D_2O$)
δ 5.11 IdoUA$^{VIII}$, 5.38 Glc$^{VII}$, 5.19 IdoUA$^{VI}$, 5.38 Glc$^{V}$, 5.19 IdoUA$^{IV}$, 5.38 Glc$^{III}$, 5.21 IdoUA$^{II}$, 4.70 Glc$^{I}$

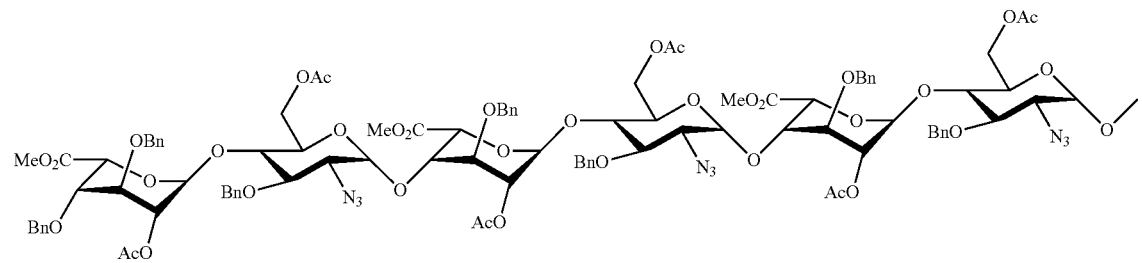

-continued
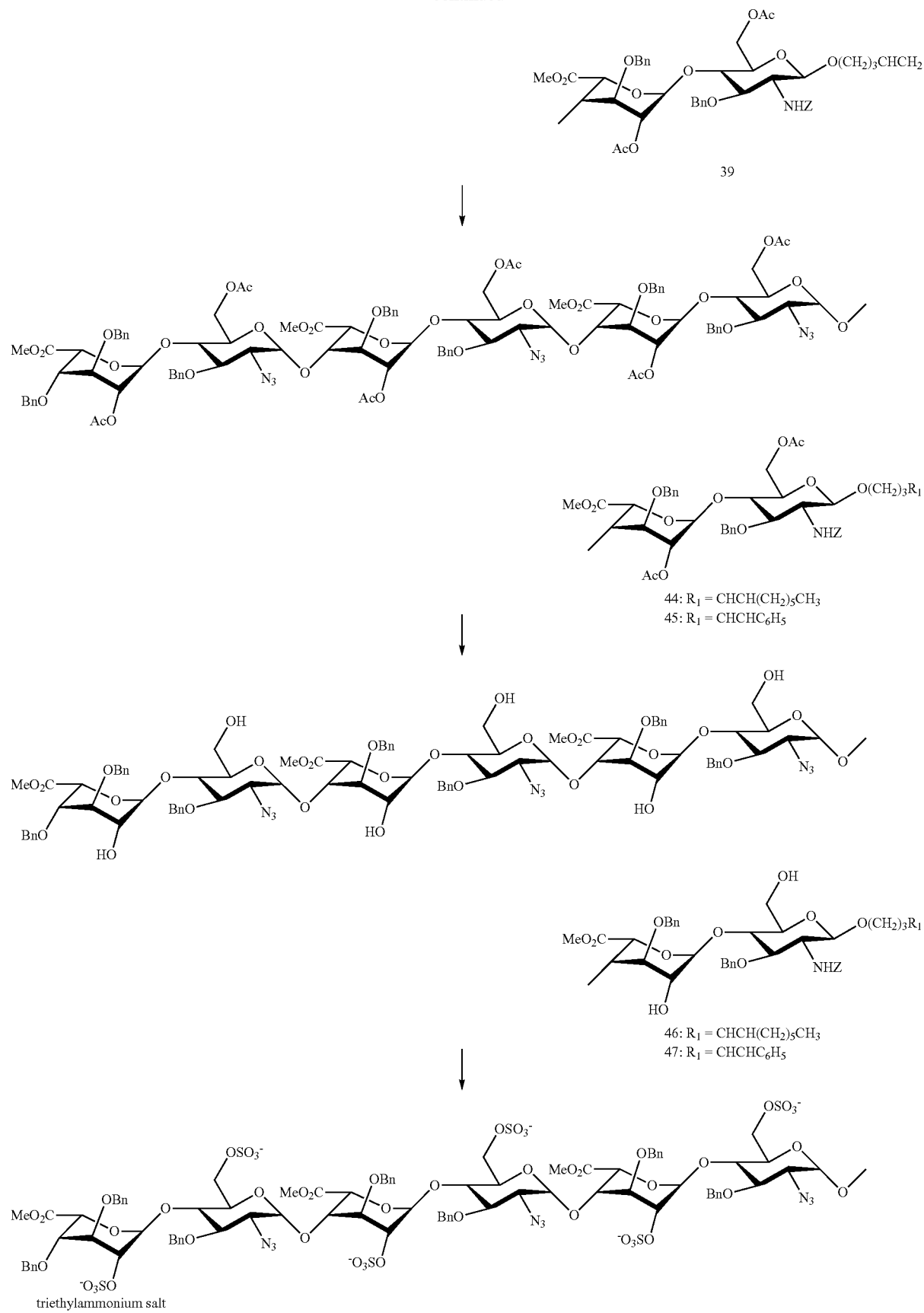

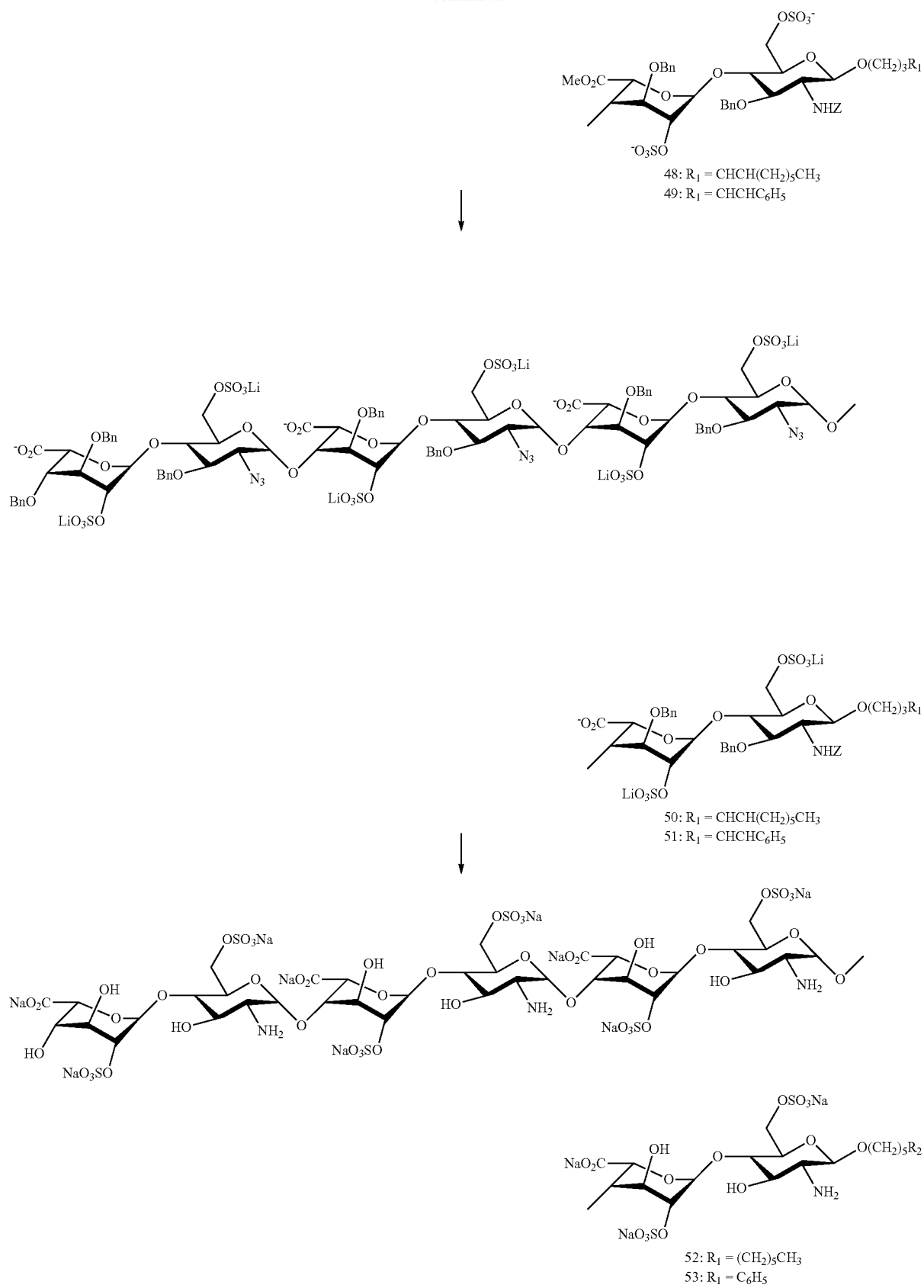

Preparation of (Z/E) undec-4-enyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 44)

To a solution of compound 39 (610 mg, 214 μmol) in dichloromethane (10.7 mL) are added 1-octene (67 μL, 2 molar equivalents) and first-generation Grubbs catalyst ($C_{44}H_{74}Cl_2P_2Ru$) (18 mg, 0.1 molar equivalent). After refluxing for 6 hours and then stirring overnight at room temperature, the mixture is concentrated under high vacuum and may be used under the same conditions in the case of an incomplete reaction. The crude reaction product is purified by chromatography on silica gel (toluene-acetone) to give the desired product 44 (131 mg, 20%).

Rf=0.18 (85/15 toluene/acetone).

Preparation of (Z/E) 5-phenyl-4-pentenyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-3-O-benzyl-2-deoxy-2-[(benzyloxy)carbonyl]amino-β-D-glucopyranoside (No. 45)

To a solution of compound 39 (100 mg, 35 μmol) in dichloromethane (1 mL) are added styrene (16 μL, 4 molar equivalents) and second-generation Grubbs catalyst ($C_{46}H_{65}Cl_2N_2PRu$) (1.8 mg, 0.06 molar equivalent). After refluxing for 8 hours and then stirring overnight at 35° C., the reagents are optionally added, if necessary. The mixture is then concentrated under high vacuum and then purified by chromatography on silica gel (toluene-ethyl acetate) to give the desired product 45 (38 mg, 37%).

Rf=0.25 (toluene-EtOAc 7/3).

Preparation of (Z/E) undec-4-enyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyl uronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-deoxy-2-[(benzyloxy)carbonyl]amino-β-D-glucopyranoside (No. 46)

To a solution of 44 (152 mg, 0.052 mmol) in a 3/2 mixture of methanol/dichloromethane (15 mL) is added, at 0° C., a 1M a methanolic solution of sodium methoxide (154 μL), in the presence of 3 Å molecular sieves. After stirring at 0° C. for 1 hour and at room temperature for 15 hours, the mixture is neutralized with $H^+$ Dowex 50WX4 resin. After filtering and partially concentrating, the reaction mixture is purified on an LH-20 exclusion column using a 1/1 mixture of methanol/dichloromethane as eluent, and, after pooling the fractions containing the product and concentrating under vacuum, the residue is purified on silica gel with a toluene/acetone/ethyl acetate/ethanol mixture to give compound 46 (83 mg, 61%).

Rf=0.25 (7/3/0.1 toluene/acetone/EtOH).

Preparation of (Z/E) 5-phenyl-4-pentenyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-deoxy-2-[(benzyloxy)carbonyl]amino-β-D-glucopyranoside (No. 47)

To a solution of 45 (229 mg, 0.078 mmol) in a 3/2 mixture of methanol/dichloromethane (23 mL) is added, at 0° C., a 1M a methanolic solution of sodium methoxide (232 μL), in the presence of 3 Å molecular sieves. After stirring at 0° C. for 1 hour and at room temperature for 15 hours, the mixture is neutralized with $H^+$ Dowex 50WX4 resin. After filtering and partially concentrating, the reaction mixture is purified on an LH-20 exclusion column using a 1/1 mixture of methanol/dichloromethane as eluent, and, after pooling the fractions containing the product and concentrating under vacuum, the residue is purified on silica gel with a dichloromethane/ethyl acetate/ethanol mixture to give compound 47 (141 mg, 69%).

Rf=0.15 (7/3/0.1 toluene/acetone/EtOH).

Preparation of (Z/E) undec-4-enyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-6-D-glucopyranoside (No. 48)

Triethylamine/sulfur trioxide complex (225 mg, 5 mol per hydroxyl function) is added to a solution in N,N-dimethylformamide (2.8 mL, 90 L/mol) of compound 46 (81 mg, 31 μmol). After 16 hours of magnetic stirring at 50° C. sheltered from light, methanol is added at 0° C. (0.2 mL) and after 35 minutes of stirring at 0° C. and then 2.5 hours at room temperature, the reaction medium is purified by means of an LH-20 column, using a 1/1/0.1 mixture of methanol/dichloromethane/N,N-dimethylformamide as eluent. The fractions containing the product are then concentrated under high vacuum to give the desired compound 48 (122 mg, 99%).

Rf=0.36 (11/7/1.6/4 EtOAc/pyridine/AcOH/H$_2$O).

Preparation of (Z/E) 5-phenyl-4-pentenyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-β-D-glucopyranoside (No. 49)

Triethylamine/sulfur trioxide complex (385 mg, 5 mol per hydroxyl function) is added to a solution in N,N-dimethylformamide (4.7 mL, 90 L/mol) of compound 47 (138 mg, 53 μmol). After 16 hours of magnetic stirring at 50° C. sheltered from light, methanol is added at 0° C. (0.35 mL) and after 30 minutes of stirring at 0° C. and then 1 hour at room temperature, the reaction medium is purified by means of an LH-20 column, using a 1/1/0.1 mixture of methanol/dichloromethane/N,N-dimethylformamide as eluent. The fractions containing the product are then concentrated under high vacuum to give the desired compound 49 (194 mg, 92%).

Rf=0.35 (11/7/1.6/4 EtOAc/pyridine/AcOH/H$_2$O).

Preparation of (Z/E) undec-4-enyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-6-O-lithium sulfonato-β-D-glucopyranoside (No. 50)

To a solution of compound 48 (119 mg, 29 μmol) in a 1/1 mixture of methanol/tetrahydrofuran (4.7 mL) is added, at 0° C., a molar aqueous LiOH solution (1.18 mL). After stirring for 1 hour at 0° C. and then for 19.5 hours at room temperature, the reaction medium is purified by means of an LH-20 column, using a 4:1 mixture of methanol/N,N-dimethylformamide as eluent. The fractions containing the product are then concentrated under high vacuum to give the desired compound 50.

Rf=0.40 (11/7/1.6/4 EtOAc/pyridine/AcOH/H$_2$O).

Preparation of (Z/E) 5-phenyl-4-pentenyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-6-O-lithium sulfonato-β-D-glucopyranoside (No. 51)

To a solution of compound 49 (190 mg, 47 μmol) in a 1/1 mixture of methanol/tetrahydrofuran (7.4 mL) is added, at 0° C., a molar aqueous LiOH solution (1.88 mL). After stirring for 1 hour at 0° C. and then for 16 hours at room temperature, the reaction medium is purified by means of an LH-20 column, using a 9:1 mixture of methanol/N,N-dimethylformamide as eluent. The fractions containing the product are then concentrated under high vacuum to give the desired compound 51.

Rf=0.44 (11/7/1.6/4 EtOAc/pyridine/AcOH/H$_2$O).

Preparation of undecyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyl uronate)-(1→4)-2-amino-2-deoxy-6-O-sodium sulfonato-β-D-glucopyranoside (No. 52)

To a solution in a 1/1 mixture of tert-butanol/water (6 mL) of compound 50 obtained previously are successively added ammonium formate (260 mg, 4.1 mmol) and then 10% Pd/C (672 mg). After 4 hours 5 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 52 (34 mg, 49% (2 steps)).

Mass: "ESI" method, negative mode: theoretical mass=2337.81; experimental mass: 2337.27±0.06 a.m.u. [M−4Na+4H].

Preparation of 5-phenylpentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-2-amino-2-deoxy-6-O-sodium sulfonato-β-D-glucopyranoside (No. 53)

To a solution in a 1/1 mixture of tert-butanol/water (9.2 mL) of compound 51 obtained previously are successively added ammonium formate (407 mg, 6.47 mmol) and then 10% Pd/C (1.05 g). After 4 hours 5 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 53 (79 mg, 72% (2 steps)).

"ESI" method, negative mode: multicharged ion detected m/z 537.0713 [M−4H]$^{4-}$ (acid form).

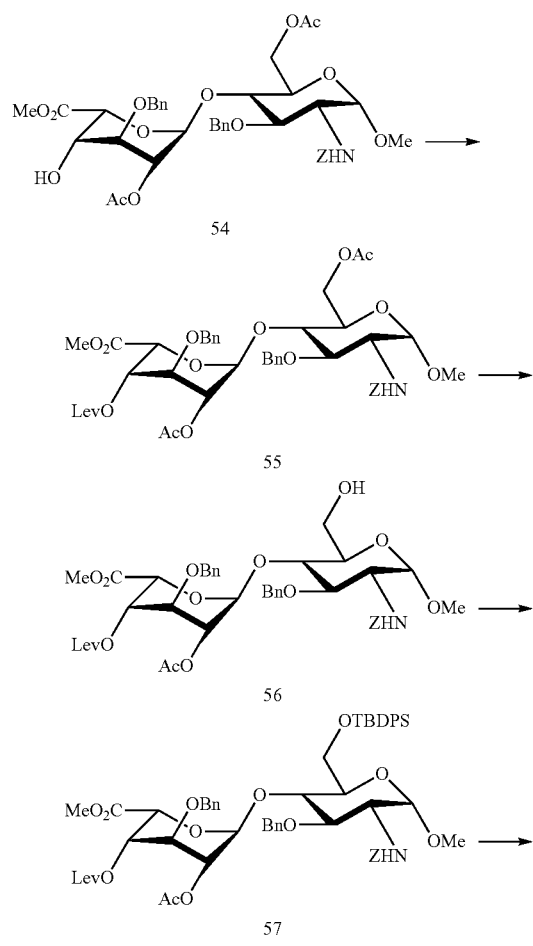

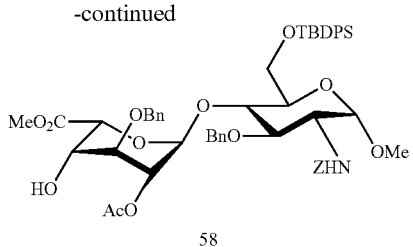

Preparation of methyl (methyl 2-O-acetyl-3-O-benzyl-4-O-levulinoyl-α-L-idopyranosyluronate)-(1→4)-6-O-acetyl-3-O-benzyl-2-benzyloxycarbonylamino-2-deoxy-α-D-glucopyranoside (No. 55)

To a solution of compound 54 (23.5 g, 30 mmol; *Carbohydrate Research* (1987), 167, 67-75) in dichloromethane (600 mL) are added, at 0° C. and under an inert atmosphere, 4-dimethylaminopyridine (733 mg, 6 mmol), 1-(3-dimethylaminopropyl)-3-ethylcarbodiimide hydrochloride (11.5 g, 60 mmol) and levulinic acid (6.2 mL; 60 mmol). After stirring for 16 hours at room temperature, the mixture is diluted with dichloromethane (1.5 L). The organic phase is washed successively with aqueous 10% potassium hydrogen sulfate solution, with water, with saturated sodium hydrogen carbonate solution and then with water, dried over sodium sulfate, filtered and then evaporated to dryness. The residue is purified by flash chromatography on a column of silica gel (1/3 cyclohexane/ethyl acetate) to give compound 55 (22.6 g).

Rf=0.37, silica gel, 1/3 cyclohexane/ethyl acetate

Preparation of methyl (methyl 2-O-acetyl-3-O-benzyl-4-O-levulinoyl-α-L-idopyranosyluronate)-(1→4)-3-O-benzyl-2-benzyloxycarbonylamino-2-deoxy-α-D-glucopyranoside (No. 56)

To a solution of compound 55 (20.2 g, 23 mmol) in a 1/1 tetrahydrofuran/methanol mixture (140 mL) is added, under an inert atmosphere, [tBu$_2$SnCl(OH)]$_2$ (226 mg, 0.79 mmol) prepared according to A. Orita et al., *Chem. Eur. J.* (2001) 7, 3321. The reaction medium is stirred for 38 hours at 35° C. After concentrating, the residue (20.8 g) is used without purification in the following step.

Rf=0.23, silica gel, 1/3 cyclohexane/ethyl acetate

Preparation of methyl (methyl 2-O-acetyl-3-O-benzyl-4-O-levulinoyl-α-L-idopyranosyluronate)-(1→4)-3-O-benzyl-2-benzyloxycarbonylamino-6-O-tert-butyldiphenylsilyl-2-deoxy-α-D-glucopyranoside (No. 57)

To a solution of the crude compound 56 (23 mmol) in dichloromethane (190 mL) are added, at 0° C. and under an inert atmosphere, triethylamine (8 mL, 57.5 mmol), 4-dimethylaminopyridine (1.4 g, 11.5 mmol) and tert-butyldiphenylsilyl chloride (12 mL, 46.0 mmol). The reaction medium is stirred for 16 hours at room temperature. The reaction mixture is diluted with dichloromethane. The organic phase is washed successively with saturated sodium chloride solution and then with water, dried over sodium sulfate, filtered and then evaporated. The residue is purified by flash chromatography on a column of silica gel (2/1 cyclohexane/ethyl acetate) to give compound 57 (24.4 g).

Rf=0.42, silica gel, 2/1 cyclohexane/ethyl acetate

Preparation of methyl (methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 58)

To a solution of compound 57 (22.6 g, 20.0 mmol) in a 1/2 toluene/ethanol mixture (2.5 L) is added hydrazine acetate (9.21 g, 100.0 mmol). The reaction medium is stirred for 30 minutes at room temperature. After concentrating, the residue is purified by flash chromatography on a column of silica gel (2/1 cyclohexane/ethyl acetate) to give 17.6 g of compound 58.

Rf=0.40, silica gel, 2/1 cyclohexane/ethyl acetate.

Chemical shifts of anomeric protons (500 MHz, CDCl$_3$) δ 5.19 IdoUA$^{II}$, 4.63 Glc$^I$ LC-MS m/z 978.5 [(M+H)$^+$]. T$_R$=12.29 min

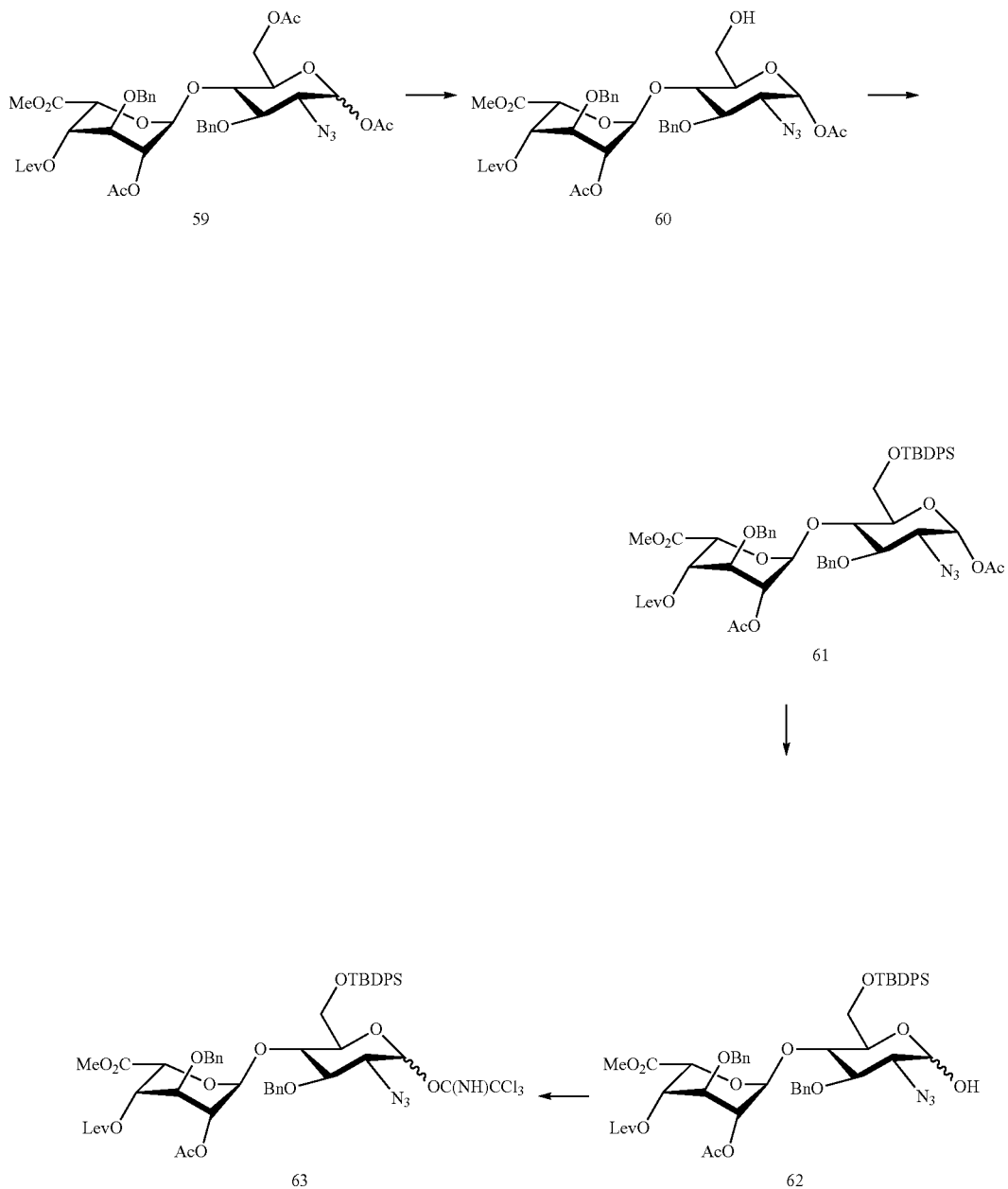

Preparation of (methyl 2-O-acetyl-3-O-benzyl-4-O-levulinoyl-α-L-idopyranosyluronate)-(1→4)-1-O-acetyl-2-azido-3-O-benzyl-2-deoxy-α-D-glucopyranose (No. 60)

To a solution of 59 (11 g, 13.7 mmol) (C. Tabeur, et al., Carbohydr. Res., 281 (1996) 253-276) in a 1/1 mixture of methanol/tetrahydrofuran (80 mL) is added [tBu$_2$SnCl(OH)]$_2$ (0.55 g, 0.14 molar equivalent) prepared according to A. Orita et al., Chem. Eur. J. (2001) 7, 3321. After stirring at 35° C. for 5.5 hours, then at room temperature for 16 hours and then again at 35° C. for 4 hours, the reaction mixture is concentrated under vacuum and then purified by chromatography to give compound 60 (5.97 g, 57%).

LC-MS m/z 780.2 [(M+Na)$^+$]. T$_R$=9.14 min

Preparation of (methyl 2-O-acetyl-3-O-benzyl-4-O-levulinoyl-α-L-idopyranosyluronate)-(1→4)-1-O-acetyl-2-azido-3-O-benzyl-6-O-tert-butyldiphenylsilyl-2-deoxy-α-D-glucopyranose (No. 61)

Compound 60 (5.97 g, 7.88 mmol) is dissolved in dichloromethane (63 mL). 4-Dimethylaminopyridine (0.481 g, 0.5 molar equivalent), triethylamine (2.7 mL, 2.5 molar equivalents), and tert-butyldiphenylsilyl chloride (4 mL, 2 molar equivalents) are successively added at 0° C. under argon. After magnetic stirring for 4 hours, the reaction medium is diluted with dichloromethane, washed with aqueous 10% potassium hydrogen sulfate solution, with water, dried (Na$_2$SO$_4$), filtered and concentrated. The residue obtained is purified on silica (ethyl acetate-heptane) to give 61 (7 g, 90%).

LC-MS m/z 1018.3 [(M+Na)$^+$]. T$_R$=12.33 min

Preparation of (methyl 2-O-acetyl-3-O-benzyl-4-O-levulinoyl-α-L-idopyranosyluronate)-(1→4)-2-azido-3-O-benzyl-6-O-tert-butyldiphenylsilyl-2-deoxy-α,β-D-glucopyranose (No. 62)

To a solution of compound 61 (7 g, 7.03 mmol) in diethyl ether (70 mL) is added, at 0° C., benzylamine (BnNH$_2$) (29 mL, 38 molar equivalents). After 15 minutes of stirring at 0° C. and then 6 hours at room temperature, the reaction mixture is diluted with ethyl acetate, and then neutralized with cold 1N HCl (0-4° C.), washed with water, dried (Na$_2$SO$_4$), filtered and concentrated, and purified on silica gel (ethyl acetate-toluene) to give 62 (5.86 g, 87%).

LC-MS m/z 976.3 [(M+Na)$^+$]. T$_R$=27.6/27.8 min

Preparation of (methyl 2-O-acetyl-3-O-benzyl-4-O-levulinoyl-α-L-idopyranosyluronate)-(1→4)-2-azido-3-O-benzyl-6-O-tert-butyldiphenylsilyl-2-deoxy-α,β-D-glucopyranose trichloroacetimidate (No. 63)

To a solution of compound 62 (6.5 g, 6.81 mmol) in dichloromethane (140 mL) and in the presence of powdered 4 Å molecular sieves (7 g), is added, under argon, cesium carbonate (Cs$_2$CO$_3$) (3.5 g, 1.6 molar equivalents), followed by addition, at 0° C., of trichloroacetonitrile (CCl$_3$CN) (3.4 mL, 5.0 molar equivalents). After stirring for 15 minutes 0° C. and then for 5 hours at room temperature, the reaction mixture is filtered and then concentrated. The residue is purified on silica gel (1/4 ethyl acetate/toluene+0.1% triethylamine) to give 63 (6.33 g, 85%).

LC-MS m/z 1119.1 [(M+Na)$^+$]. T$_R$=31.2 min

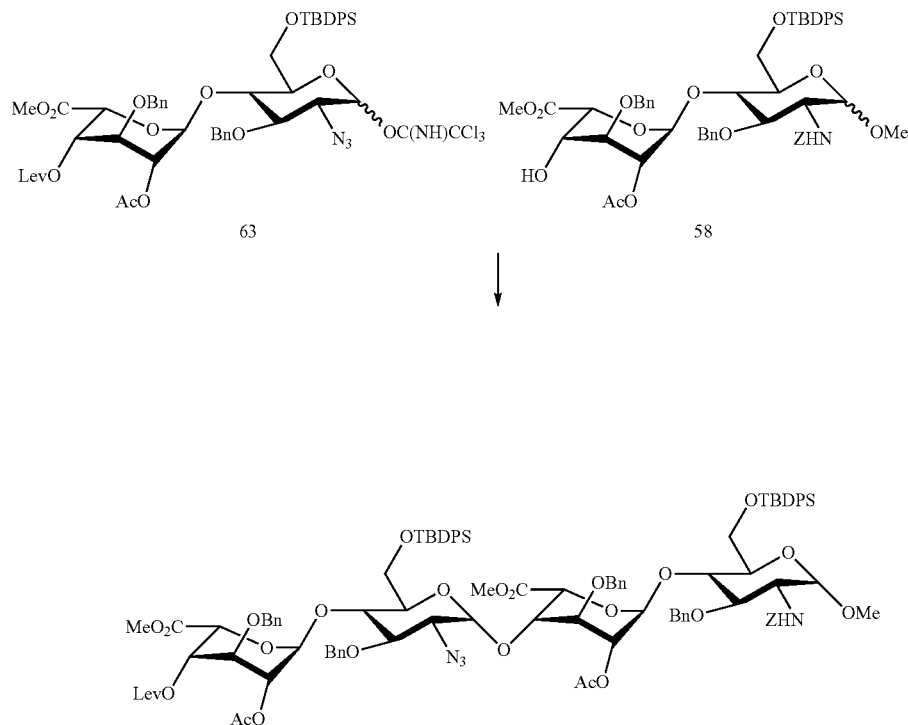

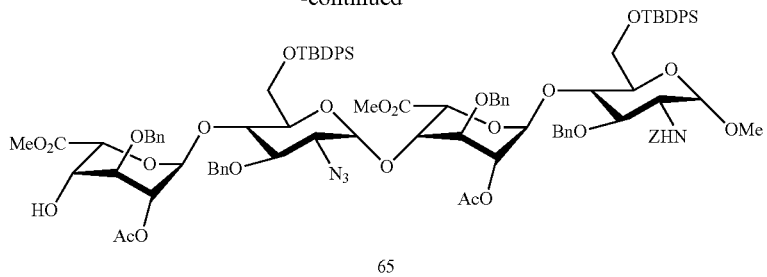

65

Preparation of methyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 64)

A mixture of the glycosyl acceptor 58 (8.80 g, 9.00 mmol), imidate 63 (6.58 g, 6.00 mmol) and powdered 4 Å molecular sieves (4.50 g) in dichloromethane (210 mL) is stirred under an argon atmosphere for 1 hour at 25° C. The reaction mixture is cooled to −20° C. and a 1 M solution of tert-butyldimethylsilyl triflate in dichloromethane (900 μL) is added. After 1 hour 20 minutes, the reaction medium is neutralized by addition of solid sodium hydrogen carbonate. After filtering through Celite® and concentrating, the residue obtained is chromatographed on a Sephadex® LH-20 column (190×3.2 cm, 1/1 dichloromethane/ethanol) to give 8.26 g of compound 64.

Rf=0.30, silica gel, 2/1 cyclohexane/ethyl acetate

Preparation of methyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 65)

Compound 64 (8.26 g, 4.31 mmol) is converted into compound 65 (6.41 g) according to the same procedure as that described for the synthesis of 58.

Rf=0.34, silica gel, 2/1 cyclohexane/ethyl acetate

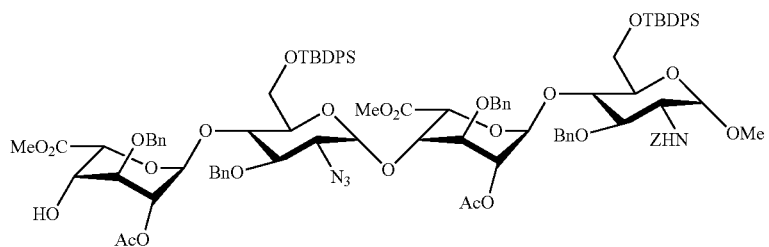

65

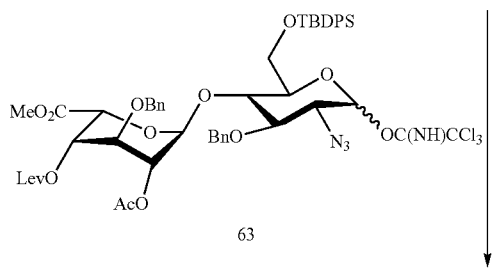

63

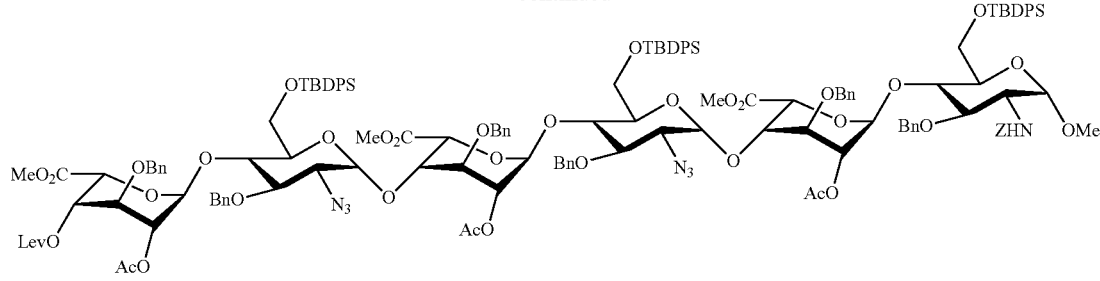

66

↓

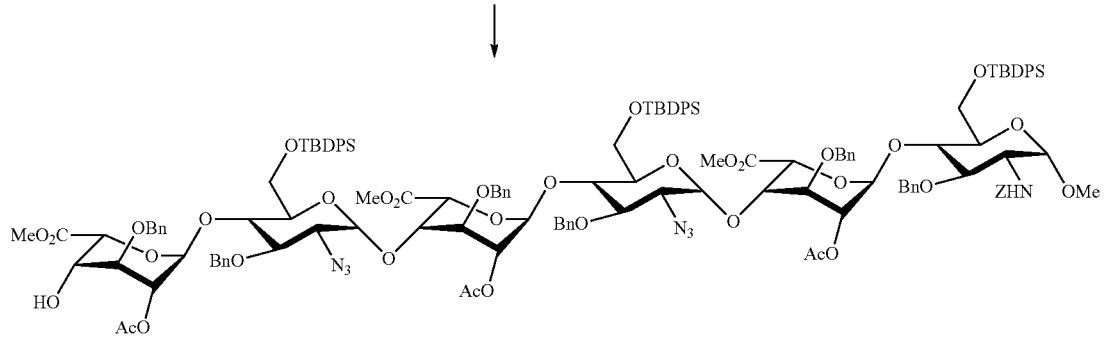

67

Preparation of methyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 66)

A mixture of the glycosyl acceptor 65 (7.42 g, 4.09 mmol), imidate 63 (6.73 g, 6.1 mmol), and powdered 4 Å molecular sieves (4.60 g) in dichloromethane (215 mL) is stirred under an argon atmosphere for 1 hour at 25° C. The reaction mixture is cooled to −20° C. and a 1 M solution of tert-butyldimethylsilyl triflate in dichloromethane (920 µL) is added. After 1 hour 30 minutes, the reaction medium is neutralized by addition of solid sodium hydrogen carbonate. After filtering through Celite®, the reaction medium is diluted with dichloromethane (800 mL). The organic phase is washed successively with 2% sodium hydrogen carbonate solution, with water and then dried over sodium sulfate, filtered and evaporated to dryness. The residue obtained is purified by chromatography on a Sephadex® LH-20 column (190×3.2 cm, 1/1 dichloromethane/ethanol), followed by chromatography on a column of silica gel (6/1 toluene/ethyl acetate) to give 6.13 g of compound 66.

Rf=0.46, silica gel, 4/1 toluene/ethyl acetate

Preparation of methyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1×4)-3-O-benzyl-2-benzyloxycarbonylamino-6-O-tert-butyldiphenylsilyl-2-deoxy-α-D-glucopyranoside (No. 67)

Compound 66 (7.14 g, 2.59 mmol) is converted into compound 67 (6.07 g) according to the same procedure as that described for the preparation of compound 58.

Rf=0.37, silica gel, 2/1 cyclohexane/ethyl acetate

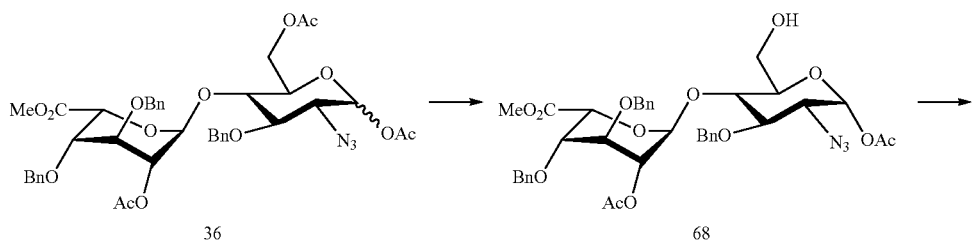

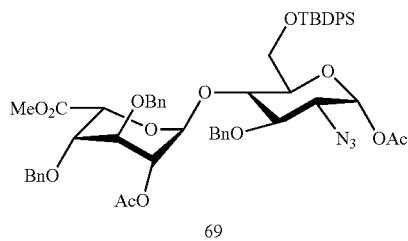

69

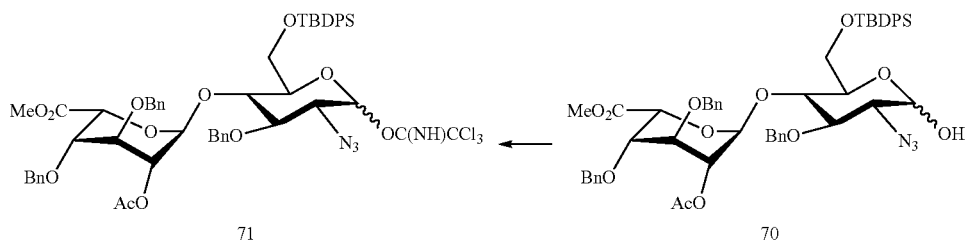

71                                              70

Preparation of (methyl 2-O-acetyl-3,4-di-O-benzyl-α-L-idopyranosyluronate)-(1→4)-1-O-acetyl-2-azido-3-O-benzyl-2-deoxy-α-D-glucopyranose (No. 68)

To a solution of 36 (5.05 g, 6.3 mmol) in a 1/1 mixture of methanol/tetrahydrofuran (76 mL) is added [tBu$_2$SnCl(OH)]$_2$ (0.25 g, 0.14 molar equivalent) prepared according to A. Orita et al., Chem. Eur. J. (2001) 7, 3321. After stirring at room temperature for 72 hours, the reaction mixture is concentrated under vacuum and then purified by chromatography to give compound 68 (2.89 g, 64%).

LC-MS m/z 772.4 [(M+Na)$^+$]. T$_R$=10.23 min

Preparation of (methyl 2-O-acetyl-3,4-di-O-benzyl-α-L-idopyranosyluronate)-(1→4)-1-O-acetyl-2-azido-3-O-benzyl-6-O-tert-butyldiphenylsilyl-2-deoxy-α-D-glucopyranose (No. 69)

Compound 68 (2.89 g, 3.86 mmol) is dissolved in dichloromethane (31 mL). Triethylamine (1.3 mL, 2.5 molar equivalents), 4-dimethylaminopyridine (0.235 g, 0.5 molar equivalent), and tert-butyldiphenylsilyl chloride (2 mL, 2 molar equivalents) are successively added at 0° C. under argon. After magnetic stirring for 3 hours, the reaction medium is diluted with dichloromethane, washed with aqueous 10% potassium hydrogen sulfate solution, with water, dried (Na$_2$SO$_4$), filtered and concentrated. The residue obtained is purified on silica (ethyl acetate/cyclohexane) to give 69 (3.4 g, 90%).

LC-MS m/z 1010.6 [(M+Na)$^+$]. T$_R$=13.10 min

Preparation of (methyl 2-O-acetyl-3,4-di-O-benzyl-α-L-idopyranosyluronate)-(1→4)-2-azido-3-O-benzyl-6-O-tert-butyldiphenylsilyl-2-deoxy-α,β-D-glucopyranose (No. 70)

To a solution of compound 69 (3.44 g, 3.48 mmol) in diethyl ether (35 mL) is added, at 0° C., benzylamine (BnNH$_2$) (14.5 mL, 38 molar equivalents). After stirring for 8 hours at room temperature, the reaction mixture is placed at −18° C. for 16 hours, and then again for 2.5 hours at room temperature. The medium is then diluted with ethyl acetate, and then neutralized with cold 1N HCl (0-4° C.), washed with water, dried (Na$_2$SO$_4$), filtered and concentrated, and purified on silica gel (ethyl acetate/cyclohexane 15/85) to give 70 (3.83 g, 91%).

LC-MS m/z 963.6 [(M+NH$_4$)$^+$]. T$_R$=12.37, 12.47 min

Preparation of (methyl 2-O-acetyl-3,4-di-O-benzyl-α-L-idopyranosyluronate)-(1→4)-2-azido-3-O-benzyl-6-O-tert-butyldiphenylsilyl-2-deoxy-α,β-D-glucopyranose trichloroacetimidate (No. 71)

To a solution of compound 70 (2.99 g, 3.16 mmol) in dichloromethane (60 mL) and in the presence of powdered 4 Å molecular sieves (3 g), are added, at 0° C. under argon, cesium carbonate (Cs$_2$CO$_3$) (1.6 g, 1.6 molar equivalents) and then trichloroacetonitrile (CCl$_3$CN) (1.6 mL, 5.0 molar equivalents). After 20 minutes of stirring at 0° C., and 7 hours at room temperature, storing at −18° C. for 16 hours, and then magnetic stirring for 8 hours at room temperature, storing at −18° C. for 16 hours, and finally magnetic stirring for 1 hour at room temperature, the reaction mixture is filtered and then concentrated. The residue is purified on silica gel (15/85 ethyl acetate/cyclohexane+0.1% triethylamine) to give 71 (2.69 g, 78%).

LC-MS m/z 1113.4 [(M+Na)$^+$]. T$_R$=14.58 min

49 50
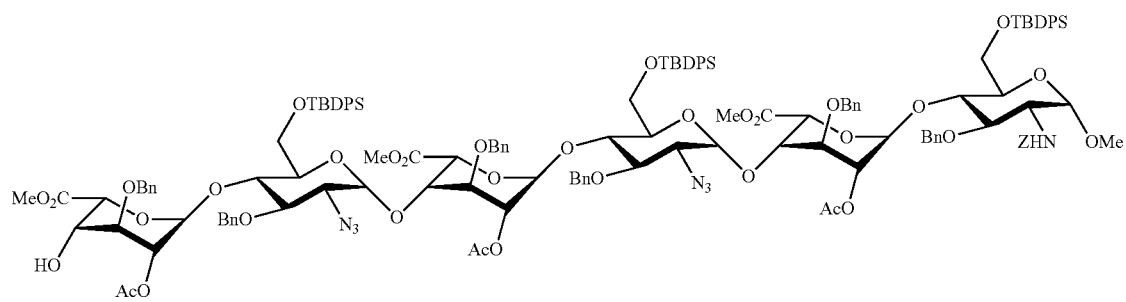
67
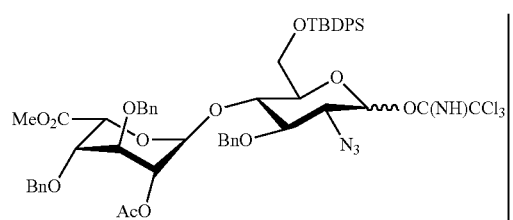
71
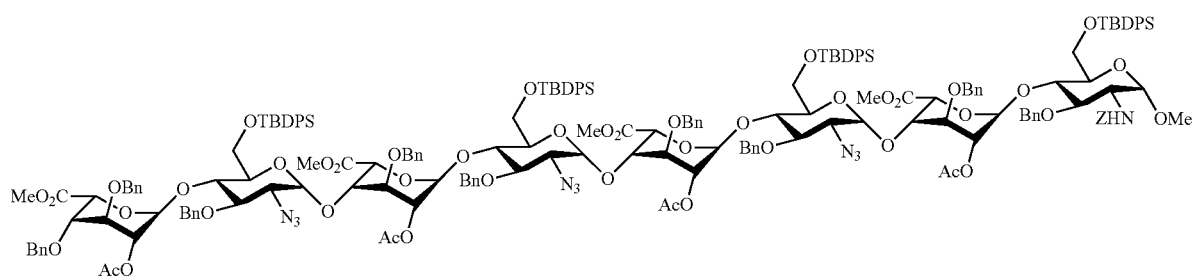
72
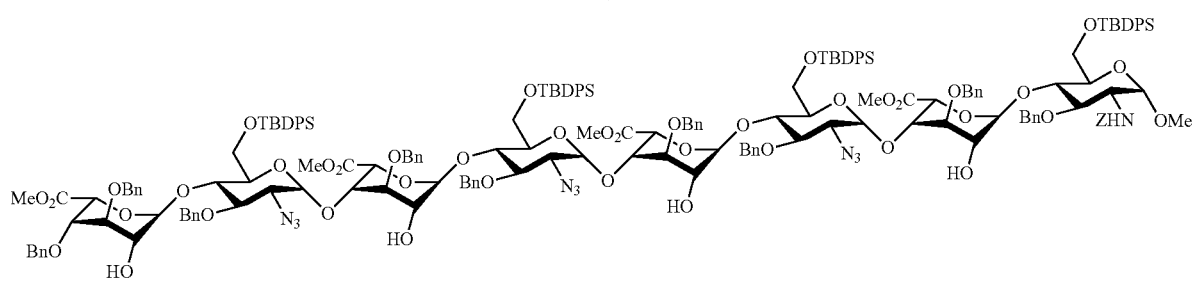
73

-continued
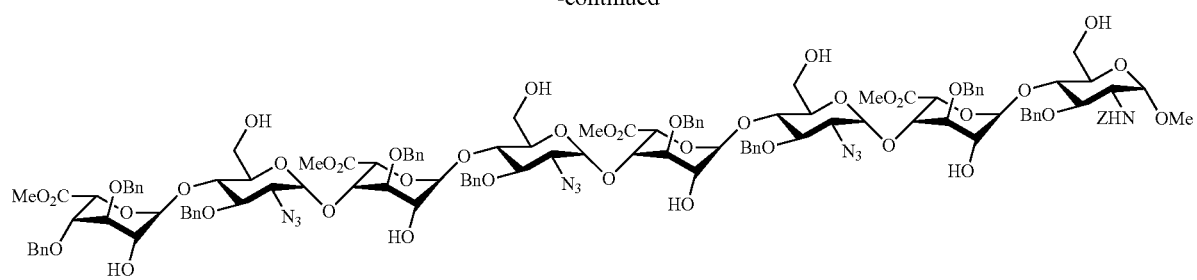
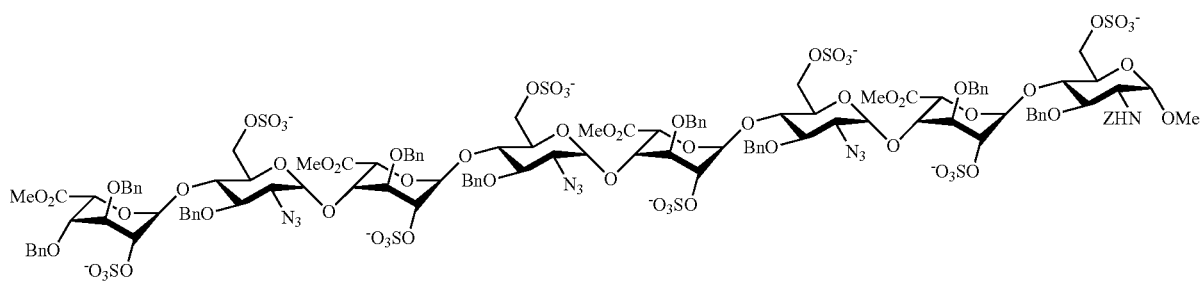
triethylammonium salt
75
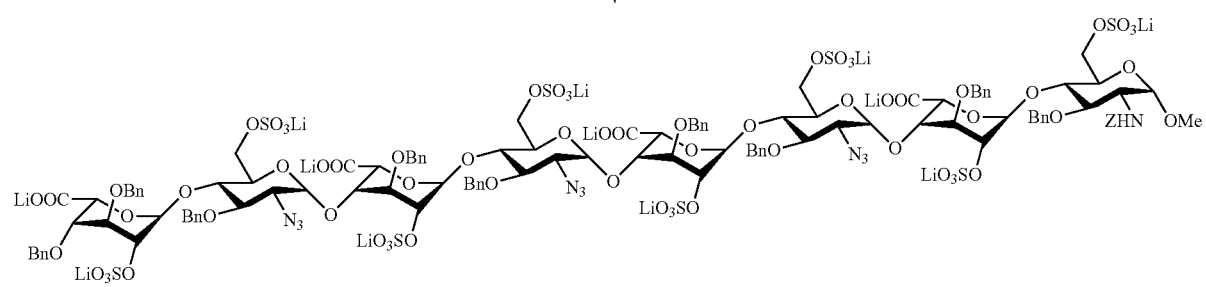
76
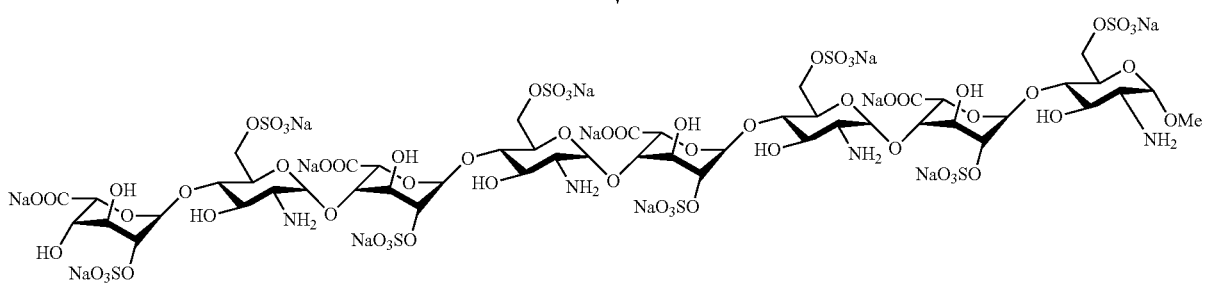
77

Preparation of methyl (methyl 2-O-acetyl-3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)]2-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 72)

A mixture of the glycosyl acceptor 67 (3.50 g, 1.32 mmol), imidate 71 (2.16 g, 1.98 mmol) and powdered 4 Å molecular sieves (1.48 g) in dichloromethane (69 mL) is stirred under an argon atmosphere for 1 hour at room temperature. The reaction mixture is cooled to −20° C. and a 1 M solution of tert-butyldimethylsilyl triflate in dichloromethane (297 µL) is added. After 2 hours 30 minutes, the reaction medium is neutralized by addition of solid sodium hydrogen carbonate. After filtering through Celite®, the reaction medium is diluted with dichloromethane (400 mL). The organic phase is washed successively with 2% sodium hydrogen carbonate solution, with water and then dried over sodium sulfate, filtered and then evaporated to dryness. The residue obtained is purified by chromatography on a Sephadex® LH-20 column (190×3.2 cm, 1/1 dichloromethane/ethanol), followed by chromatography on a column of silica gel (cyclohexane/ethyl acetate 4/1) to give 3.04 g of compound 72.
Rf=0.30, silica gel, 3/1 cyclohexane/ethyl acetate Preparation of methyl (methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-[(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)]2-(methyl 3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 73)

To a solution of compound 72 (2.23 g, 0.623 mmol) in a 2/3 dichloromethane/methanol mixture (187 mL) containing 3 Å sieves (78 mg) is added, under an argon atmosphere and at 0° C., a 1 M solution of sodium methoxide in methanol (99.7 µL). After 24 hours at room temperature, the reaction medium is neutralized with Dowex AG 50 WX4 H$^+$ resin. After filtering and concentrating, the residue is chromatographed on a Sephadex® LH-20 column (120×3 cm, 1/1 dichloromethane/ethanol), followed by flash chromatography on a column of silica gel (1/066/34 cyclohexane/ethyl acetate) to give 1.80 g of compound 73.
Rf=0.38, silica gel, 3/1 cyclohexane/ethyl acetate Preparation of methyl (methyl 3,4-di-O-benzyl-α-L-idopyranosyluronate)-(1→4)-(2-azido-3-O-benzyl-2-deoxy-α-D-glucopyranosyl)-(1→4)-[methyl 3-O-benzyl-α-L-idopyranosyluronate-(1→4)-(2-azido-3-O-benzyl-2-deoxy-α-D-glucopyranosyl)-(1→4)]2-(methyl 3-O-benzyl-α-L-idopyranosyluronate)-(1→4)-3-O-benzyl-2-benzyloxycarbonylamino-2-deoxy-α-D-glucopyranoside (No. 74)

To a solution of compound 73 (44.0 mg, 0.013 mmol) in methanol (1.7 mL) is added ammonium fluoride (38.0 mg, 1.03 mmol). After 140 hours of stirring at room temperature, the reaction mixture is applied to a Sephadex® LH-20 column (95×2 cm, 1/1 dichloromethane/ethanol), followed by flash chromatography on a column of silica gel (3/2 toluene/acetone) to give compound 74 (24.2 mg).
Rf=0.46, silica gel, 3/2 toluene/acetone Preparation of methyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-[(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)]$_2$-(1→4)-(methyl 3-O-benzyl-2-O-triethylammonium sulfonato-α-L-idopyranosyluronate)-(1→4)-3-O-benzyl-2-benzyloxycarbonylamino-2-deoxy-6-O-triethylammonium sulfonato-α-D-glucopyranoside (No. 75)

Compound 74 (24.2 mg, 9.96 µmol) is dried by codistillation of N,N-dimethylformamide (3×1.0 mL) and is then dissolved in N,N-dimethylformamide (1.0 mL). To this solution is added triethylamine-sulfur trioxide complex (72.2 mg, 0.4 mmol). The mixture is stirred for 16 hours at 55° C. sheltered from light and the excess reagent is then destroyed with methanol (16.2 µL). The reaction medium is applied to a Sephadex® LH-20 column (120×3 cm) eluted with a 1/1 mixture of dichloromethane/ethanol to give compound 75 (29.0 mg).
Rf=0.26, silica gel, ethyl acetate/pyridine/acetic acid/water 28/16/3.8/9.

Preparation of methyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-[(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)]$_2$-(1→4)-(lithium 3-O-benzyl-2-O-lithium sulfonato-α-L-idopyranosyluronate)-(1→4)-3-O-benzyl-2-benzyloxycarbonylamino-2-deoxy-6-O-lithium sulfonato-α-D-glucopyranoside (No. 76)

To a solution of compound 75 (78.5 mg, 30.1 µmol) in a 1/1 tetrahydrofuran/methanol mixture (3.2 mL) is added, at 0° C., a 0.7 M solution of lithium hydroxide in water (440 µL). After 1 hour at 0° C. and then 16 hours at room temperature, the solution is applied to a Sephadex® LH-20 column (3×120 cm) eluted with a 50/50/1 dichloromethane/ethanol/water mixture to give compound 76 (60.3 mg).
$[\alpha]_D$ 13.1° (c 1.0; MeOH)

Preparation of methyl (sodium 2-O-sodium sulfonato-α-L-idopyranosyluronate)-(1→4)-(2-amino-2-deoxy-6-O-sodium sulfonato-α-D-glucopyranosyl)-1→4)-(sodium 2-O-sodium sulfonato-α-L-idopyranosyluronate)-[(1→4)-(2-amino-2-deoxy-6-O-sodium sulfonato-α-D-glucopyranosyl)]$_2$-(1→4)-(sodium 2-O-sodium sulfonato-α-L-idopyranosyluronate)-(1→4)-2-amino-2-deoxy-6-O-sodium sulfonato-α-D-glucopyranoside (No. 77)

To a solution of compound 76 (19.3 mg, 6.16 µmol) in a 1/1 tert-butanol/water mixture (1.2 mL) are successively added ammonium formate (50.8 mg) and Pd/C 10% (125 mg). After 4 hours at room temperature, the reaction mixture is filtered (Millipore® LSWP 5 μm filter) and then applied to a column of fine Sephadex® G-25 gel (95×2 cm) eluted with aqueous 0.2 M NaCl solution. The fractions containing the expected product are pooled and applied to a column of fine Sephadex® G-25 (95×2 cm) eluted with water, to give 11.2 mg of compound 77.

Mass: "ESI" method, negative mode: theoretical mass=2285.47; experimental mass: 2197.20±0.34 a.m.u. (iduronic acids observed in COOH form)

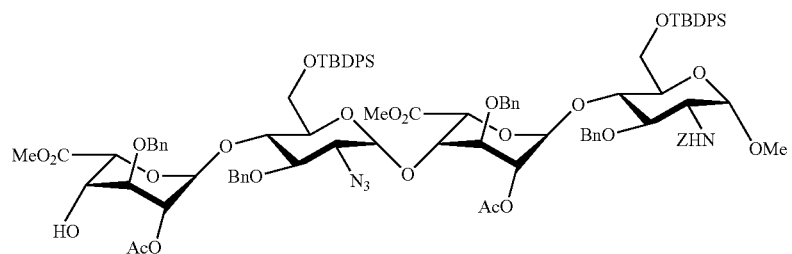

65

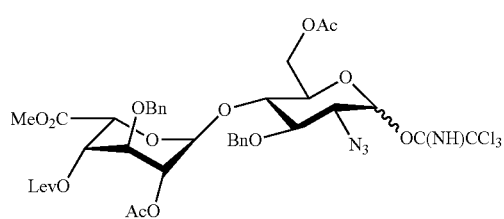

27

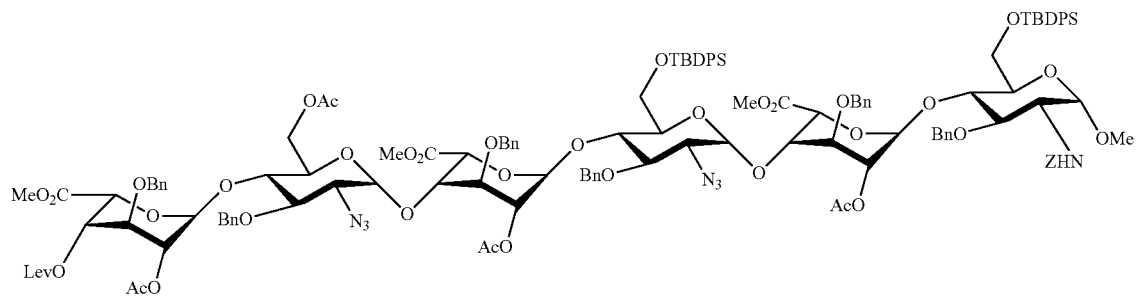

78

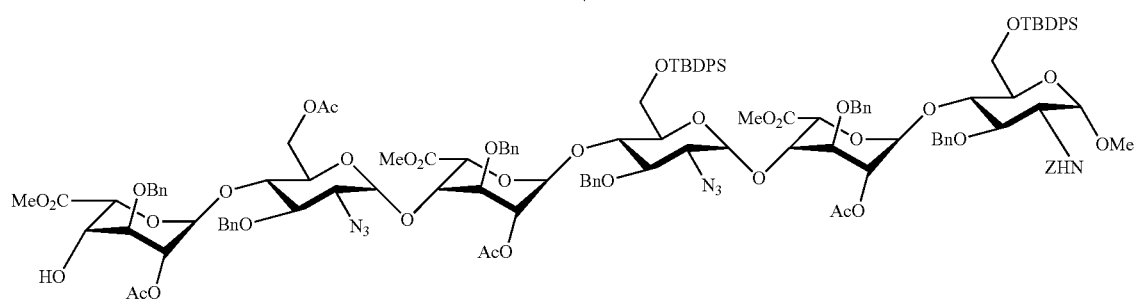

79

Preparation of methyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 78)

A mixture of the glycosyl acceptor 65 (1.82 g, 1.00 mmol), imidate 27 (1.35 g, 1.50 mmol) and powdered 4 Å molecular sieves (1.12 g) in dichloromethane (52 mL) is stirred under an argon atmosphere for 1 hour at 25° C. The reaction mixture is cooled to −20° C. and a 1 M solution of tert-butyldimethylsilyl triflate in dichloromethane (224 µL) is then added. After 50 minutes, the reaction medium is neutralized by addition of solid sodium hydrogen carbonate. After filtering through Celite®, the reaction medium is diluted with dichloromethane (500 mL). The organic phase is washed successively with aqueous 2% sodium hydrogen carbonate solution, with water and then dried over sodium sulfate, filtered and then evaporated to dryness. The residue obtained is chromatographed on a column (Sephadex® LH-20, 190×3.2 cm, 1/1 dichloromethane/ethanol), followed by flash chromatography on a column of silica gel (1/0→3/1 toluene/acetone) to give 1.57 g of compound 78.

Rf=0.47, silica gel, 3/1 toluene/acetone

Preparation of methyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 79)

Compound 78 (1.56 g, 0.61 mmol) is converted into compound 79 (1.44 g) according to the same procedure as that described for the preparation of compound 58.

Rf=0.52, silica gel, 1/1 toluene/acetone

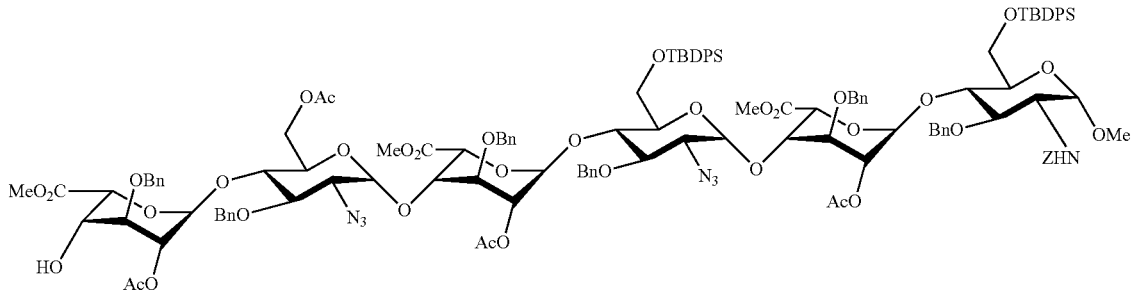

79

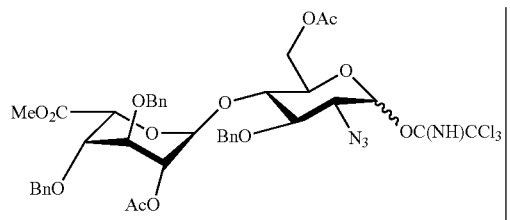

38

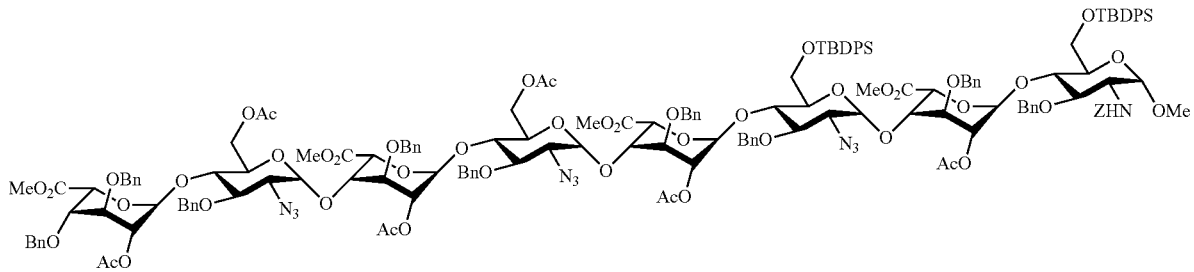

80

-continued
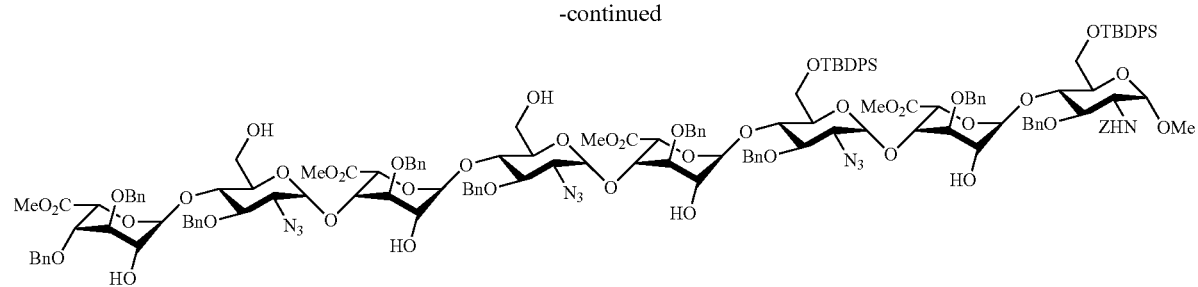
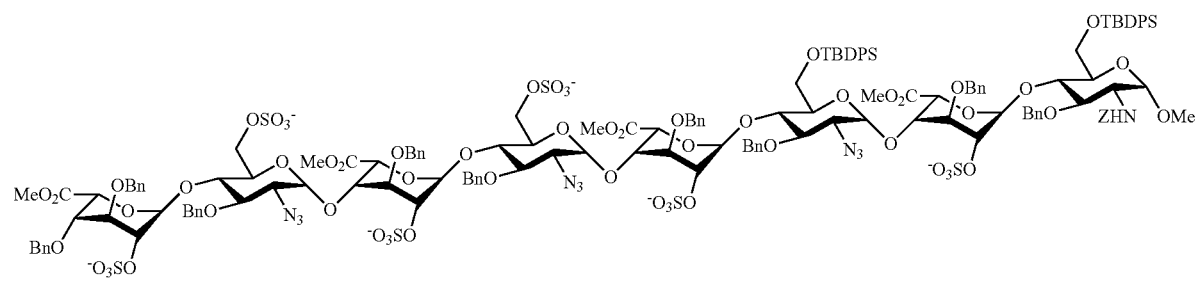
triethylammonium salt
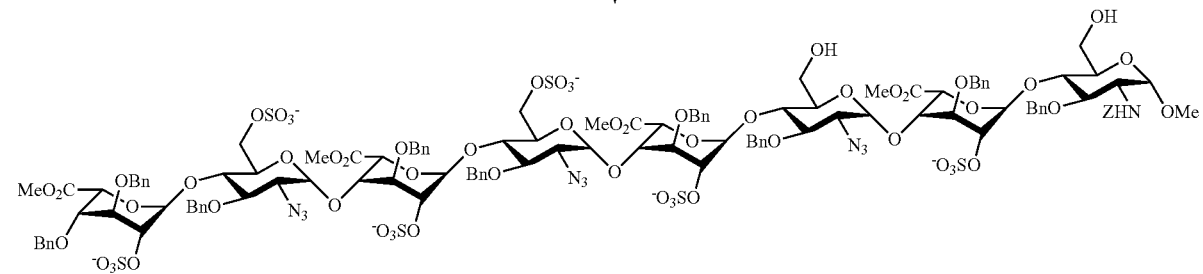
ammonium salt
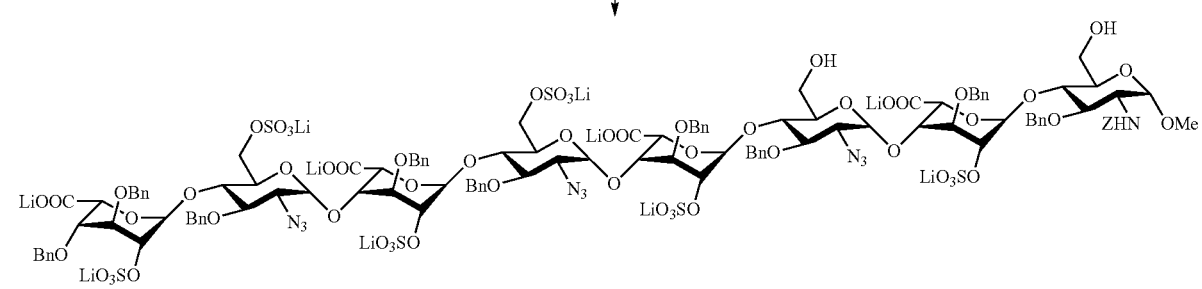

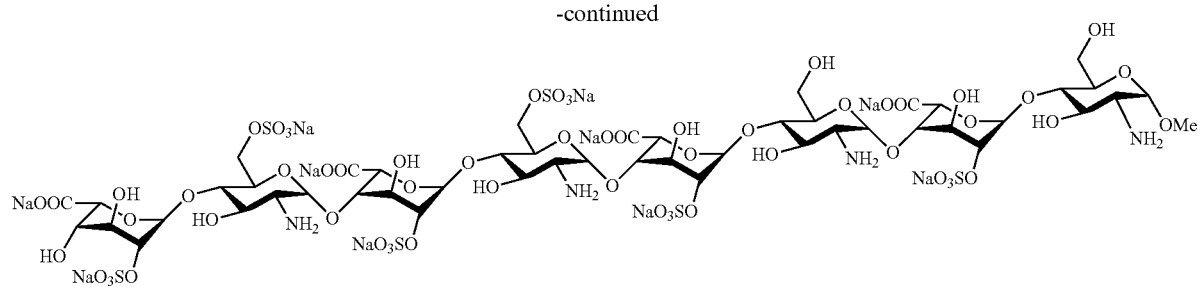

Preparation of methyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 80)

A mixture of the glycosyl acceptor 79 (1.0 g, 0.41 mmol), imidate 38 (543 mg, 0.61 mmol) and powdered 4 Å molecular sieves (455 mg) in dichloromethane (21 mL) is stirred under an argon atmosphere for 1 hour at room temperature. The reaction mixture is cooled to −20° C. and a 1 M solution of tert-butyldimethylsilyl triflate in dichloromethane (91.0 µL) is added. After 1 hour 10 minutes, the reaction medium is neutralized by addition of solid sodium hydrogen carbonate. After filtering through Celite®, the reaction medium is diluted with dichloromethane (250 mL). The organic phase is washed successively with aqueous 2% sodium hydrogen carbonate solution, with water and then dried over sodium sulfate, filtered and then evaporated to dryness. The residue obtained is purified by chromatography on a Sephadex® LH-20 column (190×3.2 cm, 1/1 dichloromethane/ethanol), followed by flash chromatography on a column of silica gel (1/00/1 toluene/ethyl acetate) to give compound 80 (822.4 mg).

Rf=0.44, silica gel, 3/1 toluene/ethyl acetate

Preparation of methyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-3-O-benzyl-2-benzyloxycarbonylamino-6-O-tert-butyldiphenylsilyl-2-deoxy-α-D-glucopyranoside (No. 81)

Compound 80 (820 mg, 0.257 mmol) is saponified according to the method used for the preparation of compound 73, to give the octasaccharide 81 (593.8 mg) after flash chromatography on a column of silica gel (1/00/1 toluene/acetone).

Rf=0.57, silica gel, 2/1 toluene/acetone

Preparation of methyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O— triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-3-O-benzyl-2-benzyloxycarbonylamino-6-O-tert-butyldiphenylsilyl-2-deoxy-α-D-glucopyranoside (No. 82)

Compound 81 (130 mg, 44.3 µmol) is converted into compound 82 (164.1 mg) according to the same procedure as that described for the preparation of compound 75.

Mass: "ESI" method, negative mode: theoretical mass=4024.90; experimental mass: 4024

Preparation of methyl (methyl 2-O-ammonium sulfonato-3,4-di-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-α-2-azido-3-O-benzyl-2-deoxy-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-3-O-benzyl-2-benzyloxycarbonylamino-2-deoxy-α-D-glucopyranoside (No. 83)

To a solution of compound 82 (91.8 mg, 22.8 µmol) in methanol (3.0 mL) is added ammonium fluoride (67.6 mg, 1.82 mmol). After 48 hours of stirring at 55° C., the reaction mixture is applied to a Sephadex® LH-20 column (120×3 cm, 1/1 dichloromethane/ethanol), followed by flash chromatography on a column of silica gel (95/5 methanol/water) to give compound 83 (62.7 mg).

Rf=0.32, silica gel, 17/9/2.2/5 ethyl acetate/pyridine/acetic acid/water.

Preparation of methyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-benzyloxycarbonylamino-2-deoxy-α-D-glucopyranoside (No. 84)

To a solution of compound 83 (86 mg, 24.2 μmol) in a 1/1 tetrahydrofuran/methanol mixture (3.9 mL) is added, at 0° C., a 1 M solution of lithium hydroxide in water (780 μL). After 1 hour at 0° C. and then 16 hours at room temperature, the solution is applied to a column of Sephadex® LH-20 gel (95×2 cm) eluted with a 95/5 methanol/water mixture to give compound 84 (65.3 mg).

Rf=0.27, silica gel, 17/9/2.2/5 ethyl acetate/pyridine/acetic acid/water.

Preparation of methyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-α-D-glucopyranoside (No. 85)

Compound 84 (95.0 mg, 32.3 μmol) is treated according to the same procedure as that described for the preparation of compound 77, to give compound 85 (47.3 mg).

Mass: "ESI" method, negative mode: theoretical mass=2081.38; experimental mass: 1993.15±0.11 a.m.u. (iduronic acids observed in COOH form).

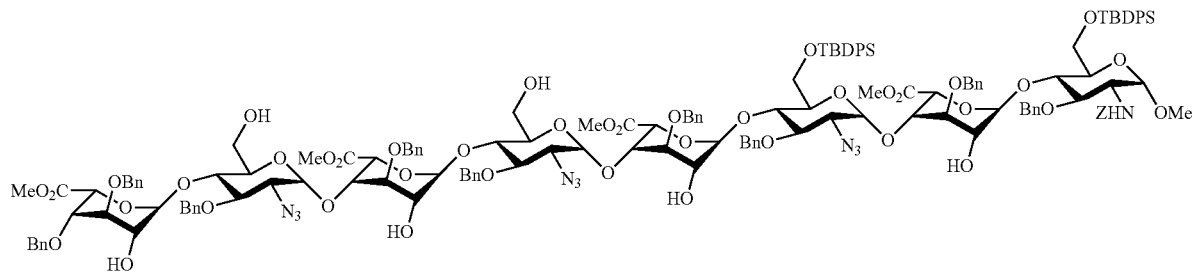

81

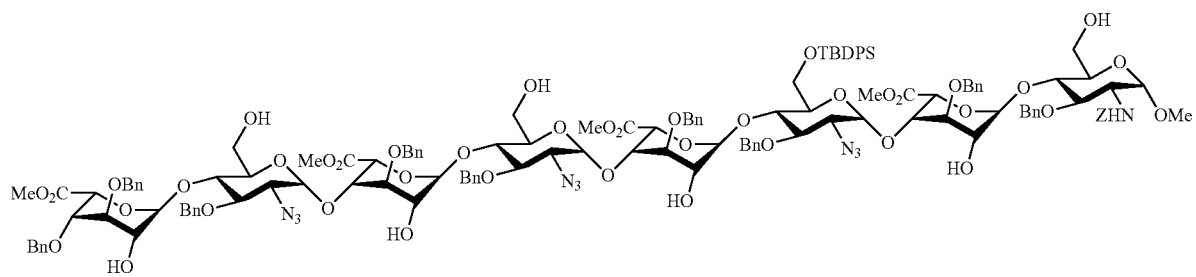

86

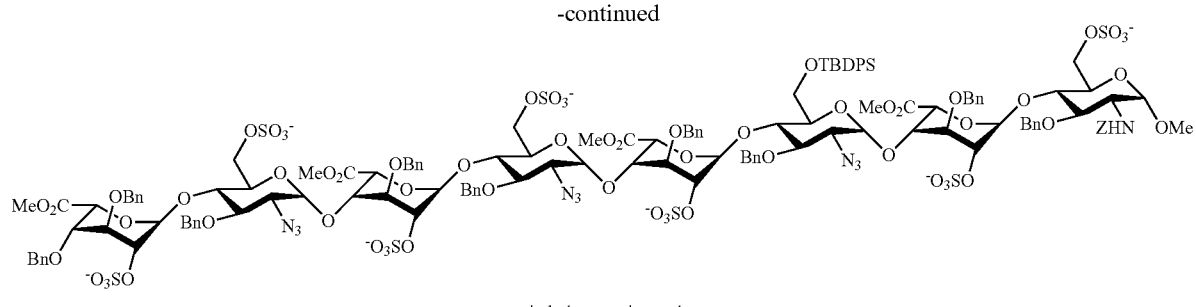
triethylammonium salt
87
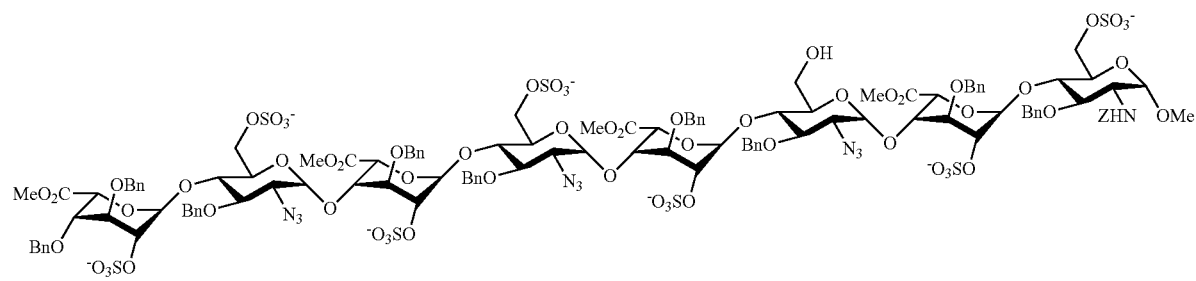
ammonium salt
88
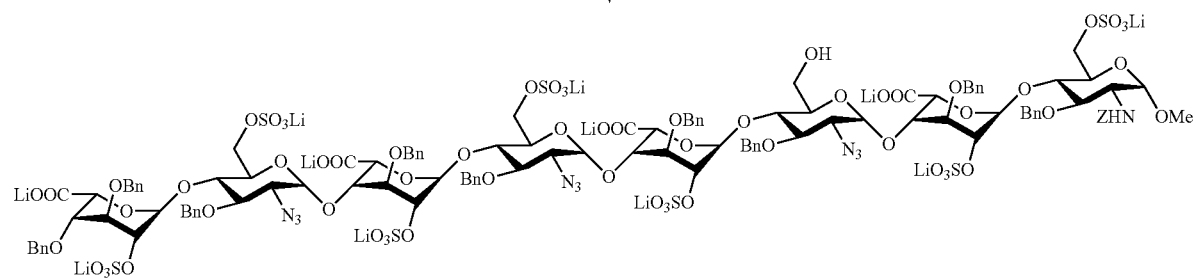
89
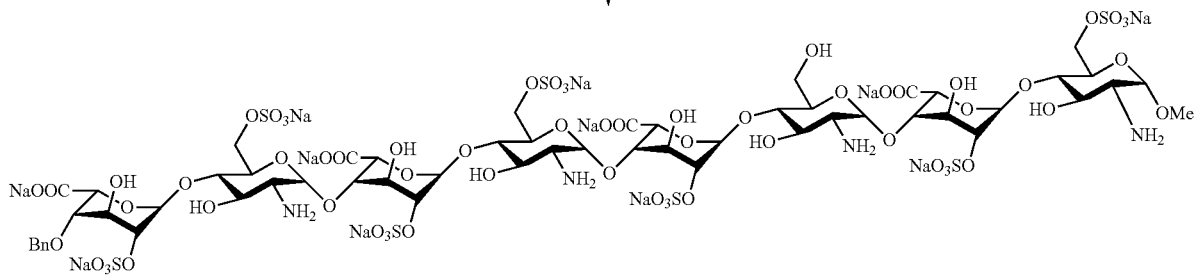
90

Preparation of methyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-3-O-benzyl-2-benzyloxycarbonylamino-2-deoxy-α-D-glucopyranoside (No. 86)

To a solution of compound 81 (50 mg, 0.017 mmol) in methanol (2.2 mL) is added ammonium fluoride (25 mg, 0.68 mmol). After 7 hours of stirring at room temperature and then 16 hours at 20° C., the reaction mixture is diluted with dichloromethane. The organic phase is washed with water, dried over sodium sulfate, filtered and then evaporated to dryness. The residue is purified by flash chromatography on a column of silica gel (100/082/18 toluene/methanol) to give 27.7 mg of compound 86.

Rf=0.16, silica gel, 85/15 toluene/methanol

Preparation of methyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-3-O-benzyl-2-benzyloxycarbonylamino-2-deoxy-6-O-triethylammonium sulfonato-α-D-glucopyranoside (No. 87)

Compound 86 (94 mg, 34.8 μmol) is treated according to the same procedure as that described for the preparation of compound 75, to give compound 87 (131.9 mg).

Rf=0.37, silica gel, 17/9/2.2/5 ethyl acetate/pyridine/acetic acid/water.

Preparation of methyl (methyl 2-O-ammonium sulfonato-3,4-di-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-6-O-ammonium sulfonato-3-O-benzyl-2-benzyloxycarbonylamino-2-deoxy-α-D-glucopyranoside (No. 88)

Compound 87 (130 mg, 32.8 μmol) is treated according to the same procedure as that described for the preparation of compound 74, to give compound 88 (102.0 mg).

Rf=0.33, silica gel, 17/9/2.2/5 ethyl acetate/pyridine/acetic acid/water.

Preparation of methyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-benzyloxycarbonylamino-2-deoxy-6-O-lithium sulfonato-α-D-glucopyranoside (No. 89)

Compound 88 (100 mg, 26.8 μmol) is treated according to the same procedure as that described for the preparation of compound 76, to give crude compound 89, which is used without further purification in the following step.

Rf=0.25, silica gel, 17/9/2.2/5 ethyl acetate/pyridine/acetic acid/water.

Preparation of methyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-6-O-sodium sulfonato-α-D-glucopyranoside (No. 90)

Crude compound 89 (75 mg, 24.8 μmol) is treated according to the same procedure as that described for the preparation of compound 77 to give compound 90 (48.2 mg).

Mass: "ESI" method, negative mode: theoretical mass=2183.42; experimental mass: 2095.07±0.24 a.m.u. (iduronic acids observed in COOH form)

69            70
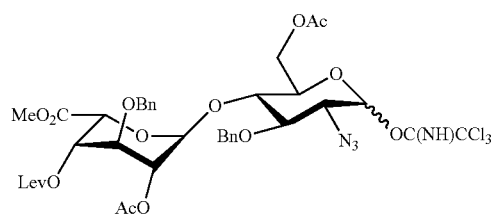
           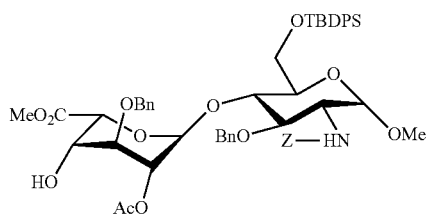
27            58
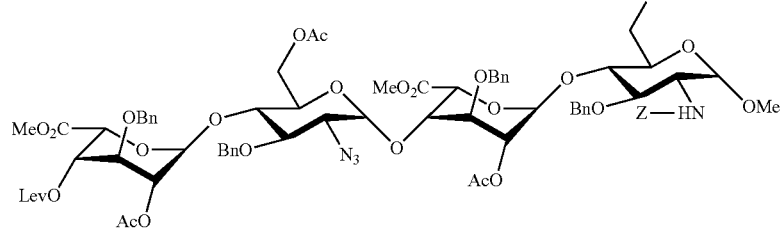
91
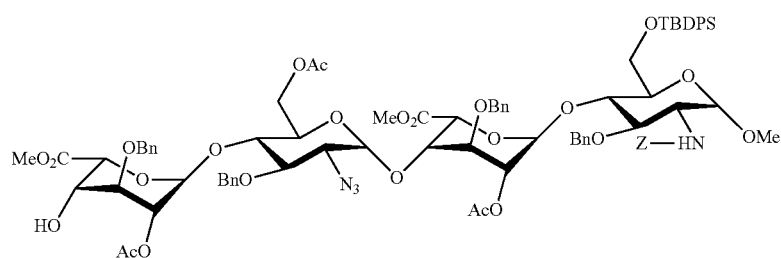
92
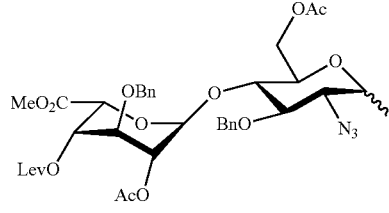
27
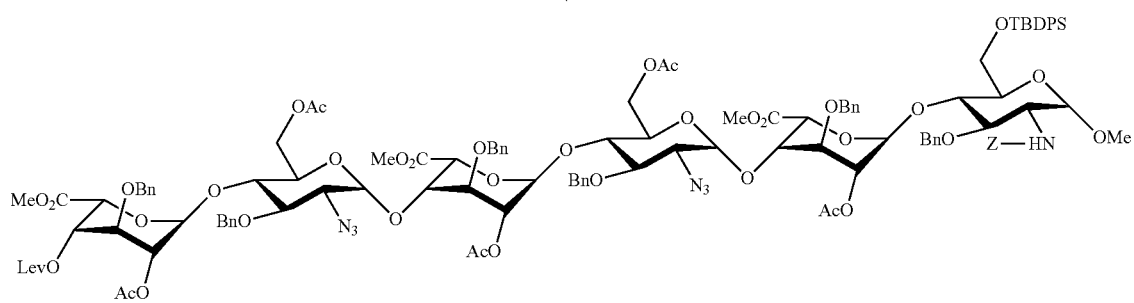
93

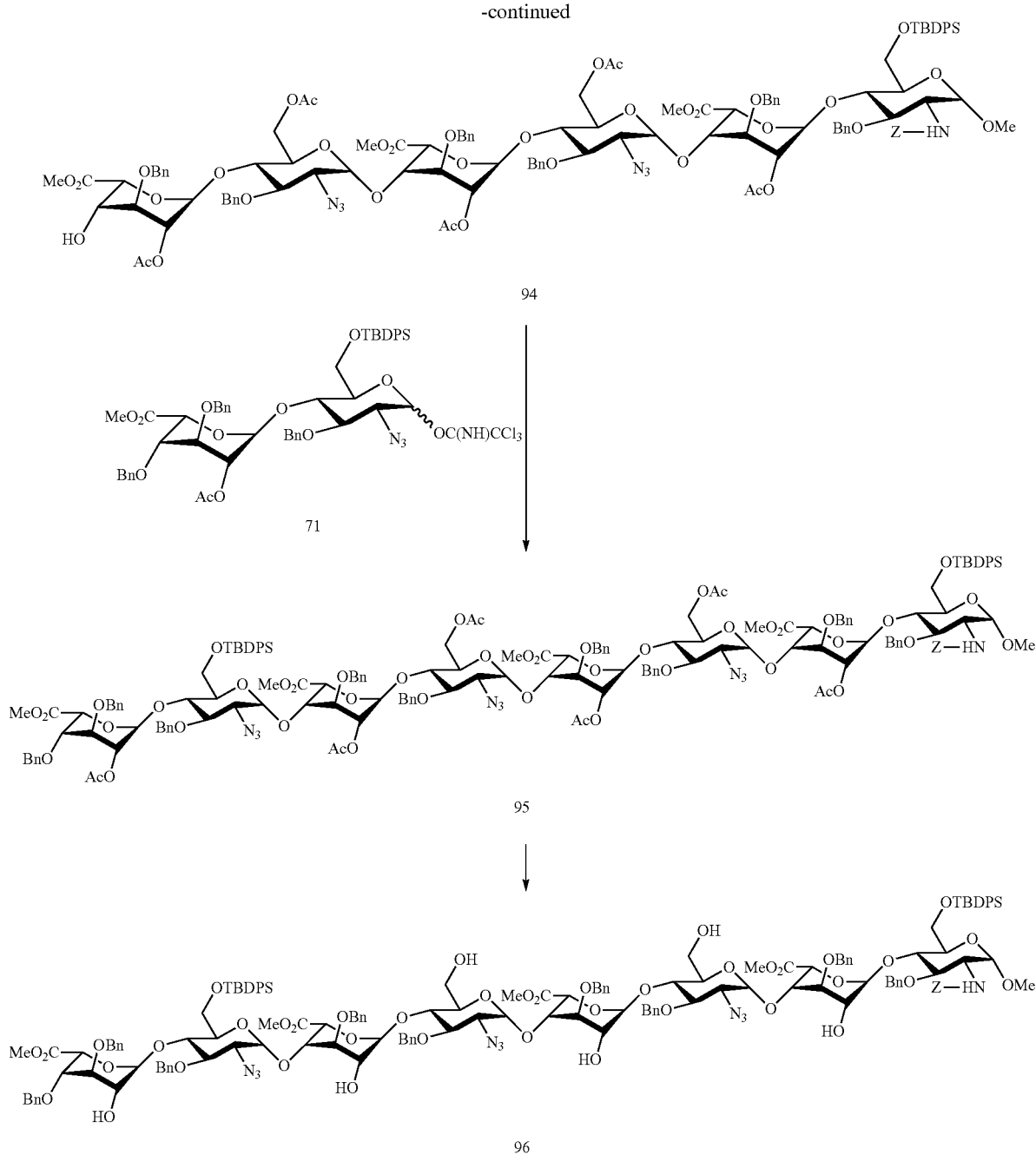

Preparation of methyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 91)

A solution of tert-butyldimethylsilyl triflate in dichloromethane (1M, 0.15 mol per mole of imidate) is added, under argon and at −20° C., to a solution of the imidate 27 (3.26 g, 3.62 mmol) and of the glycosyl acceptor 58 (3.22 g, 3.29 mmol) in dichloromethane (115 mL) in the presence of 4 Å molecular sieves (2.5 g). After 1 hour 40 minutes at −20° C. (TLC), solid sodium hydrogen carbonate is added. After filtering, washing with aqueous 2% sodium hydrogen carbonate solution, with aqueous sodium chloride solution, followed by drying (Na$_2$SO$_4$) and evaporating to dryness, the residue is purified on silica gel (toluene-acetone) to give 91 (4.66 g, 83%).

Rf=0.49 (7/3 toluene/acetone).

Preparation of methyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 92)

To a solution of compound 91 (4.66 g, 2.71 mmol) in a 1/2 mixture of toluene/ethanol (542 mL) is added hydrazine acetate (1.2 g, 5 molar equivalents). After magnetic stirring for 2 hours, the same amount of reagent is added and after 2 hours, the mixture is concentrated under vacuum and then purified on silica gel (toluene-acetone) to give compound 92 (3.83 g, 87%).

Rf=0.42 (3/1 toluene-acetone).

Preparation of methyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 93)

A solution of tert-butyldimethylsilyl triflate in dichloromethane (1M, 0.15 mol per mole of imidate) is added, under argon and at −20° C., to a solution of the imidate 27 (3.2 g, 3.55 mmol) and of the glycosyl acceptor 92 (3.83 g, 2.36 mmol) in dichloromethane (106 mL) in the presence of 4 Å molecular sieves (1.8 g). After 2.5 hours at −20° C. (TLC), solid sodium hydrogen carbonate is added. After filtering, washing with aqueous 2% sodium hydrogen carbonate solution, with aqueous sodium chloride solution, drying (Na$_2$SO$_4$) and evaporating to dryness, the residue is purified on silica gel (ethyl acetate/toluene) to give 93 (3.36 g, 61%).

Rf=0.47 (1/1 toluene/ethyl acetate).

Preparation of methyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-α-D-glucopyranoside (No. 94)

To a solution of compound 93 (3.36 g, 1.42 mmol) in a 1/2 mixture of toluene/ethanol (280 mL) is added hydrazine hydrate (0.645 g, 4.93 molar equivalents). After 2.5 hours of magnetic stirring, the mixture is concentrated under vacuum and then purified on silica gel to give compound 94 (3.01 g, 96%).

Rf=0.43 (4/1 toluene/acetone).

Preparation of methyl (methyl 2-O-acetyl-3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 95)

A 0.1 M solution of tert-butyldimethylsilyl triflate in dichloromethane (1 mL) is added, under argon and at −20° C., to a solution of the imidate 71 (0.29 g, 0.3 mmol) and of the glycosyl acceptor 94 (3.01 g, 1.33 mmol) in dichloromethane (60 mL) in the presence of 4 Å molecular sieves (0.93 g). After magnetic stirring for 10 minutes at −20° C. (TLC), imidate 71 is again added at time intervals of between 10 minutes and 2.5 hours, up to a total amount of 3.19 g. After 20 hours at −20° C. (TLC), solid sodium hydrogen carbonate is added to neutralize, and after filtering, washing with aqueous 2% sodium hydrogen carbonate solution, with aqueous sodium chloride solution, drying (Na$_2$SO$_4$) and evaporating to dryness, the residue is purified on silica gel to give 95 (2.58 g, 61%).

Rf=0.45 (4/1 toluene/acetone).

Preparation of methyl (methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-6-O-tert-butyldiphenylsilyl-2-deoxy-2-[(benzyloxy)carbonyl]-amino-α-D-glucopyranoside (No. 96)

To a solution of 95 (1.18 g, 0.37 mmol) in a 3/2 mixture of methanol/dichloromethane (111 mL) is added a 1M a methanolic solution of sodium methoxide (1.1 mL), in the presence of 3 Å molecular sieves (463 mg). After stirring for 20 hours at room temperature, the mixture is neutralized with H$^+$ Dowex 50WX4 resin. After filtering and concentrating, the residue is purified on silica gel with a toluene/acetone mixture to give compound 96 (773 mg, 77%).

Rf=0.51 (4/1 toluene/acetone).

75 76
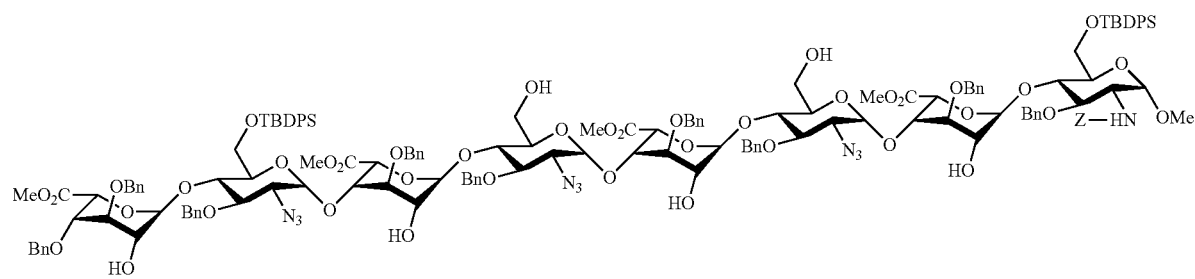
96
triethylammonium salt
97
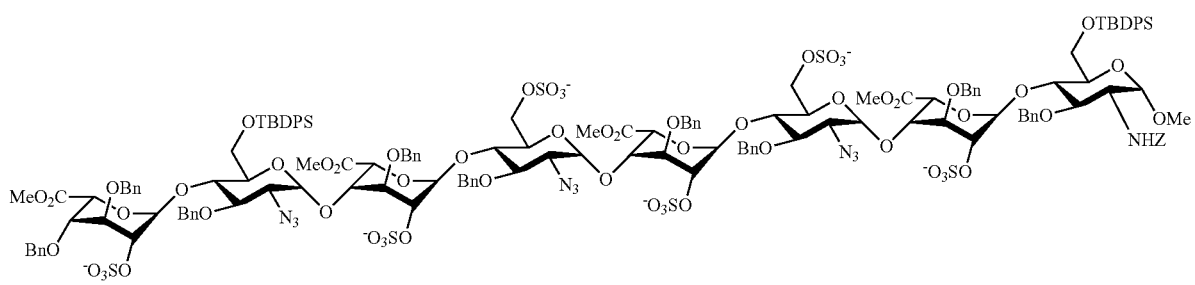
ammonium salt
98

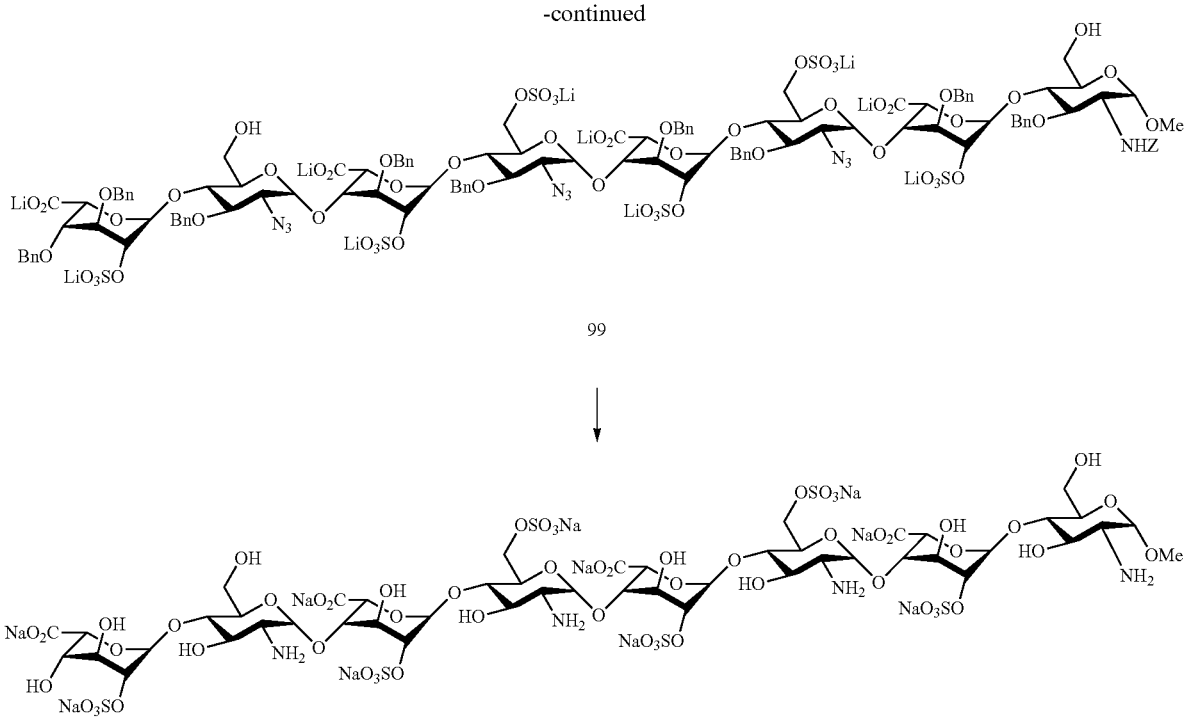

99

↓

100

Preparation of methyl (methyl 3,4-di-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 97)

Triethylamine/sulfur trioxide complex (761 mg, 5 mol per hydroxyl function) is added to a solution in N,N-dimethylformamide (11 mL, 90 L/mol) of compound 96 (324 mg, 120 μmol). After 17 hours of magnetic stirring at 55° C. sheltered from light, methanol is added at 0° C. and, after stirring for 30 minutes at 0° C. and then for 30 minutes at room temperature, the reaction medium is diluted with methanol and then purified by means of an LH-20 column, using a 1/1 mixture of methanol/dichloromethane as eluent. The fractions containing the product are then concentrated under high vacuum and, if necessary, reacted again under the same conditions. Compound 97 obtained is then used directly in the following step.

Rf=0.5 (11/7/1.6/4 EtOAc/pyridine/AcOH/H₂O).

Preparation of methyl (methyl 2-O-ammonium sulfonato-3,4-di-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-3-O-benzyl-2-deoxy-2-[(benzyloxy)carbonyl]amino-α-D-glucopyranoside (No. 98)

To a solution of compound 97 obtained previously in methanol (16 mL) is added ammonium fluoride (361 mg, 80 molar equivalents). After magnetic stirring at 55° C. for 48 hours, the reaction mixture is purified with the aid of an LH-20 column, using a 75/20/5 mixture of methanol/N,N-dimethylformamide/water as eluent. The fractions containing the product are then concentrated under high vacuum to give compound 98 (410 mg, 95%, 2 steps).

Rf=0.28 (57/29/7.2/16 EtOAc/pyridine/AcOH/H₂O).

Preparation of methyl (lithium 3,4-di-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-α-D-glucopyranoside (No. 99)

To a solution of compound 98 (202 mg, 57 μmol) in a 1/1 mixture of methanol/tetrahydrofuran (9 mL) is added, dropwise and at 0° C., aqueous 1N LiOH solution (1.8 mL, 7.9 equivalents/methyl ester function). After stirring for 1 hour at 0° C., and then for 16 hours at room temperature, the reaction medium is purified by means of an LH-20 column, using a 75/20/5 mixture of methanol/N,N-dimethylformamide/water as eluent. The fractions containing the product are then concentrated under high vacuum to give the desired compound 99, which is used directly in the following step.

Rf=0.41 (57/29/7.2/16 EtOAc/pyridine/AcOH/H$_2$O)

Preparation of methyl (lithium 2-O-lithium sulfonato-α-L-idopyranosyluronate)-(1→4)-(2-amino-2-deoxy-α-D-glucopyranosyl)-(1→4)-(lithium 2-O-lithium sulfonato-α-L-idopyranosyluronate)-(1→4)-(2-amino-2-deoxy-6-O-lithium sulfonato-α-D-glucopyranosyl)-(1→4)-(lithium 2-O-lithium sulfonato-α-L-idopyranosyluronate)-(1→4)-(2-amino-2-deoxy-6-O-lithium sulfonato-α-D-glucopyranosyl)-(1→4)-(lithium 2-O-lithium sulfonato-α-L-idopyranosyluronate)-(1→4)-2-amino-2-deoxy-α-D-glucopyranoside (No. 100)

To a solution in a 1/1 mixture of tert-butanol/water (13 mL) of compound 99 obtained previously are successively added ammonium formate (529 mg, 8.4 mmol) and then 10% Pd/C (1.24 g). After 4 hours 15 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 100 (78 mg, 66%, 2 steps).

Mass: "ESI" method, negative mode: theoretical mass=1992.8; experimental mass [M−Na−H]: 1971.03±0.10 a.m.u. (iduronic acids observed in COOH form).

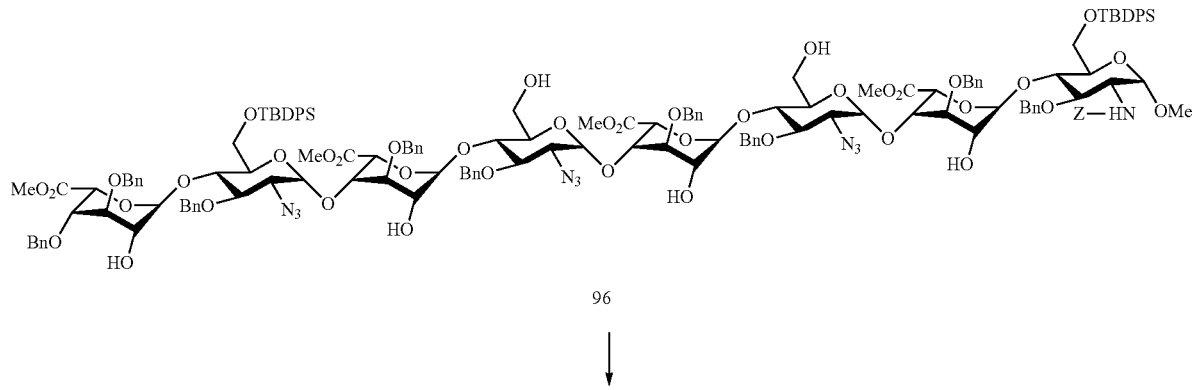

96

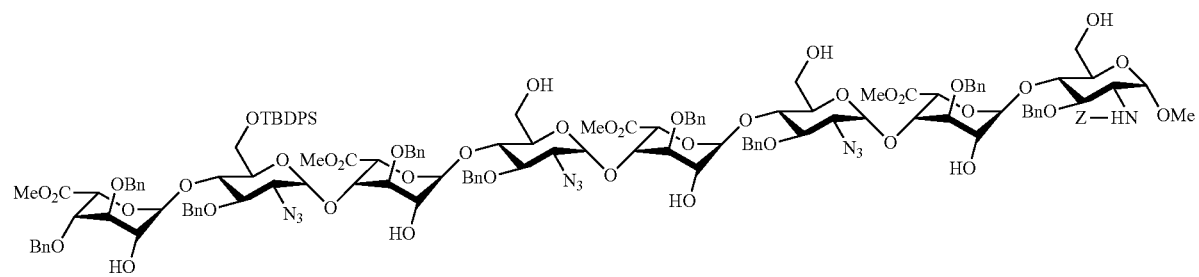

101

-continued
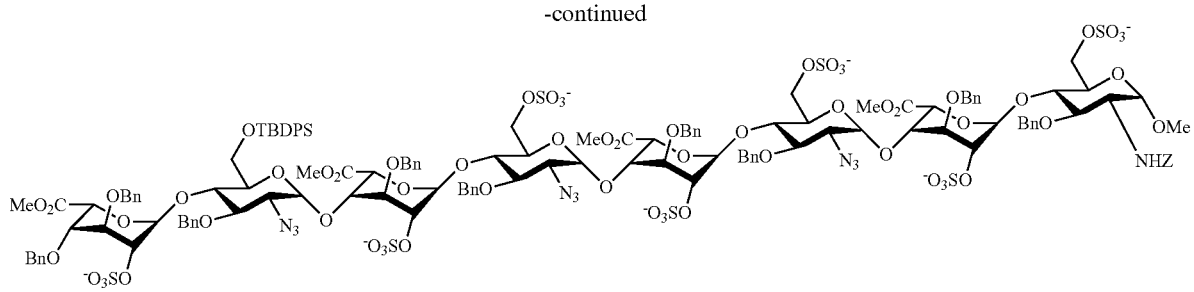
triethylammonium salt
102
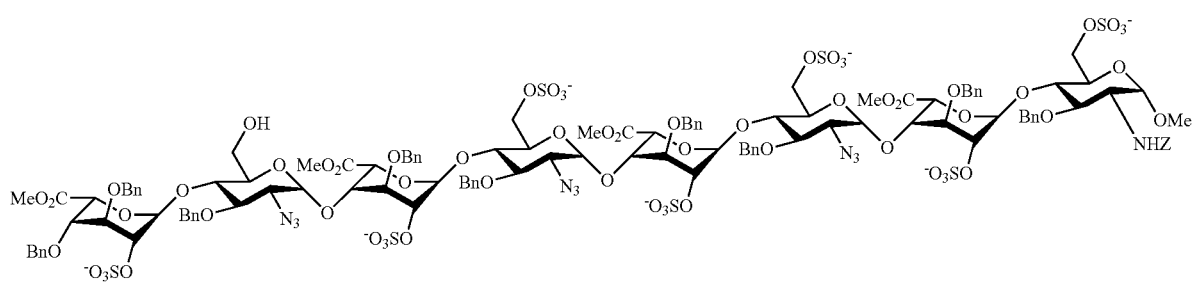
ammonium salt
103
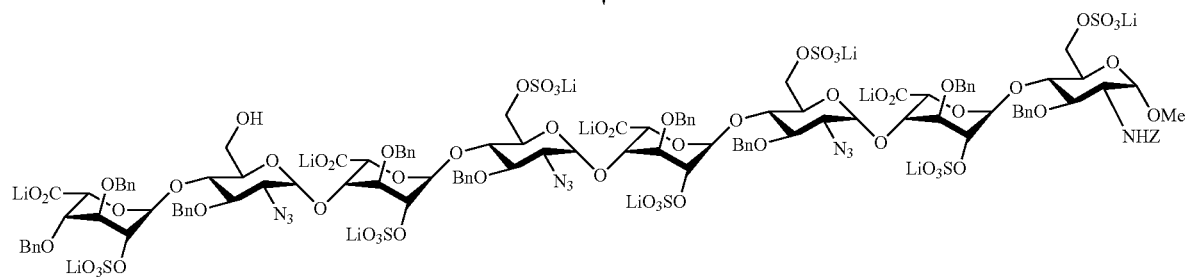
104
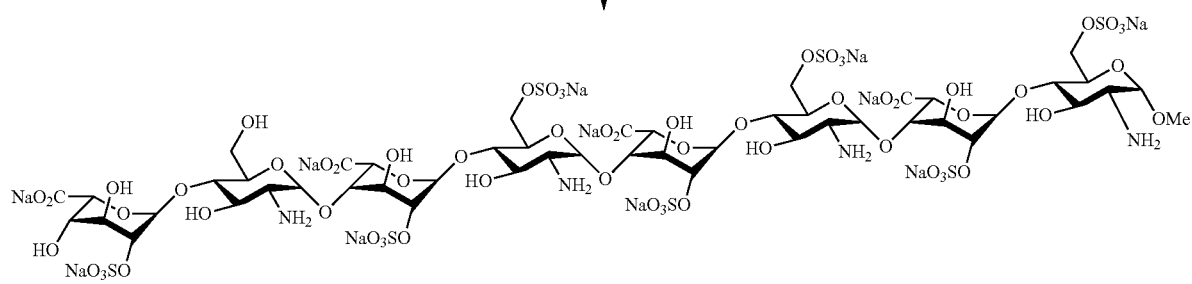
105

Preparation of methyl (methyl 3,4-di-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-deoxy-2-[(benzyloxy)carbonyl]amino-α-D-glucopyranoside (No. 101)

To a solution of compound 96 (570 mg, 194 μmol) in methanol (66 mL) is added ammonium fluoride (575 mg, 80 molar equivalents). After magnetic stirring at room temperature for 14 hours, the reaction mixture is concentrated under vacuum and then purified on a column of silica (toluene/acetone) to give compound 101 (282 mg, 54%).

Rf=0.37 (7/3 toluene/acetone).

Preparation of methyl (methyl 3,4-di-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-α-D-glucopyranoside (No. 102)

Triethylamine/sulfur trioxide complex (376 mg, 5 mol per hydroxyl function) is added to a solution in N,N-dimethylformamide (5.3 mL, 90 L/mol) of compound 101 (160 mg, 59 μmol). After 17 hours of magnetic stirring at 55° C. sheltered from light, methanol is added at 0° C. and, after stirring for 30 minutes at 0° C. and then for 30 minutes at room temperature, the reaction medium is diluted with methanol and then purified by means of an LH-20 column, using a 1/1 mixture of ethanol/dichloromethane as eluent. The fractions containing the product are then concentrated under high vacuum. The compound obtained is then used directly in the following step.

Rf=0.52 (11/7/1.6/4 EtOAc/pyridine/AcOH/H$_2$O).

Preparation of methyl (methyl 2-O-ammonium sulfonato-3,4-di-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-6-O-ammonium sulfonato-3-O-benzyl-2-deoxy-2-[(benzyloxy)carbonyl]amino-α-D-glucopyranoside (No. 103)

To a solution of compound 102 obtained previously in methanol (2.5 mL) is added ammonium fluoride (42 mg, 60 molar equivalents). After magnetic stirring at room temperature for 3 hours, at 45° C. for 18 hours, and then at 55° C. for 4 hours, ammonium fluoride (14 mg, 20 molar equivalents) is again added, and the reaction mixture is stirred for 24 hours at 55° C. and then at room temperature for 60 hours. The reaction mixture is then purified by means of an LH-20 column, using a 75/20/5 mixture of methanol/N,N-dimethylformamide/water as eluent. The fractions containing the product are then concentrated under high vacuum to give compound 103 (35 mg, 54%).

Rf=0.54 (11/7/1.6/4 EtOAc/pyridine/AcOH/H$_2$O).

Preparation of methyl (lithium 3,4-di-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-6-O-lithium sulfonato-α-D-glucopyranoside (No. 104)

To a solution of compound 103 (155 mg, 41.6 μmol) in a 1/1 mixture of methanol/tetrahydrofuran (7 mL) is added, dropwise and at 0° C., aqueous 1N LiOH solution (1.4 mL, 8.4 equivalents/methyl ester function). After stirring for 1 hour at 0° C. and then for 15 hours at room temperature, the reaction medium is purified by means of an LH-20 column, using a 95/5 methanol/water mixture as eluent. The fractions containing the product are then concentrated under high vacuum to give the desired compound 104 (114 mg, 90%).

Rf=0.25 (11/7/1.6/4 EtOAc/pyridine/AcOH/H$_2$O).

Preparation of methyl (sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-2-amino-2-deoxy-6-O-sodium sulfonato-α-D-glucopyranoside (No. 105)

To a solution in a 1/1 mixture of tert-butanol/water (8 mL) of compound 104 (110 mg, 36 μmol) are successively added ammonium formate (298 mg, 4.72 mmol) and then 10% Pd/C (715 mg). After 4 hours 15 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 105 (63 mg, 80%).
Chemical shifts of the anomeric protons (600 MHz, D$_2$O) δ 5.08 IdoUA$^{VIII}$, 5.23* Glc$^{VIII}$, 5.14 IdoUA$^{VI}$, 5.24* Glc$^{V}$, 5.14 IdoUA$^{IV}$, 5.24* Glc$^{III}$, 5.14 IdoUA$^{II}$, 4.73 Glc$^{I}$
*: The signals may be interchanged.
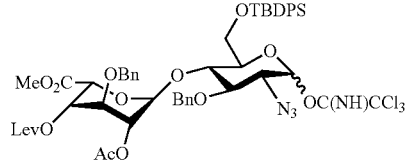
63
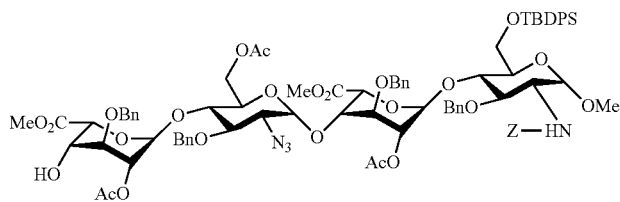
92
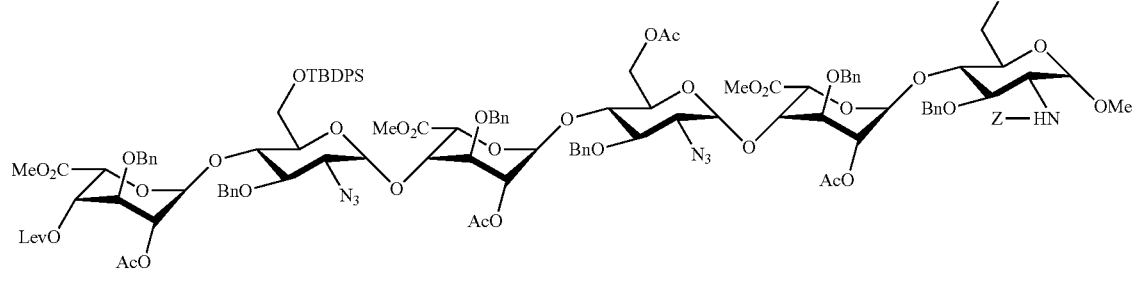
106
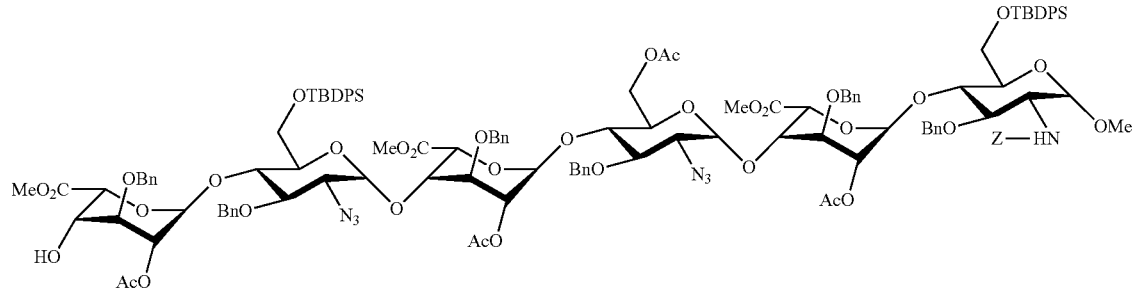
107
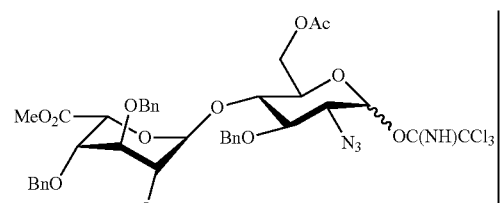
38

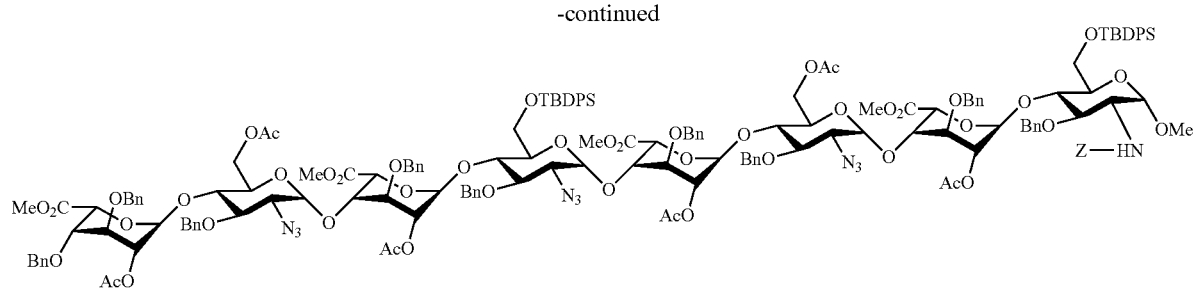

108

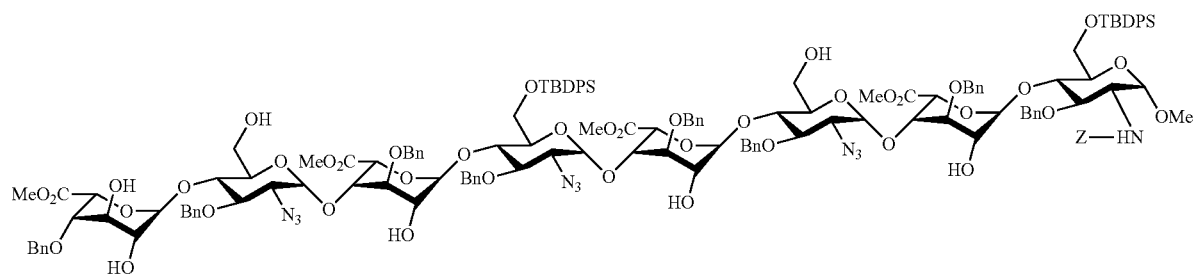

109

Preparation of methyl (methyl 2-O-acetyl-3-O-benzyl-4-O-levulinoyl-α-L-idopyranosyluronate)-(1→4)-(2-azido-3-O-benzyl-2-deoxy-6-O-tert-butyldiphenylsilyl-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 106)

A solution of tert-butyldimethylsilyl triflate (1M, 0.2 mol per mole of imidate) in dichloromethane is added, under argon and at −15° C., to a solution of the imidate 63 (0.59 g, 0.54 mmol) and of the glycosyl acceptor 92 (0.58 g, 0.36 mmol) in dichloromethane (25 mL) in the presence of 4 Å molecular sieves (0.4 g). After 45 minutes at −15° C. (TLC), further imidate 63 (0.39 g, 0.35 mmol) is added, followed by addition of tert-butyldimethylsilyl triflate in dichloromethane (1M, 1.1 mL). After 1 hour 10 minutes at −15° C. (TLC), solid sodium hydrogen carbonate is added to neutralize. After filtering, washing with aqueous 2% sodium hydrogen carbonate solution, drying ($Na_2SO_4$) and evaporating to dryness, the residue is purified by means of an LH-20 column, using a 1/1 ethanol/dichloromethane mixture as eluent. The fractions containing the product are then concentrated under high vacuum and the residue is then purified on silica gel (ethyl acetate/toluene) to give 106 (0.69 g, 75%).

Rf=0.16 (9/1 toluene/acetone).

Preparation of methyl (methyl 2-O-acetyl-3-O-benzyl-α-L-idopyranosyluronate)-(1→4)-(2-azido-3-O-benzyl-2-deoxy-6-O-tert-butyldiphenylsilyl-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 107)

To a solution of compound 106 (1.41 g, 0.552 mmol) in a 1/2 mixture of toluene/ethanol (110 mL) is added hydrazine acetate (0.254 g, 2.76 molar equivalents). After 2 hours 40 minutes of magnetic stirring, the mixture is concentrated under vacuum and then purified on silica gel to give compound 107 (1.15 g, 85%).

Rf=0.16 (9/1 toluene/acetone).

Preparation of methyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-2-deoxy-6-O-tert-butyldiphenylsilyl-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-α-D-glucopyranoside (No. 108)

A 0.1 M solution of tert-butyldimethylsilyl triflate in dichloromethane (1.1 mL) is added, under argon and at −20°

C., to a solution of the imidate 38 (0.67 g, 0.75 mmol) and of the glycosyl acceptor 107 (1.23 g, 0.49 mmol) in dichloromethane (32 mL) in the presence of 4 Å molecular sieves (0.55 g). After 1.5 hours at −20° C. (TLC), solid sodium hydrogen carbonate is added to neutralize, and after filtering, washing with aqueous 2% sodium hydrogen carbonate solution, drying (Na$_2$SO$_4$) and evaporating to dryness, the residue is purified by means of an LH-20 column, using a 1/1 ethanol/dichloromethane mixture as eluent. The fractions containing the product are then concentrated under high vacuum and the residue is then purified on silica gel to give 108 (0.93 g, 59%).

Rf=0.24 (7/3 cyclohexane/acetone).

Preparation of methyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-6-O-tert-butyldiphenylsilyl-2-deoxy-2-[(benzyloxy)carbonyl]-amino-α-D-glucopyranoside (No. 109)

To a solution of 108 (1.17 g, 0.36 mmol) in a 3/2 mixture of methanol/dichloromethane (109 mL) is added a 1M a methanolic solution of sodium methoxide (1.6 mL), in the presence of 3 Å molecular sieves (458 mg). After stirring for 18 hours at room temperature, the mixture is neutralized with H$^+$ Dowex 50WX4 resin. After filtering and concentrating, the residue is purified on silica gel with a cyclohexane/ethyl acetate mixture to give compound 109 (680 mg, 69%).

Rf=0.34 (7/3 toluene/acetone).

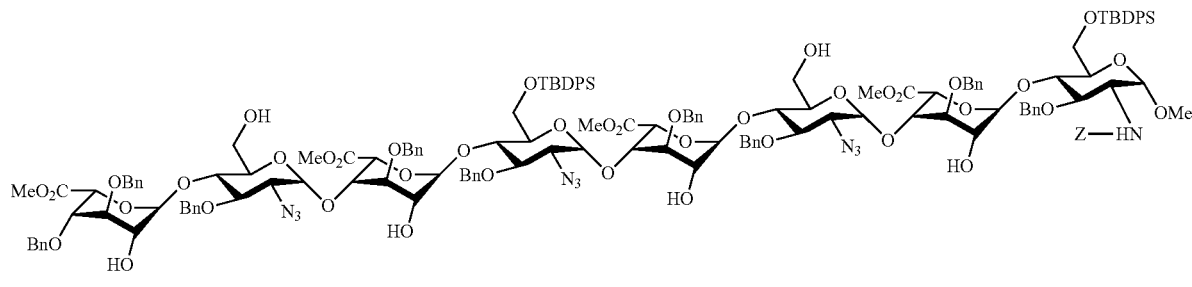

109

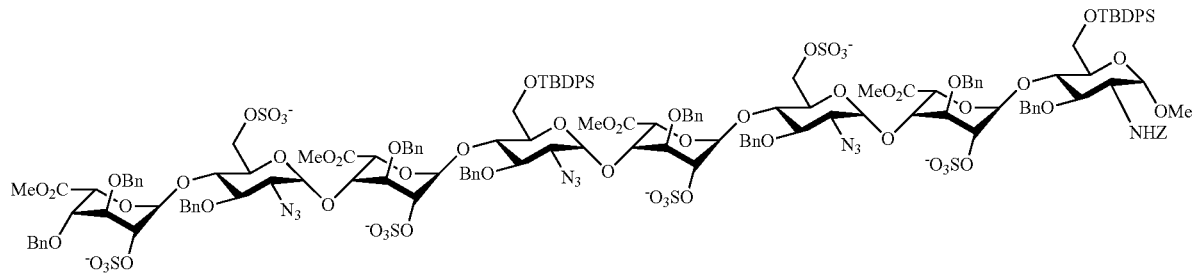

triethylammonium salt

110

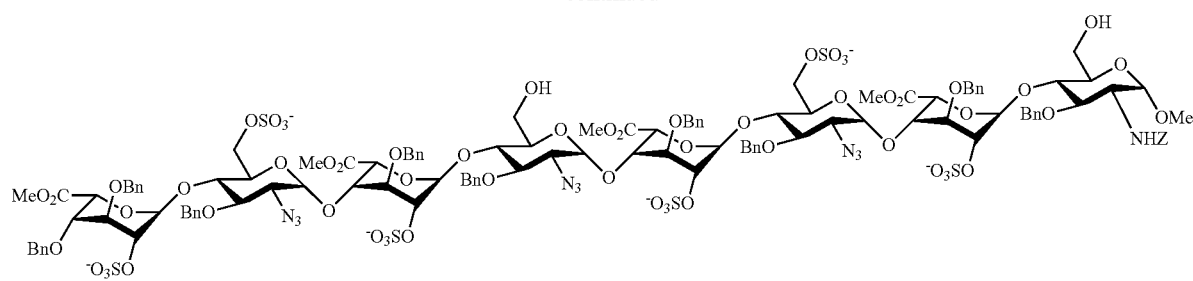
ammonium salt
111
112
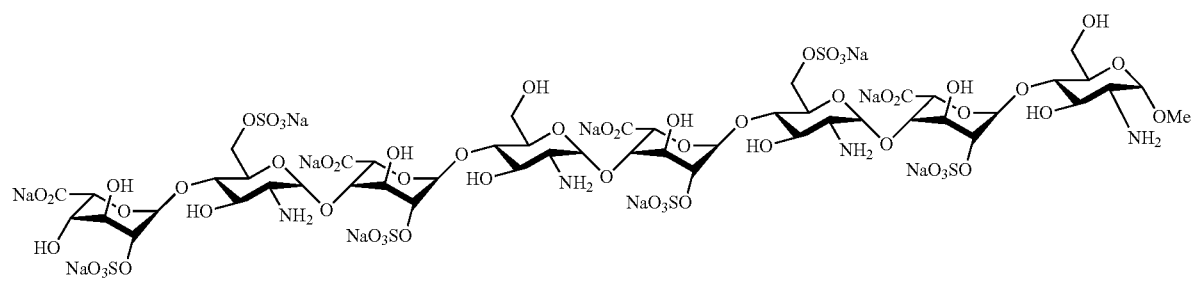
113

Preparation of methyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]-amino-6-O-tert-butyldiphenylsilyl-α-D-glucopyranoside (No. 110)

Triethylamine/sulfur trioxide complex (267 mg, 5 mol per hydroxyl function) is added to a solution in N,N-dimethylformamide (4.4 mL, 90 L/mol) of compound 109 (144 mg, 49 µmol). After 16 hours of magnetic stirring at 55° C. sheltered from light, methanol is added at 0° C. and, after stirring for 30 minutes at 0° C. and then for 30 minutes at room temperature, the reaction medium is diluted with methanol and then purified by means of an LH-20 column, using a 1/1 mixture of methanol/dichloromethane as eluent. The fractions containing the product are then concentrated under high vacuum. The compound obtained is then used directly in the following step.

Rf=0.42 (57/29/7.2/16 EtOAc/pyridine/AcOH/H$_2$O).

Preparation of methyl (methyl 3,4-di-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyl uronate)-(1→4)-3-O-benzyl-2-deoxy-2-[(benzyloxy)carbonyl]amino-α-D-glucopyranoside (No. 111)

To a solution of compound 110 obtained previously in methanol (5 mL) is added ammonium fluoride (133 mg, 80 molar equivalents). After magnetic stirring at 55° C. for 48 hours, the reaction mixture is purified with the aid of an LH-20 column using a 95/5 methanol/water mixture as eluent. The fractions containing the product are then concentrated under high vacuum. If necessary, the crude reaction product is used and treated again under the same conditions to give compound III (117 mg, 85%, 2 steps).

Rf=0.31 (57/29/7.2/16 EtOAc/pyridine/AcOH/H$_2$O).

Preparation of methyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]amino-α-D-glucopyranoside (No. 112)

To a solution of compound III (80 mg, 22.3 µmol) in a 1/1 mixture of methanol/tetrahydrofuran (3.6 mL) is added, dropwise and at 0° C., aqueous 1N LiOH solution (0.7 mL, 7.8 equivalents/methyl ester function). After 2 hours 45 minutes of stirring at 0° C., and then 17.5 hours at room temperature, the reaction medium is purified by means of an LH-20 column, using a 75/20/5 mixture of methanol/N,N-dimethylformamide/water as eluent. The fractions containing the product are then concentrated under high vacuum to give the desired compound 112 (64 mg, 98%).

Rf=0.25 (56/32/7.6/18 EtOAc/pyridine/AcOH/H$_2$O).

Preparation of methyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-2-amino-2-deoxy-α-D-glucopyranoside (No. 113)

To a solution in a 1/1 mixture of tert-butanol/water (4.3 mL) of compound 112 (64 mg, 21.7 µmol) are successively added ammonium formate (178 mg, 2.8 mmol) and then 10% Pd/C (0.42 g). After 4 hours 30 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 113 (29.5 mg, 65%).

Chemical shifts of the anomeric protons (600 MHz, D$_2$O) δ 5.18 IdoUA$^{VIII}$, 5.43 Glc$^{VII}$, 5.24 IdoUA$^{VI}$, 5.45 Glc$^{V}$, 5.25 IdoUA$^{IV}$, 5.43 Glc$^{III}$, 5.26 IdoUA$^{II}$, 5.01 Glc$^{I}$

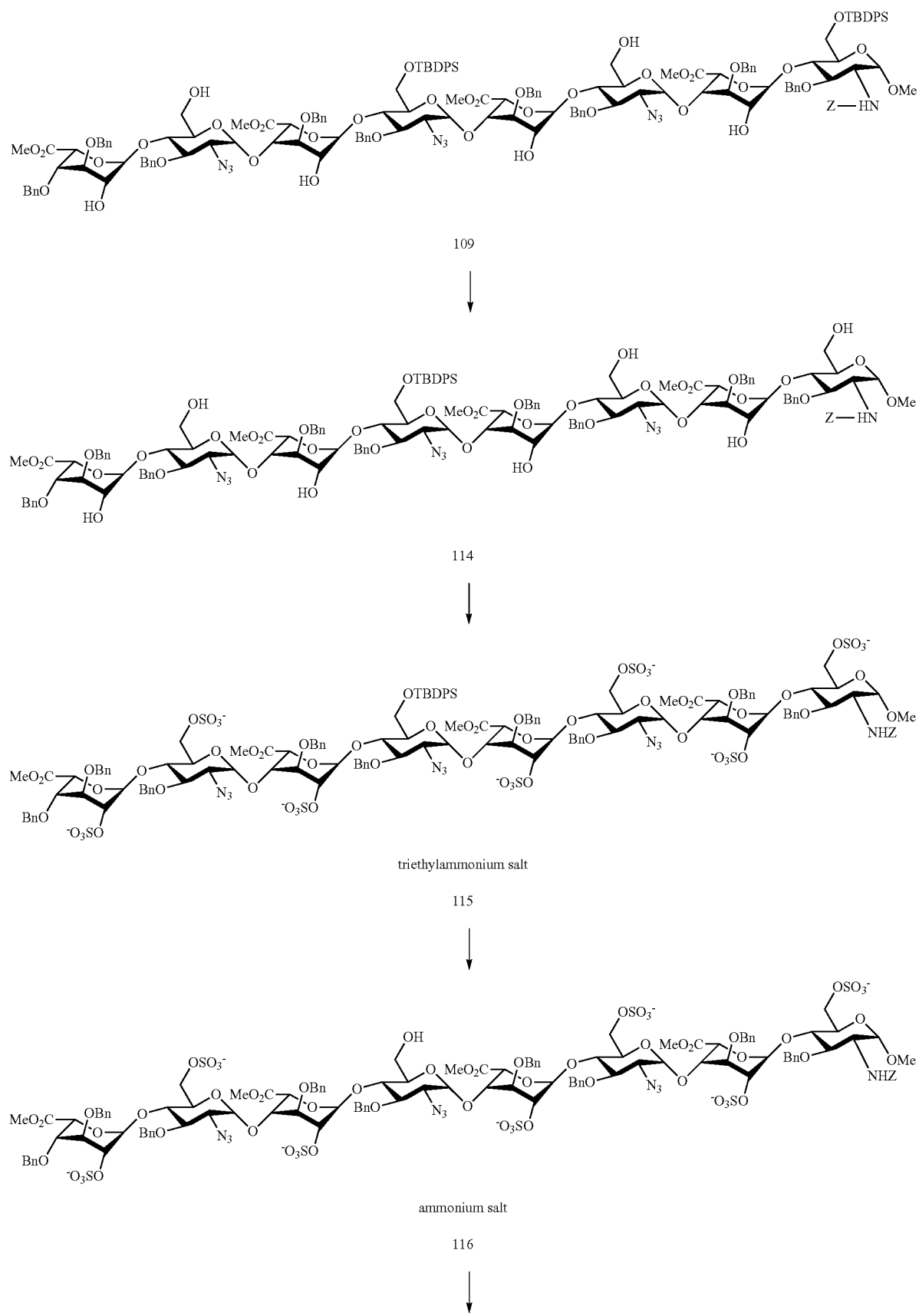

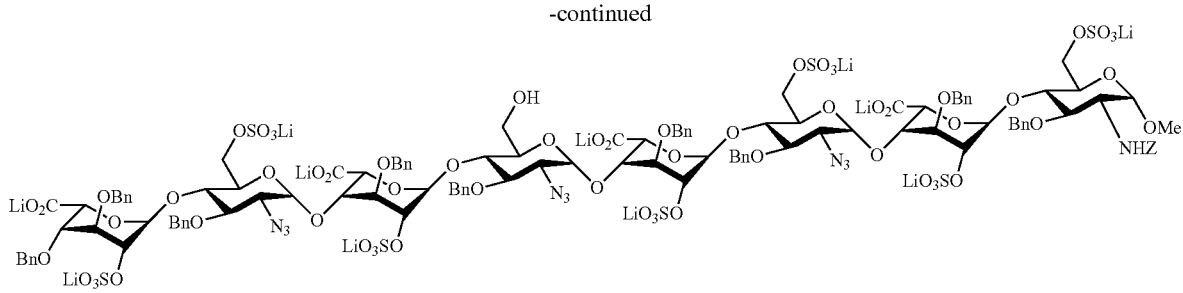

117

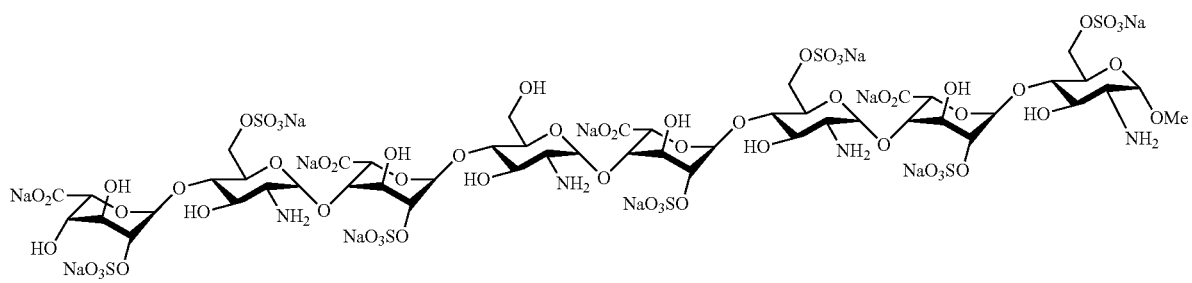

118

Preparation of methyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-3-O-benzyl-2-deoxy-2-[(benzyloxy)carbonyl]amino-α-D-glucopyranoside (No. 114)

To a solution of compound 109 (135 mg, 46 μmol) in methanol (16 mL) is added ammonium fluoride (136 mg, 80 molar equivalents). After magnetic stirring at room temperature for 9 hours, and then at −25° C. for 15 hours, the reaction mixture is concentrated under vacuum and then purified on a column of silica (toluene/acetone) to give compound 114 (57 mg, 46%).

Rf=0.30 (toluene-methanol 85/15).

Preparation of methyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-3-O-benzyl-2-deoxy-2-[(benzyloxy)carbonyl]amino-6-O-triethylammonium sulfonato-α-D-glucopyranoside (No. 115)

Triethylamine/sulfur trioxide complex (317 mg, 5 mol per hydroxyl function) is added to a solution in N,N-dimethylformamide (4.5 mL, 90 L/mol) of compound 114 (135 mg, 50 μmol). After 16 hours of magnetic stirring at 55° C. sheltered from light, methanol is added at 0° C. and, after stirring for 30 minutes at 0° C. and then for 30 minutes at room temperature, the reaction medium is diluted with methanol and then purified by means of an LH-20 column, using a 1/1 mixture of ethanol/dichloromethane as eluent. The fractions containing the product are then concentrated under high vacuum. Compound 115 (168 mg, 86%) is then obtained.

Rf=0.29 (56/32/7.6/18 EtOAc/pyridine/AcOH/H$_2$O).

Preparation of methyl (methyl 2-O-ammonium sulfonato-3,4-di-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-(6-O-ammonium sulfonato-2-azido-3-O-benzyl-2-deoxy-α-D-glucopyranosyl)-(1→4)-(methyl 2-O-ammonium sulfonato-3-O-benzyl-α-L-idopyranosyluronate)-(1→4)-6-O-ammonium sulfonato-3-O-benzyl-2-deoxy-2-[(benzyloxy)carbonyl]amino-α-D-glucopyranoside (No. 116)

To a solution of compound 115 (168 mg, 43 μmol) in methanol (5.6 mL) is added ammonium fluoride (128 mg, 80 molar equivalents). After magnetic stirring at 55° C. for 48 hours, the reaction mixture is purified with the aid of an LH-20 column using a 95/5 methanol/water mixture as eluent. If necessary, the residue may be used under the same conditions, while monitoring the reaction progress (TLC), and may be purified in the same manner. The fractions containing the product are then concentrated under high vacuum to give compound 116 (109 mg, 81%).

Rf=0.21 (56/32/7.6/18 EtOAc/pyridine/AcOH/H$_2$O).

Preparation of methyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]-amino-6-O-lithium sulfonato-α-D-glucopyranoside (No. 117)

To a solution of compound 116 (89 mg, 28.5 μmol) in a 1/1 mixture of methanol/tetrahydrofuran (3.8 mL) is added, dropwise and at 0° C., aqueous 1N LiOH solution (0.7 mL). After stirring for 3 hours at 0° C., and then for 19 hours at room temperature, the reaction medium is purified by means of an LH-20 column, using a 75/20/5 mixture of methanol/N,N-dimethylformamide/water as eluent. The fractions containing the product are then concentrated under high vacuum and if necessary, the reaction is repeated and then worked up in the same manner to give the desired compound 117 (70 mg, 81%).

Rf=0.12 (56/32/7.6/18 EtOAc/pyridine/AcOH/H$_2$O).

Preparation of methyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-2-amino-2-deoxy-6-O-sodium sulfonato-α-D-glucopyranoside (No. 118)

To a solution in a 1/1 mixture of tert-butanol/water (2.3 mL) of compound 117 (35 mg, 11.6 μmol) are successively added ammonium formate (95 mg, 1.51 mmol) and then 10% Pd/C (229 mg). After 4 hours 30 minutes of vigorous stirring at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 118 (11.1 mg, 45%).

Chemical shifts of the anomeric protons (600 MHz, D$_2$O) δ 5.17 IdoUA$^{VIII}$, 5.42 Glc$^{VII}$, 5.25 IdoUA$^{VI}$, 5.45 Glc$^{V}$, 5.24 IdoUA$^{IV}$, 5.44 Glc$^{III}$, 5.26 IdoUA$^{II}$, 5.03 Glc$^{I}$

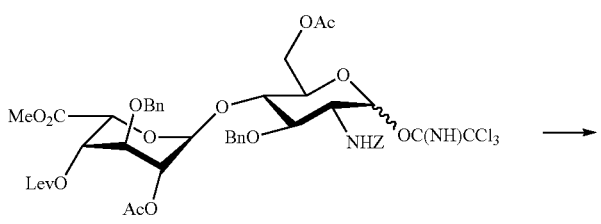

24

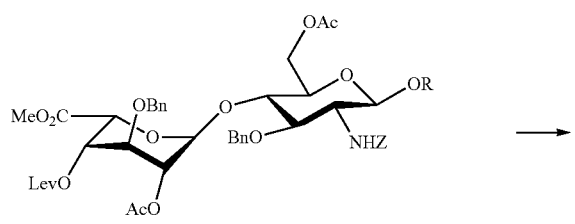

119: R = (CH$_2$)$_5$Ph
120: R = CH$_2$CHPr$_2$
121: R = (CH$_2$)$_3$C$_6$H$_{11}$
122: R = (CH$_2$)$_2$CHPh$_2$

-continued
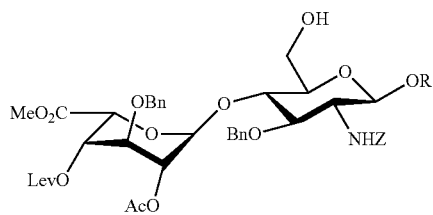
123: R = (CH$_2$)$_5$Ph
124: R = CH$_2$CHPr$_2$
125: R = (CH$_2$)$_3$C$_6$H$_{11}$
126: R = (CH$_2$)$_2$CHPh$_2$
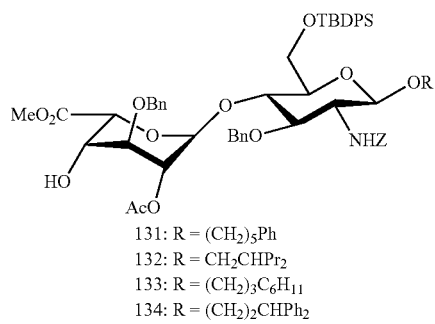
131: R = (CH$_2$)$_5$Ph
132: R = CH$_2$CHPr$_2$
133: R = (CH$_2$)$_3$C$_6$H$_{11}$
134: R = (CH$_2$)$_2$CHPh$_2$
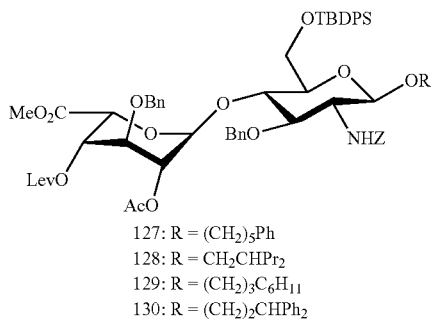
127: R = (CH$_2$)$_5$Ph
128: R = CH$_2$CHPr$_2$
129: R = (CH$_2$)$_3$C$_6$H$_{11}$
130: R = (CH$_2$)$_2$CHPh$_2$
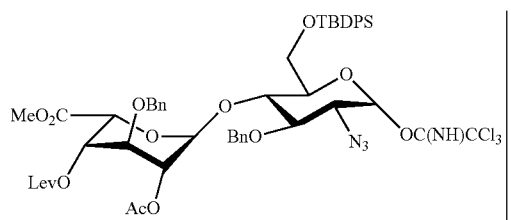
63
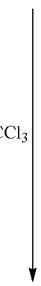
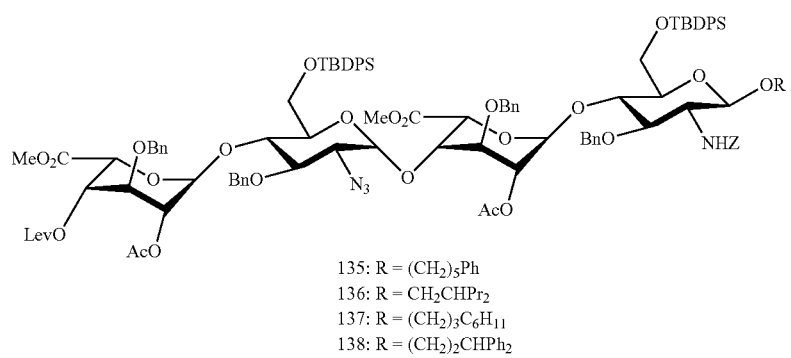
135: R = (CH$_2$)$_5$Ph
136: R = CH$_2$CHPr$_2$
137: R = (CH$_2$)$_3$C$_6$H$_{11}$
138: R = (CH$_2$)$_2$CHPh$_2$

-continued

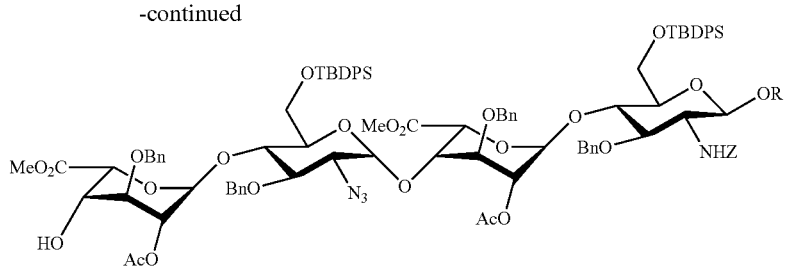

139: R = (CH$_2$)$_5$Ph
140: R = CH$_2$CHPr$_2$
141: R = (CH$_2$)$_3$C$_6$H$_{11}$
142: R = (CH$_2$)$_2$CHPh$_2$

Preparation of 5-phenylpentyl (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)carbonyl]-amino-β-D-glucopyranoside (No. 119)

tert-Butyldimethylsilyl triflate (1.13 mL, 0.2 mol per mole of imidate) in dichloromethane is added, under argon and at −20° C., to a solution of the imidate 24 (24.9 g, 24.6 mmol) and 5-phenylpentanol (8.3 mL, 2 molar equivalents) in dichloromethane (1.1 L) in the presence of 4 Å molecular sieves (31 g). After 10 minutes (TLC), saturated aqueous sodium hydrogen carbonate solution at 0° C. is added, and stirring is continued for 1 hour. The solution is filtered, washed with aqueous 2% sodium hydrogen carbonate solution, with saturated aqueous sodium chloride solution, dried (Na$_2$SO$_4$) and evaporated to dryness. Purification on silica gel gives 119 (21.9 g, 88%).
LC-MS m/z 1034.3 [(M+Na)$^+$]. T$_R$=1.80 min Preparation of 2-propylpentyl (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)carbonyl]-amino-3-D-glucopyranoside (No. 120)

A 0.1 M solution of tert-butyldimethylsilyl triflate (2.78 mL, 0.2 mol per mole of imidate) in dichloromethane is added, under argon, at −20° C., to a solution of the imidate 24 (1.2 g, 1.19 mmol) and 2-propylpentanol (1 mL, 5 molar equivalents) in dichloromethane (63 mL) in the presence of 4 Å molecular sieves (1.8 g). After 10 minutes (TLC), saturated aqueous sodium hydrogen carbonate solution is added at 0° C. The solution is filtered, washed with water, dried (Na$_2$SO$_4$) and evaporated to dryness. Purification on silica gel gives 120 (0.91 g, 76%).
LC-MS m/z 1000.3 [(M+Na)$^+$]. T$_R$=1.86 min Preparation of 3-cyclohexylpropyl (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)-carbonyl]amino-3-D-glucopyranoside (No. 121)

Compound 24 (1.2 g, 1.19 mmol) is treated according to a protocol similar to that described for the synthesis of 120 to give compound 121 (1.09 g, 91%).
LC-MS m/z 1012.3 [(M+Na)$^+$]. T$_R$=1.88 min Preparation of 3,3-diphenylpropyl (methyl 2-O-acetyl-3-O-benzyl-4-O-levulinoyl-α-L-idopyranosyluronate)-(1→4)-6-O-acetyl-3-O-benzyl-2-deoxy-2-[(benzyloxy)-carbonyl]amino-β-D-glucopyranoside (No. 122)

Compound 24 (1.2 g, 1.19 mmol) is treated according to a protocol similar to that described for the synthesis of 120 to give compound 122 (1.02 g, 82%).
Rf=0.34 (7/3 cyclohexane/acetone).

Preparation of 5-phenylpentyl (methyl 2-O-acetyl-3-O-benzyl-4-O-levulinoyl-α-L-idopyranosyluronate)-(1→4)-3-O-benzyl-2-deoxy-2-[(benzyloxy)carbonyl]amino-3-D-glucopyranoside (No. 123)

To a solution of 119 (21.9 g, 21.6 mmol) in a 1/1 mixture of methanol/tetrahydrofuran (260 mL) is added [tBu$_2$SnCl(OH)]$_2$ (0.926 g, 0.15 molar equivalent) prepared according to A. Orita et al., Chem. Eur. J. (2001) 7, 3321. After stirring at 35° C. for 7.5 hours and then at room temperature for 17 hours, the reaction mixture is concentrated under vacuum and then used directly in the following step.
LC-MS m/z 992.3 [(M+Na)$^+$]. T$_R$=1.74 min Preparation of 2-propylpentyl (methyl 2-O-acetyl-3-O-benzyl-4-O-levulinoyl-α-L-idopyranosyluronate)-(1→4)-3-O-benzyl-2-deoxy-2-[(benzyloxy)carbonyl]amino-3-D-glucopyranoside (No. 124)

To a solution of 120 (0.9 g, 0.93 mmol) in a 1/1 mixture of methanol/tetrahydrofuran (12 mL) is added [tBu$_2$SnCl(OH)]$_2$ (0.037 g, 0.14 molar equivalent) prepared according to A. Orita et al., Chem. Eur. J. (2001) 7, 3321. After stirring at room temperature for 16 hours and then at 35° C. for 4 hours, the reaction mixture is concentrated under vacuum and then used directly in the following step.
LC-MS m/z 959.2 [(M+Na)$^+$]. T$_R$=1.79 min Preparation of 3-cyclohexylpropyl (methyl 2-O-acetyl-3-O-benzyl-4-O-levulinoyl-α-L-idopyranosyluronate)-(1→4)-3-O-benzyl-2-deoxy-2-[(benzyloxy)carbonyl]amino-3-D-glucopyranoside (No. 125)

Compound 121 (1.09 g, 1.10 mmol) is treated according to a protocol similar to that described for the synthesis of 124 to give compound 125, which is used directly in the following step.
LC-MS m/z 970.3 [(M+Na)$^+$]. T$_R$=10.75 min Preparation of 3,3-diphenylpropyl (methyl 2-O-acetyl-3-O-benzyl-4-O-levulinoyl-α-L-idopyranosyluronate)-(1→4)-3-O-benzyl-2-deoxy-2-[(benzyloxy)carbonyl]amino-3-D-glucopyranoside (No. 126)

Compound 122 (0.844 g, 0.80 mmol) is treated according to a protocol similar to that described for the synthesis of 124. In the event of the reaction being incomplete, the same amount of reagent may optionally be added again. After workup, compound 126 is used directly in the following step.

Rf=0.41 (3/2 cyclohexane/acetone).

Preparation of 5-phenylpentyl (methyl 2-O-acetyl-3-O-benzyl-4-O-levulinoyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 127)

Compound 123 obtained previously is dissolved in dichloromethane (173 mL). Triethylamine (7.6 mL, 2.5 molar equivalents), 4-dimethylaminopyridine (1.3 g, 0.5 molar equivalent), and tert-butyldiphenylsilyl chloride (11.2 mL, 2 molar equivalents) are successively added at 0° C. under argon. After 5.5 hours of magnetic stirring, the reaction medium is diluted with dichloromethane, washed with aqueous 10% potassium hydrogen sulfate solution, with saturated aqueous sodium chloride solution, dried ($Na_2SO_4$), filtered and concentrated. The residue obtained is partially purified on silica (acetone-toluene) which is used in the following step.

LC-MS m/z 1231.2 [(M+Na)$^+$]. $T_R$=2.13 min

Preparation of 2-propylpentyl (methyl 2-O-acetyl-3-O-benzyl-4-O-levulinoyl-α-L-idopyranosyluronate)-(1→4)-3-O-benzyl-6-O-tert-butyldiphenylsilyl-2-deoxy-2-[(benzyl-oxy)carbonyl]amino-β-D-glucopyranoside (No. 128)

Compound 124 obtained previously is dissolved in dichloromethane (7.4 mL). 4-Dimethylaminopyridine (57 mg, 0.5 molar equivalent), triethylamine (0.32 mL, 2.5 molar equivalents), and tert-butyldiphenylsilyl chloride (0.48 mL, 2.0 molar equivalents) are successively added at 0° C. under argon. After 18 hours of magnetic stirring, the reaction medium is diluted with dichloromethane, washed with aqueous 10% potassium hydrogen sulfate solution, with aqueous 2% sodium hydrogen carbonate solution and then with saturated aqueous sodium chloride solution, dried ($Na_2SO_4$), filtered and concentrated. The residue obtained is purified on silica (acetone-cyclohexane) to give 128 (962 mg, 88% (2 steps)).

Rf=0.46 (3/2 cyclohexane/acetone).

Preparation of 3-cyclohexylpropyl (methyl 2-O-acetyl-3-O-benzyl-4-O-levulinoyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 129)

Compound 125 obtained previously is treated according to a protocol similar to that described for the synthesis of 128, to give compound 129 (1.12 g, 86% (2 steps)).

LC-MS m/z 1208.4 [(M+Na)$^+$]. $T_R$=13.01 min

Preparation of 3,3-diphenylpropyl (methyl 2-O-acetyl-3-O-benzyl-4-O-levulinoyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 130)

Compound 126 obtained previously is treated according to a protocol similar to that described for the synthesis of 128, to give compound 130 (0.97 g, 81% (2 steps)).

LC-MS m/z 1278.3 [(M+Na)$^+$]. $T_R$=12.72 min

Preparation of 5-phenylpentyl (methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 131)

To a solution of compound 127 obtained previously in a 1/2 mixture of toluene/ethanol (1.01 L) is added hydrazine acetate (9.3 g, 5 molar equivalents). After 1 hour 10 minutes of magnetic stirring, the mixture is concentrated under vacuum and then purified on silica gel to give compound 131 (16.7 g, 70% (3 steps)).

LC-MS m/z 1133.3 [(M+Na)$^+$]. $T_R$=2.12 min Chemical shifts of the anomeric protons (500 MHz, $CDCl_3$) δ 5.19 IdoUA$^{II}$, 4.63 Glc$^I$ Preparation of 2-propylpentyl (methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 132)

To a solution of compound 128 (0.96 g, 0.82 mmol) in a 1/2 mixture of toluene/ethanol (164 mL) is added hydrazine acetate (0.38 g, 5 molar equivalents). After 1 hour of magnetic stirring, the mixture is concentrated under vacuum and then purified on silica gel to give compound 132 (0.84 g, 96%).

Rf=0.42 (7/3 cyclohexane/acetone).

Mass: "ESI" method, positive mode: theoretical mass=1076.3326; experimental mass: 1098.5109 [M+Na]+.

Chemical shifts of the anomeric protons (500 MHz, $CDCl_3$) δ 5.15 IdoUA$^{II}$, 4.61 Glc$^I$ Preparation of 3-cyclohexylpropyl (methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 133)

Compound 129 (1.12 g, 0.94 mmol) is treated according to a protocol similar to that described for the synthesis of 132, to give compound 133 (1.03 g, 98%).

LC-MS m/z 1110.4 [(M+Na)$^+$]. $T_R$=13.05 min

Chemical shifts of the anomeric protons (500 MHz, $CDCl_3$) δ 5.22 IdoUA$^{II}$, 4.64 Glc$^I$ Preparation of 3,3-diphenylpropyl (methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 134)

Compound 130 (0.96 g, 0.77 mmol) is treated according to a protocol similar to that described for the synthesis of 132, to give compound 134 (833 mg, 94%).

LC-MS m/z 1180.5 [(M+Na)+]. $T_R$=12.22 min
Chemical shifts of the anomeric protons (500 MHz, CDCl$_3$) δ 5.21 IdoUA$^{II}$, 4.54 Glc$^I$

Preparation of 5-phenylpentyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 135)

tert-Butyldimethylsilyl triflate (0.51 mL, 0.15 mol per mole of imidate) in dichloromethane is added, under argon and at −20° C., to a solution of the imidate 63 (24.7 g, 22.5 mmol) and of the glycosyl acceptor 131 (16.7 g, 15 mmol) in dichloromethane (788 mL) in the presence of 4 Å molecular sieves (16.9 g). After 2 hours 45 minutes at −20° C. (TLC), solid sodium hydrogen carbonate is added. After filtering, washing with aqueous 2% sodium hydrogen carbonate solution and with saturated aqueous sodium chloride solution, followed by drying (Na$_2$SO$_4$) and evaporating to dryness, the residue is purified on silica gel to give 135 (20.6 g, 67%).
Chemical shifts of the anomeric protons (500 MHz, CDCl$_3$) δ 5.35 IdoUA$^{IV}$, 4.77 Glc$^{III}$, 5.30 IdoUA$^{II}$, 4.61 Glc$^I$
Rf=0.41 (9/1 toluene/acetone).

Preparation of 2-propylpentyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 136)

A 0.1 M solution of tert-butyldimethylsilyl triflate in dichloromethane (1.1 mL, 0.15 mol per mole of imidate) is added, under argon and at −20° C., to a solution of the imidate 63 (0.81 g, 0.73 mmol) and of the glycosyl acceptor 132 (0.84 g, 0.78 mmol) in dichloromethane (26 mL) in the presence of 4 Å molecular sieves (0.55 g). After 2 hours 30 minutes at −20° C. (TLC), solid sodium hydrogen carbonate is added. After filtering, washing with aqueous 2% sodium hydrogen carbonate solution and with saturated aqueous sodium chloride solution, followed by drying (Na$_2$SO$_4$) and evaporating to dryness, the residue is purified on silica gel to give 136 (0.66 g, 47%).
Rf=0.23 (4/1 cyclohexane/acetone).

Preparation of 3-cyclohexylpropyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 137)

The glycosyl donor 63 (0.63 g, 0.57 mmol) and the glycosyl acceptor 133 (1.03 g, 0.95 mmol) are treated according to a protocol similar to that described for the synthesis of 136 to give compound 137 (716 mg, 62%).
Rf=0.20 (3/1 cyclohexane/acetone).

Preparation of 3,3-diphenylpropyl (methyl 2-O-acetyl-3-O-benzyl-4-O-levulinoyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 138)

The glycosyl donor 63 (0.63 g, 0.57 mmol) and the glycosyl acceptor 134 (0.83 g, 0.72 mmol) are treated according to a protocol similar to that described for the synthesis of 136, to give compound 138.
Rf=0.34 (7/3 cyclohexane/acetone).

Preparation of 5-phenylpentyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 139)

To a solution of compound 135 (20.6 g, 10.0 mmol) in a 1/2 mixture of toluene/ethanol (500 mL) is added hydrazine acetate (4.6 g, 5 molar equivalents). After 1 hour 20 minutes of magnetic stirring, the mixture is concentrated under vacuum and then purified on silica gel to give compound 139 (16.8 g, 86%).
Rf=0.37 (9/1 toluene/acetone).

Preparation of 2-propylpentyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 140)

To a solution of compound 136 (20.6 g, 10.0 mmol) in a 1/2 mixture of toluene/ethanol (500 mL) is added hydrazine acetate (4.6 g, 5 molar equivalents). After 1 hour 20 minutes of magnetic stirring, the mixture is concentrated under vacuum and then purified on silica gel to give compound 140 (16.8 g, 86%).
Rf=0.36 (95/5 toluene/methanol).

Preparation of 3-cyclohexylpropyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 141)

Compound 137 (0.71 g, 0.35 mmol) is treated according to a protocol similar to that described for the synthesis of 140, to give compound 141 (0.65 g, 96%).
Rf=0.37 (7/3 cyclohexane/acetone).

Preparation of 3,3-diphenylpropyl (methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 142)

Compound 138 obtained in the preceding step is treated according to a protocol similar to that described for the synthesis of 140, to give compound 142 (0.518 g, 45% (2 steps)).
Rf=0.37 (9/1 toluene/acetone).

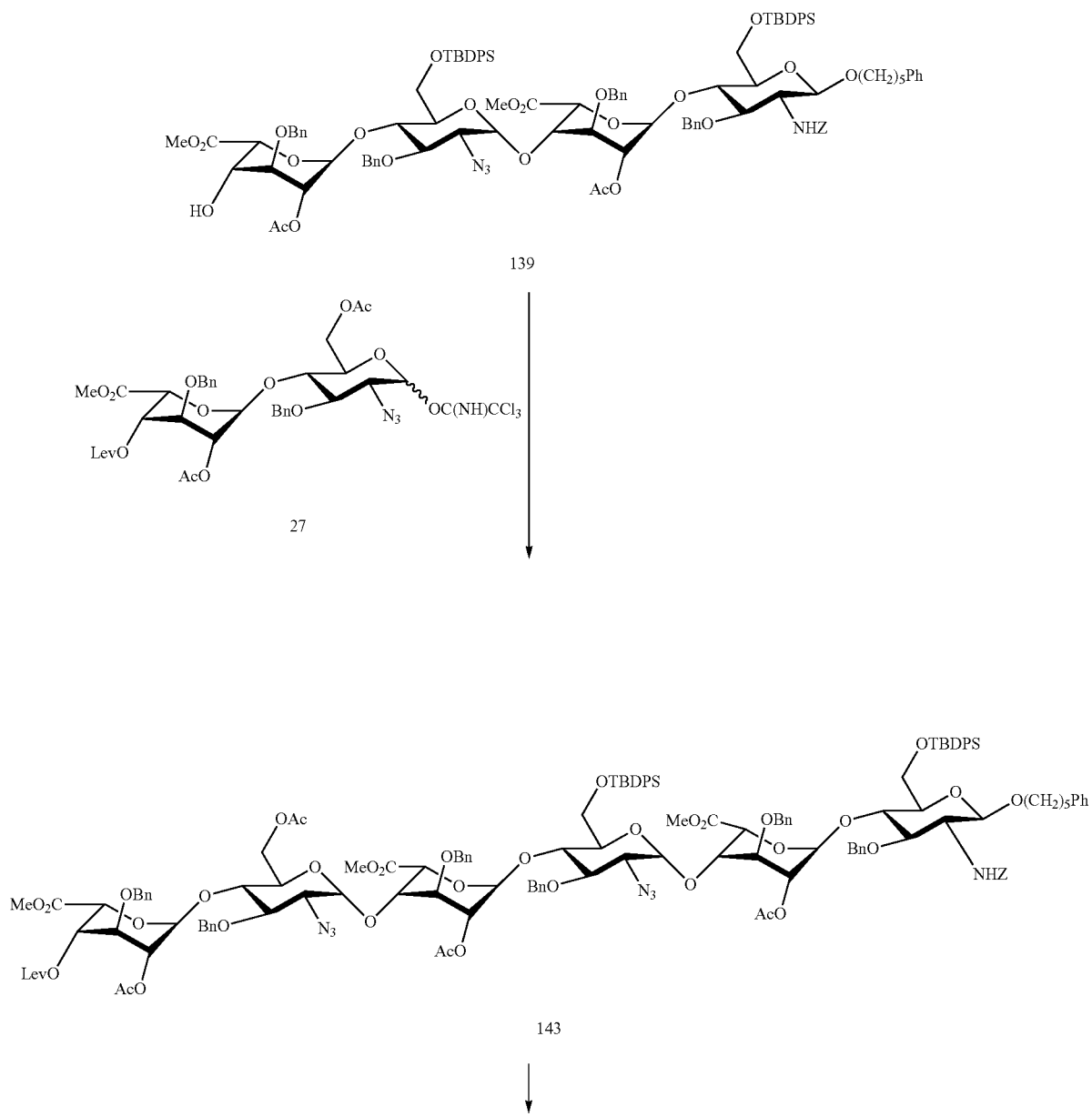

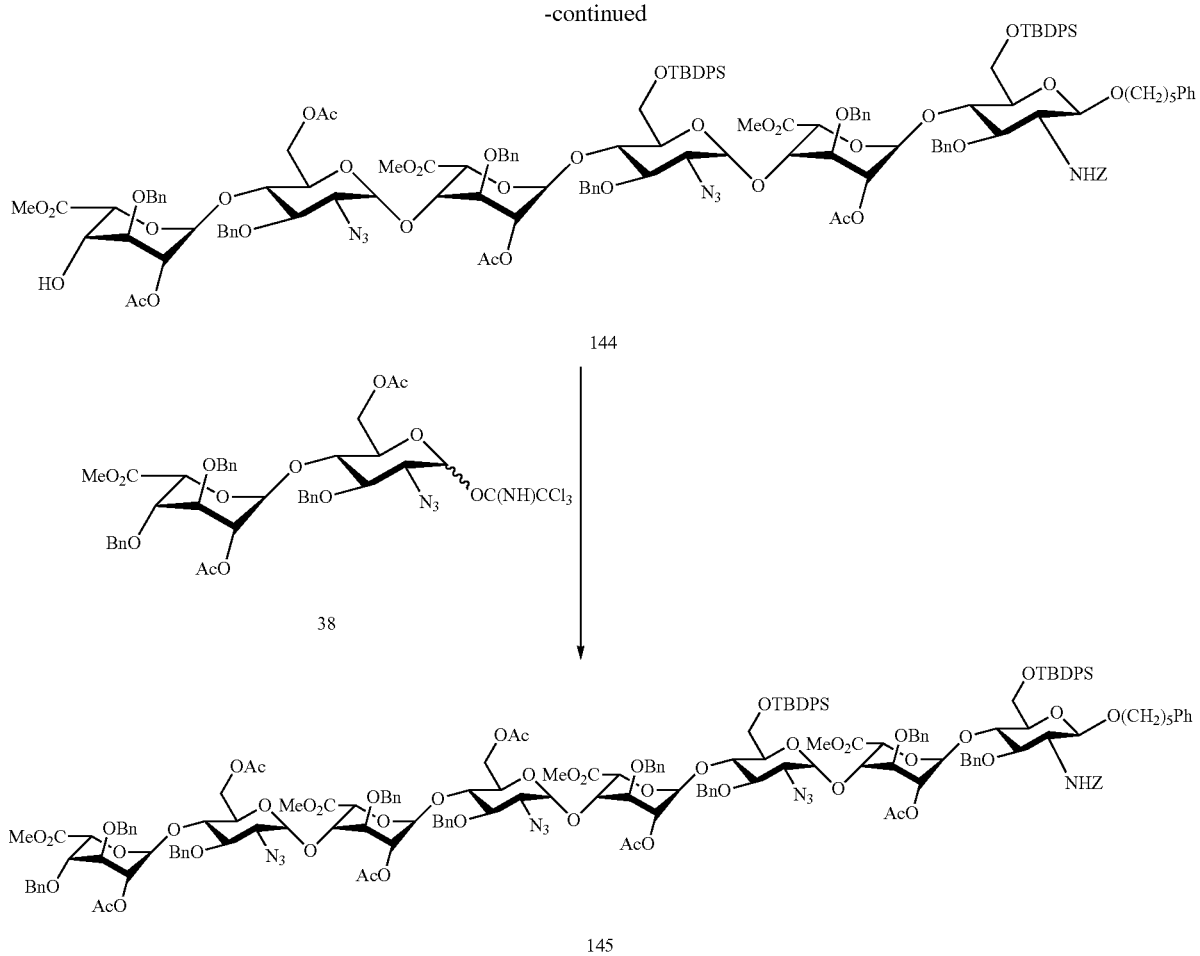

Preparation of 5-phenylpentyl (methyl 2-O-acetyl-3-O-benzyl-4-O-levulinoyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyl uronate)-(1→4)-3-O-benzyl-6-O-tert-butyldiphenylsilyl-2-deoxy-2-[(benzyloxy)carbonyl]amino-δ-D-glucopyranoside (No. 143)

tert-Butyldimethylsilyl triflate (0.42 mL, 0.15 mol per mole of imidate) in dichloromethane is added, under argon and at −20° C., to a solution of the imidate 27 (11.1 g, 12.3 mmol) and of the glycosyl acceptor 139 (16.8 g, 8.6 mmol) in dichloromethane (430 mL) in the presence of 4 Å molecular sieves (10.4 g). After 3 hours of magnetic stirring at −20° C. (TLC), solid sodium hydrogen carbonate is added. After filtering, washing with aqueous 2% sodium hydrogen carbonate solution and with saturated aqueous sodium chloride solution, followed by drying (Na₂SO₄) and evaporating to dryness, the residue is purified on silica gel to give 143 (14.71 g, 64%).

Rf=0.31 (85/15 toluene/acetone).

Preparation of 5-phenylpentyl (methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]amino-δ-D-glucopyranoside (No. 144)

To a solution of compound 143 (13.51 g, 5.0 mmol) in a 1/2 mixture of toluene/ethanol (252 mL) is added hydrazine hydrate (2.31 g, 5 molar equivalents). After 30 minutes of magnetic stirring, the mixture is concentrated under vacuum and then purified on silica gel to give compound 144 (9.41 g, 72%).

Rf=0.18 (85/15 toluene/acetone).

Preparation of 5-phenylpentyl (methyl 2-O-acetyl-3, 4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 145)

A 0.1 M solution of tert-butyldimethylsilyl triflate (7.2 mL, 0.15 mol per mole of imidate) in dichloromethane is added, under argon, at −20° C., to a solution of the imidate 38 (4.29 g, 4.8 mmol) and of the glycosyl acceptor 144 (10.33 g, 4.0 mmol) in dichloromethane (170 mL) in the presence of 4 Å molecular sieves (3.7 g). After 19 hours 45 minutes at −20° C. (TLC), solid sodium hydrogen carbonate is added. After filtering, washing with aqueous 2% sodium hydrogen carbonate solution, with saturated aqueous sodium chloride solution, followed by drying (Na$_2$SO$_4$) and evaporating to dryness, the residue is purified on silica gel to give 145 (7.74 g, 58%).

Rf=0.4 (85/15 toluene/acetone).

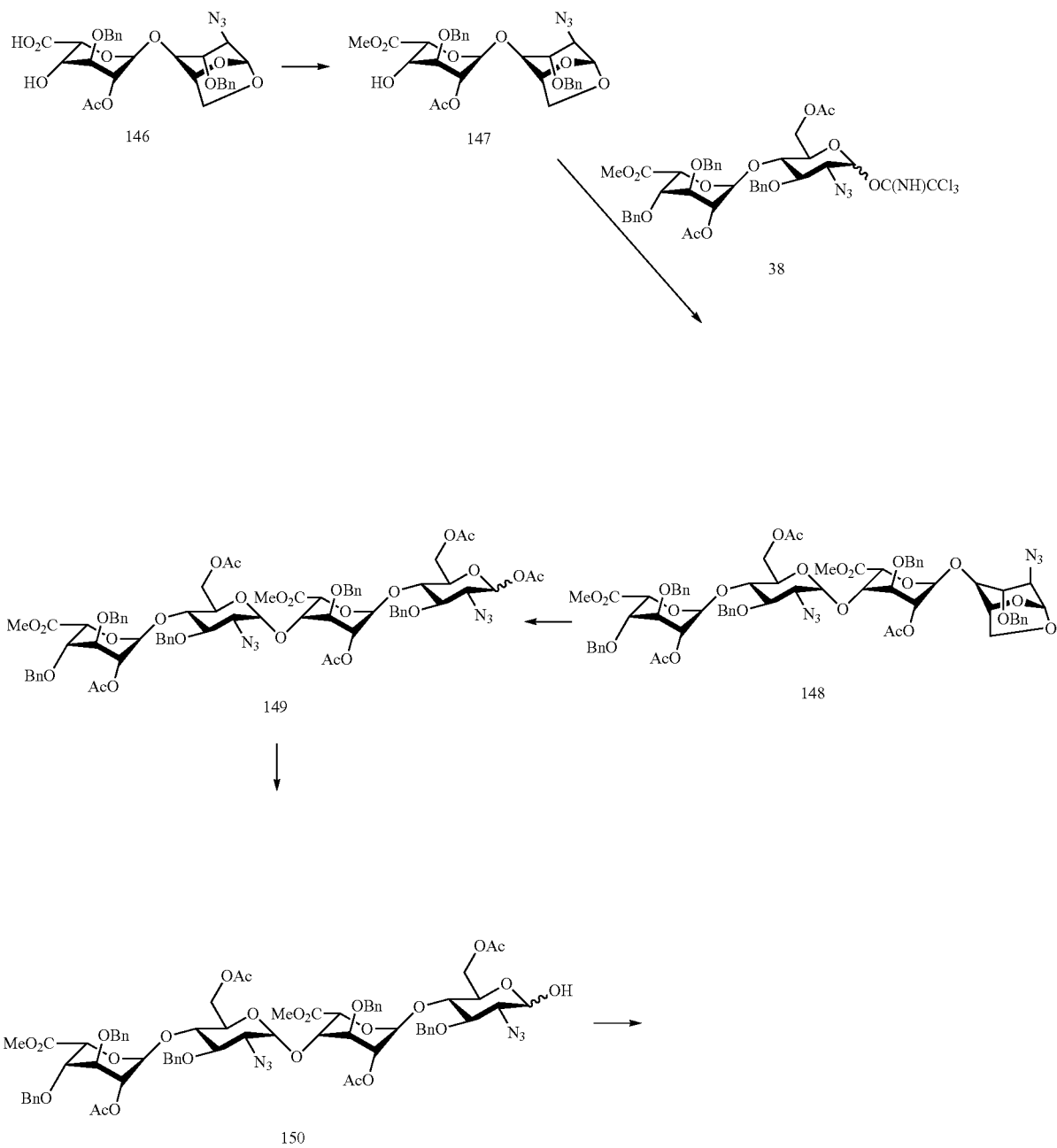

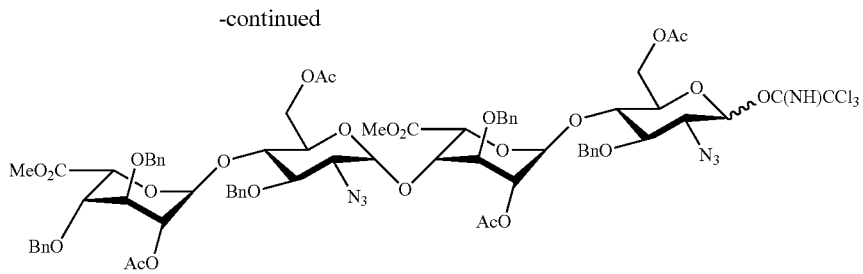

151

Preparation of (methyl 2-O-acetyl-3-O-benzyl-α-L-idopyranosyluronate)-(1→4)-1,6-anhydro-2-azido-3-O-benzyl-2-deoxy-β-D-glucopyranose (No. 147)

To a solution of compound 146 (11.1 mmol) (WO 2006/021 653) in N,N-dimethylformamide (78 mL) is added, at 0° C. and under argon, potassium hydrogen carbonate (5.56 g, 5 molar equivalents), followed by addition of methyl iodide (6.9 mL, 10 molar equivalents). After 17 hours of magnetic stirring, the reagents may be added once again, if necessary. Once the reaction is complete (TLC), the reaction medium is concentrated under vacuum, the crude reaction product is diluted with ethyl acetate, washed with water and then with saturated aqueous sodium thiosulfate solution, dried (Na$_2$SO$_4$), filtered and concentrated. The residue obtained is used in the following step without purification.

LC-MS m/z 465.3 [(M+NH$_4$)$^+$]. T$_R$=0.8 min

Preparation of (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-1,6-anhydro-2-azido-3-O-benzyl-2-deoxy-β-D-glucopyranose (No. 148)

A 1 M solution of tert-butyldimethylsilyl triflate (0.95 mL, 0.15 mol per mole of imidate) in dichloromethane is added, under argon and at −20° C., to a solution of the imidate 38 (5.68 g, 6.35 mmol) and of the glycosyl acceptor 147 (4.2 g, 7 mmol) in dichloromethane (222 mL) in the presence of 4 Å molecular sieves (4.8 g). After 1.5 hours at −20° C. (TLC), catalyst is optionally added until the reaction is complete (TLC), and then solid sodium hydrogen carbonate is added. After filtering, washing with aqueous 2% sodium hydrogen carbonate solution and with saturated sodium chloride solution, drying (Na$_2$SO$_4$), filtering and evaporating to dryness, the residue is purified on silica gel to give 148 (3.15 g, 38%).

Rf=0.41 (3/2 cyclohexane/ethyl acetate).

Preparation of (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-1,6-di-O-acetyl-2-azido-3-O-benzyl-2-deoxy-α,β-D-glucopyranose (No. 149)

The residue obtained in the preceding step is dissolved in acetic anhydride (13 mL), followed by addition, at 0° C. over 15 minutes, of trifluoroacetic acid (TFA) (1.3 mL). The reaction mixture is stirred for 10 minutes at 0° C. and for 18 hours at room temperature, and is then concentrated, co-evaporated with toluene, and purified on silica gel (heptane/ethyl acetate), to give compound 149 (2.99 g, 88%).

LC-MS m/z 1456.0 [(M+Na)$^+$]. T$_R$=1.96 min

Preparation of (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-2-azido-3-O-benzyl-2-deoxy-α,β-D-glucopyranose (No. 150)

To a solution of compound 149 (2.99 g, 2.09 mmol) in diethyl ether (42 mL) is added, at 0° C., benzylamine (BnNH$_2$) (8.2 mL, 36 molar equivalents). After 1.5 hours of stirring at 0° C., and then 4.5 hours at room temperature, the reaction mixture is neutralized with cold (0-4° C.) 1N HCl, washed with water, dried (Na$_2$SO$_4$), filtered and concentrated, and purified on silica gel (heptane/ethyl acetate) to give 150 (2.6 g, 90%).

Rf=0.21 (3/2 cyclohexane/ethyl acetate).

Preparation of (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-6-O-acetyl-2-azido-3-O-benzyl-2-deoxy-α,β-D-glucopyranose trichloroacetimidate (No. 151)

To a solution of compound 150 (2.6 g, 1.9 mmol) in dichloromethane (36 mL) is added, under argon and at 0° C., cesium carbonate (Cs$_2$CO$_3$) (0.97 g, 1.6 molar equivalents), followed by addition of trichloroacetonitrile (CCl$_3$CN) (0.94 mL, 5.0 molar equivalents). After stirring for 1 hour at room temperature, the reaction mixture is filtered and then concentrated. The residue is purified on silica gel (ethyl acetate/cyclohexane+0.1% triethylamine) to give 151 (2.25 g, 80%).

Rf=0.38 (3/2 cyclohexane/ethyl acetate).

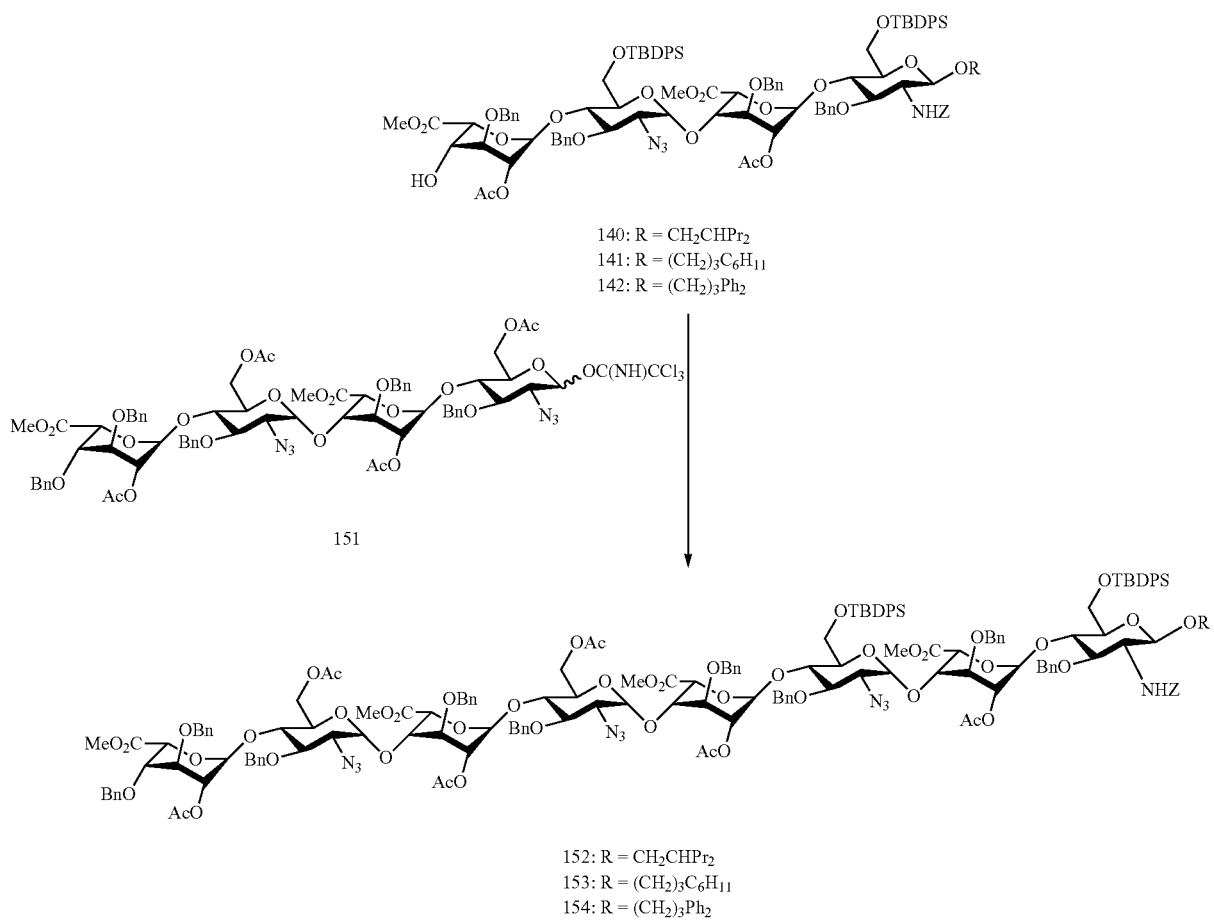

140: R = CH₂CHPr₂
141: R = (CH₂)₃C₆H₁₁
142: R = (CH₂)₃Ph₂

151

152: R = CH₂CHPr₂
153: R = (CH₂)₃C₆H₁₁
154: R = (CH₂)₃Ph₂

Preparation of 2-propylpentyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 152)

A 0.1 M solution of tert-butyldimethylsilyl triflate (0.46 mL, 0.15 mol per mole of imidate) in dichloromethane is added, under argon and at −20° C., to a solution of the imidate 151 (0.56 g, 0.36 mmol) and of the glycosyl acceptor 140 (0.59 g, 0.31 mmol) in dichloromethane (11 mL) in the presence of 4 Å molecular sieves (0.27 g). After 5 hours at −20° C. (TLC), solid sodium hydrogen carbonate is added. After filtering, washing with aqueous 2% sodium hydrogen carbonate solution and with saturated aqueous sodium chloride solution, followed by drying (Na₂SO₄) and evaporating to dryness, the residue is purified on silica gel to give 152 (0.82 g, 82%).

Rf=0.32 (7/3 cyclohexane/acetone).

Preparation of 3-cyclohexylpropyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 153)

The glycosyl donor 151 (0.56 g, 0.36 mmol) and the glycosyl acceptor 141 (0.65 g, 0.34 mmol) are treated according to a protocol similar to that described for the synthesis of 152, to give compound 153 (808 mg, 73%).

Rf=0.36 (3/2 cyclohexane/acetone).

119

Preparation of 3,3-diphenylpropyl (methyl 2-O-acetyl-3,4-di-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 2-O-acetyl-3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 154)

The glycosyl donor 151 (0.51 g, 0.33 mmol) and the glycosyl acceptor 142 (0.52 g, 0.26 mmol) are treated according to a protocol similar to that described for the synthesis of 152, to give compound 154 (635 mg, 73%).

Rf=0.25 (7/3 cyclohexane/acetone).

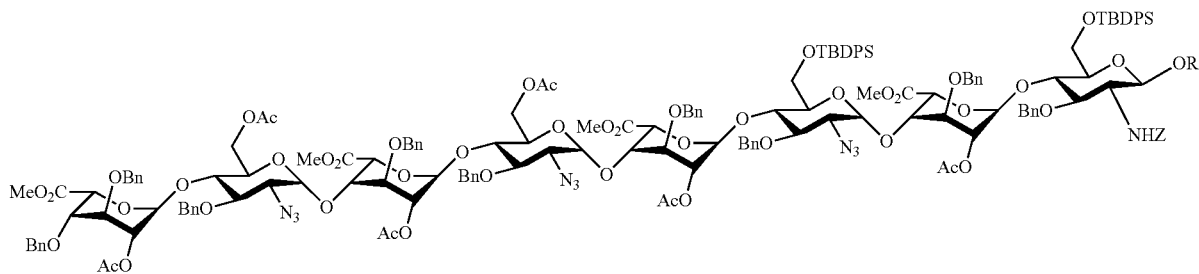

145: R = (CH$_2$)$_5$Ph
152: R = CH$_2$CHPr$_2$
153: R = (CH$_2$)$_3$C$_6$H$_{11}$
154: R = (CH$_2$)$_3$Ph$_2$

↓

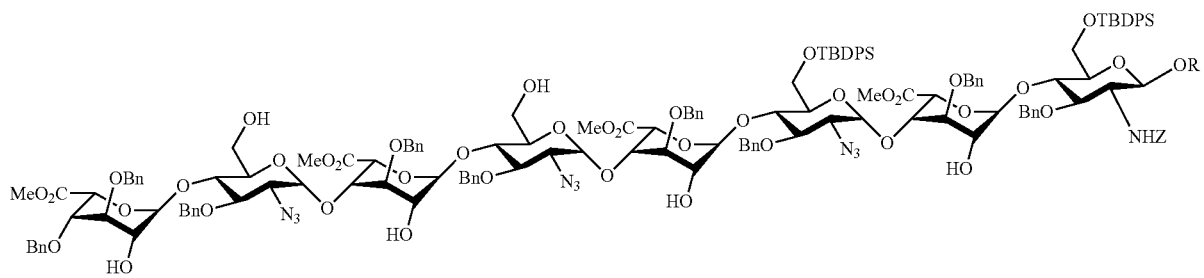

155: R = (CH$_2$)$_5$Ph
156: R = CH$_2$CHPr$_2$
157: R = (CH$_2$)$_3$C$_6$H$_{11}$
158: R = (CH$_2$)$_3$Ph$_2$

↓

-continued
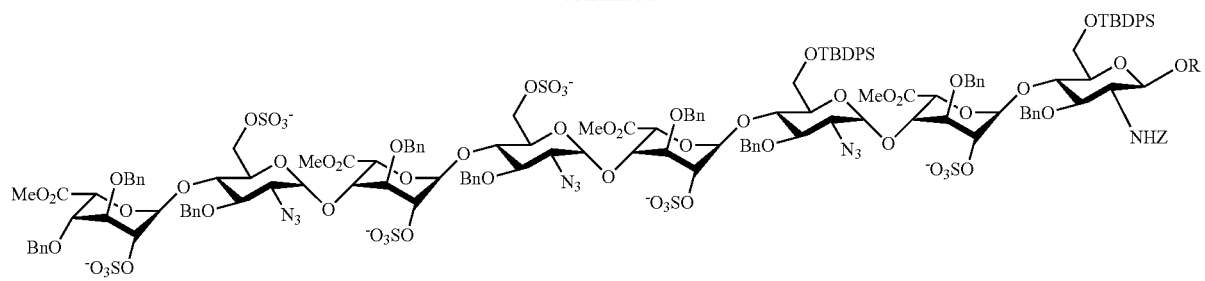
triethylammonium salt
159: R = (CH$_2$)$_5$Ph
160: R = CH$_2$CHPr$_2$
161: R = (CH$_2$)$_3$C$_6$H$_{11}$
162: R = (CH$_2$)$_3$Ph$_2$
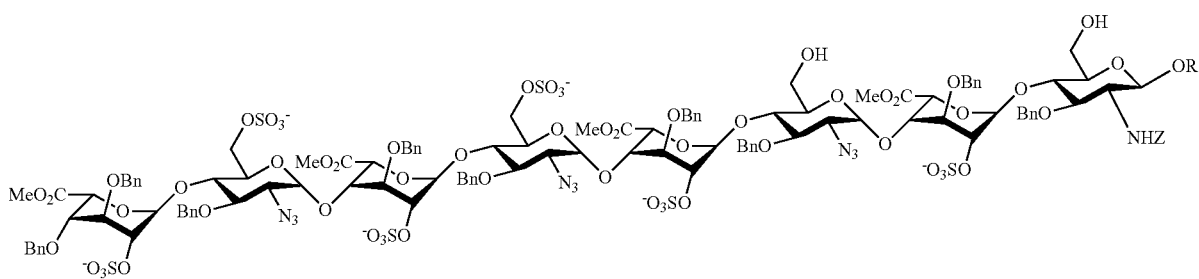
ammonium salt
163: R = (CH$_2$)$_5$Ph
164: R = CH$_2$CHPr$_2$
165: R = (CH$_2$)$_3$C$_6$H$_{11}$
166: R = (CH$_2$)$_3$Ph$_2$
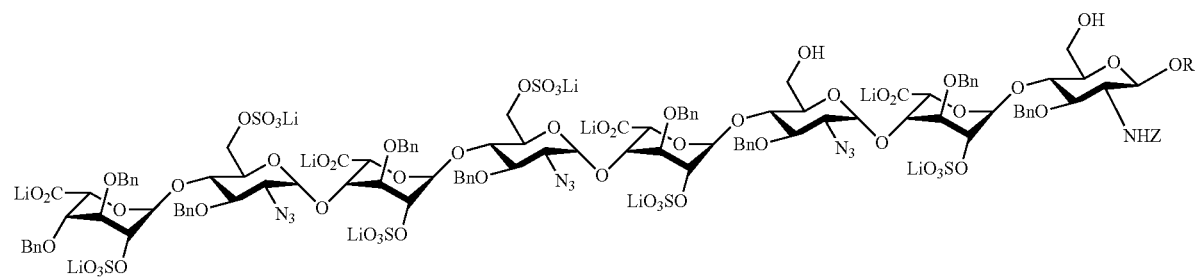
167: R = (CH$_2$)$_5$Ph
168: R = CH$_2$CHPr$_2$
169: R = (CH$_2$)$_3$C$_6$H$_{11}$
170: R = (CH$_2$)$_3$Ph$_2$

-continued

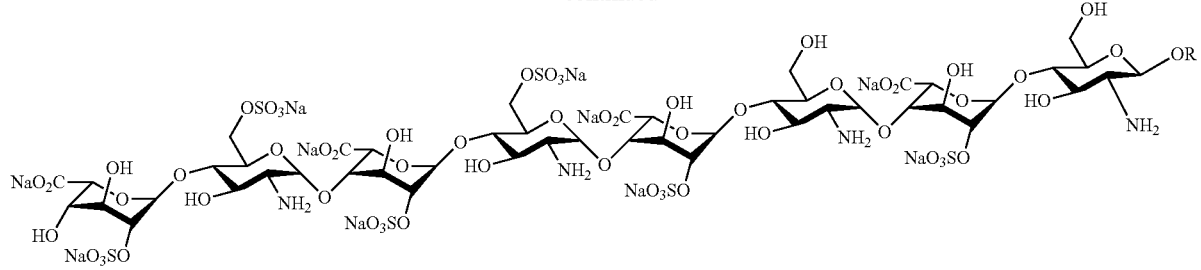

171: R = (CH$_2$)$_5$Ph
172: R = CH$_2$CHPr$_2$
173: R = (CH$_2$)$_3$C$_6$H$_{11}$
174: R = (CH$_2$)$_3$Ph$_2$

Preparation of 5-phenylpentyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyl uronate)-(1→4)-(2-azido-3-O-benzyl-6-O-tert-butyl-diphenylsilyl-2-deoxy-α-D-glucopyranosyl)-(1→4)-(methyl 3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 155)

To a solution of 145 (639 mg, 0.192 mmol) in a 3/2 mixture of methanol/dichloromethane (57 mL) in the presence of 3 Å molecular sieves (230 mg) is added, at 0° C., a 1M methanolic solution of sodium methoxide (0.427 mL). After stirring at 0° C. for 3 hours and at room temperature for 15 hours, the mixture is neutralized at 0° C. with H$^+$ Dowex 50WX4 resin. After filtering and concentrating, the residue is purified on silica gel with a toluene/ethyl acetate/ethanol mixture to give compound 155 (444 mg, 80%).

Rf=0.28 (7/3/0.3 toluene/ethyl acetate/ethanol).

Preparation of 2-propylpentyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyl uronate)-(1→4)-(2-azido-3-O-benzyl-6-O-tert-butyl-diphenylsilyl-2-deoxy-α-D-glucopyranosyl)-(1→4)-(methyl 3-O-benzyl-α-L-idopyranosyluronate)-(1→4)-3-O-benzyl-6-O-tert-butyldiphenylsilyl-2-deoxy-2-[(benzyloxy)carbonyl]-amino-β-D-glucopyranoside (No. 156)

Compound 152 (420 mg, 0.128 mmol) is treated according to a protocol similar to that described for the synthesis of 155, to give compound 156 (178 mg, 46%).

Rf=0.20 (7/3 cyclohexane/acetone).

Preparation of 3-cyclohexylpropyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyl uronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyl uronate)-(1→4)-3-O-benzyl-6-O-tert-butyldiphenylsilyl-2-deoxy-2-[(benzyloxy)carbonyl] amino-β-D-glucopyranoside (No. 157)

Compound 153 (402 mg, 0.122 mmol) is treated according to a protocol similar to that described for the synthesis of 155, to give compound 157 (276 mg, 75%).

Rf=0.40 (7/3 cyclohexane/acetone).

Preparation of 3,3-diphenylpropyl (methyl 3,4-di-O-benzyl-α-L-idopyranosyluronate)-(1→4)-(2-azido-3-O-benzyl-2-deoxy-α-D-glucopyranosyl)-(1→4)-(methyl 3-O-benzyl-α-L-idopyranosyl uronate)-(1→4)-(2-azido-3-O-benzyl-2-deoxy-α-D-glucopyranosyl)-(1→4)-(methyl 3-O-benzyl-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-α-L-idopyranosyl uronate)-(1→4)-3-O-benzyl-6-O-tert-butyldiphenylsilyl-2-deoxy-2-[(benzyloxy)carbonyl] amino-β-D-glucopyranoside (No. 158)

Compound 154 (315 mg, 0.093 mmol) is treated according to a protocol similar to that described for the synthesis of 155, to give compound 158 (244 mg, 84%).

Rf=0.13 (7/3 cyclohexane/acetone).

Preparation of 5-phenylpentyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyluronate)-(1→4)-3-O-benzyl-6-O-tert-butyldiphenylsilyl-2-deoxy-2-[(benzyloxy)carbonyl]amino-β-D-glucopyranoside (No. 159)

Triethylamine/sulfur trioxide complex (775 mg, 5 mol per hydroxyl function) is added to a solution in N,N-dimethylformamide (12.8 mL, 90 L/mol) of compound 155 (438 mg, 142 µmol). After 17 hours of magnetic stirring at 50° C. sheltered from light, methanol is added at 0° C. and, after stirring for 30 minutes at 0° C. and then 1 hour at room temperature, the reaction medium is diluted with methanol and then purified by means of an LH-20 column, using a 9/1 mixture of methanol/N,N-dimethylformamide as eluent. The fractions containing the product are then concentrated under high vacuum to give the desired compound 159 (571 mg, 96%).

Rf=0.48 (29/13/3.4/7 EtOAc/pyridine/AcOH/H$_2$O).

Preparation of 2-propylpentyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyl uronate)-(1→4)-3-O-benzyl-6-O-tert-butyldiphenylsilyl-2-deoxy-2-[(benzyloxy)carbonyl]amino-β-D-glucopyranoside (No. 160)

Compound 156 (178 mg, 0.054 mmol) is treated according to a protocol similar to that described for the synthesis of 159, to give compound 160 (196 mg, 75%).

Rf=0.48 (57/29/7.2/16 EtOAc/pyridine/AcOH/H$_2$O).

Preparation of 3-cyclohexylpropyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyl uronate)-(1→4)-3-O-benzyl-6-O-tert-butyldiphenylsilyl-2-deoxy-2-[(benzyloxy)carbonyl]amino-β-D-glucopyranoside (No. 161)

Compound 157 (345 mg, 0.113 mmol) is treated according to a protocol similar to that described for the synthesis of 159, to give compound 161 (332 mg, 70%).

Rf=0.48 (57/29/7.2/16 EtOAc/pyridine/AcOH/H$_2$O).

Preparation of 3,3-diphenylpropyl (methyl 3,4-di-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-2-deoxy-6-O-triethylammonium sulfonato-α-D-glucopyranosyl)-(1→4)-(methyl 3-O-benzyl-2-O-triethylammonium sulfonato-α-L-idopyranosyluronate)-(1→4)-(2-azido-3-O-benzyl-6-O-tert-butyldiphenylsilyl-2-deoxy-α-D-glucopyranosyl)-(1→4)-(methyl 3-O-benzyl-2-O-triethylammonium sulfonato-α-L-idopyranosyl uronate)-(1→4)-3-O-benzyl-6-O-tert-butyldiphenylsilyl-2-deoxy-2-[(benzyloxy)carbonyl]amino-β-D-glucopyranoside (No. 162)

Compound 158 (300 mg, 0.096 mmol) is treated according to a protocol similar to that described for the synthesis of 159. If necessary, the mixture obtained may be purified on an RP-18 reverse-phase column using a methanol/water mixture as eluent, to give compound 162 (211 mg, 52%).

Rf=0.47 (29/13/3.4/7 EtOAc/pyridine/AcOH/H$_2$O).

Preparation of 5-phenylpentyl (methyl 3,4-di-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-3-O-benzyl-2-deoxy-2-[(benzyloxy)carbonyl]amino-β-D-glucopyranoside (No. 163)

To a solution of compound 159 (520 mg, 125 µmol) in methanol (16 mL) is added ammonium fluoride (370 mg, 80 molar equivalents). After magnetic stirring at 55° C. for 24 hours and then at room temperature for 16 hours, the reaction mixture is purified with the aid of an LH-20 column using a 9/1 mixture of methanol/N,N-dimethylformamide as eluent. The fractions containing the product are then concentrated under high vacuum and the residue is purified on silica gel with an ethyl acetate/pyridine/acetic acid/water mixture as eluent. The fractions containing the product are then partially concentrated and the residue is purified by means of an LH-20 column, using a 9/1 mixture of methanol/N,N-dimethylformamide as eluent. The fractions containing the product are then concentrated under high vacuum to give compound 163 (295 mg, 74%).

Rf=0.45 (29/13/3.4/7 EtOAc/pyridine/AcOH/H$_2$O).

Preparation of 2-propylpentyl (methyl 3,4-di-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-3-O-benzyl-2-deoxy-2-[(benzyloxy)carbonyl]amino-β-D-glucopyranoside (No. 164)

Compound 160 (196 mg, 0.048 mmol) is treated according to a protocol similar to that described for the synthesis of 163. The reaction time may optionally be shortened according to the TLC monitoring. Moreover, reverse-phase purification may prove to be necessary in order to obtain compound 164 (104 mg, 59%).

Rf=0.32 (57/29/7.2/16 EtOAc/pyridine/AcOH/H$_2$O).

Preparation of 3-cyclohexylpropyl (methyl 3,4-di-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-3-O-benzyl-2-deoxy-2-[(benzyloxy)carbonyl]amino-β-D-glucopyranoside (No. 165)

Compound 161 (230 mg, 0.055 mmol) is treated according to a protocol similar to that described for the synthesis of 164, to give compound 165 (115 mg, 56%).

Rf=0.57 (57/29/7.2/16 EtOAc/pyridine/AcOH/H$_2$O).

Preparation of 3,3-diphenylpropyl (methyl 3,4-di-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-6-O-ammonium sulfonato-α-D-glucopyranosyl)-(1→4)-(methyl 3-O-benzyl-2-O-ammonium sulfonato-α-L-idopyranosyluronate)-(1→4)-(2-azido-3-O-benzyl-2-deoxy-α-D-glucopyranosyl)-(1→4)-(methyl 3-O-benzyl-2-O-ammonium sulfonato-α-L-idopyranosyluronate)-(1→4)-3-O-benzyl-2-deoxy-2-[(benzyloxy)carbonyl]amino-β-D-glucopyranoside (No. 166)

Compound 162 (43 mg, 10.2 μmol) is treated according to a protocol similar to that described for the synthesis of 163, to give compound 166.

Rf=0.32 (29/13/3.4/7 EtOAc/pyridine/AcOH/H$_2$O).

Preparation of 5-phenylpentyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]-amino-β-D-glucopyranoside (No. 167)

To a solution of compound 163 (289 mg, 91 μmol) in methanol (3.59 mL) are added, at 0° C., aqueous 30% hydrogen peroxide solution (2.23 mL), followed by dropwise addition of aqueous 5N LiOH solution (1.46 mL). After stirring for 3 hours at 0° C., for 16 hours at room temperature and then for 27 hours at 45° C., the reaction medium is neutralized at 0° C. by addition of 3N hydrochloric acid, and then purified by means of an LH-20 column, using a 9/1 mixture of methanol/N,N-dimethylformamide as eluent. The fractions containing the product are then concentrated under high vacuum to give the desired compound 167 (267 mg, 95%).

Rf=0.25 (57/29/7.2/16 EtOAc/pyridine/AcOH/H$_2$O).

Preparation of 2-propylpentyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]-amino-β-D-glucopyranoside (No. 168)

Compound 164 (104 mg, 0.029 mmol) is treated according to a protocol similar to that described for the synthesis of 167, to give compound 168.

Rf=0.28 (57/29/7.2/16 EtOAc/pyridine/AcOH/H$_2$O).

Preparation of 3-cyclohexylpropyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]-amino-β-D-glucopyranoside (No. 169)

Compound 165 (110 mg, 0.030 mmol) is treated according to a protocol similar to that described for the synthesis of 167, to give compound 169 (76 mg, 83%).
Rf=0.20 (57/29/7.2/16 EtOAc/pyridine/AcOH/H$_2$O).

Preparation of 3,3-diphenylpropyl (lithium 3,4-di-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-6-O-lithium sulfonato-α-D-glucopyranosyl)-(1→4)-(lithium 3-O-benzyl-2-O-lithium sulfonato-α-L-idopyranosyluronate)-(1→4)-(2-azido-3-O-benzyl-2-deoxy-α-D-glucopyranosyl)-(1→4)-(lithium 3-O-benzyl-2-O-lithium sulfonato-α-L-idopyranosyluronate)-(1→4)-3-O-benzyl-2-deoxy-2-[(benzyloxy)carbonyl]-amino-β-D-glucopyranoside (No. 170)

Compound 166 is treated according to a protocol similar to that described for the synthesis of 167. If necessary, the residue obtained may be used under the same conditions to give compound 170 (27 mg, 87% (2 steps)).
Rf=0.39 (57/29/7.2/16 EtOAc/pyridine/AcOH/H$_2$O).

Preparation of 5-phenylpentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-β-D-glucopyranoside (No. 171)

To a solution in a 1/1 mixture of tert-butanol/water (16.1 mL) of compound 167 obtained previously are successively added ammonium formate (658 mg, 10.4 mmol) and then 10% Pd/C (1.61 g). After stirring vigorously for 4 hours at room temperature, the reaction medium is filtered and partially concentrated under vacuum, and the solution is then applied to a Sephadex® G-25 column eluted with 0.2 M sodium chloride. The fractions containing the product are concentrated and desalified using the same column eluted with water. The fractions containing the product are then concentrated under high vacuum to give the desired compound 171 (109 mg, 62%).

"ESI" method, negative mode: multicharged ion detected m/z 663.08 [M−3H]$^{3-}$ (acid form).

Preparation of 2-propylpentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-β-D-glucopyranoside (No. 172)

Compound 168 is treated according to a protocol similar to that described for the synthesis of 171, to give compound 172 (47 mg, 74% (2 steps)).
Chemical shifts of the anomeric protons (500 MHz, D$_2$O) δ 5.29* IdoUA$^{VIII}$, 5.50** Glc$^{VII}$, 5.29* IdoUA$^{VI}$, 5.48** Glc$^{V}$, 5.29* IdoUA$^{IV}$, 5.48** Glc$^{III}$, 5.22* IdoUA$^{II}$, 4.78** Glc$^{I}$

* and **: The signals may be interchanged.

Preparation of 3-cyclohexylpentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-β-D-glucopyranoside (No. 173)

Compound 169 (88 mg, 29 μmol) is treated according to a protocol similar to that described for the synthesis of 171, to give compound 173 (63 mg, 99%).
Chemical shifts of the anomeric protons (500 MHz, D$_2$O) δ 5.29* IdoUA$^{VIII}$, 5.50** Glc$^{VII}$, 5.29* IdoUA$^{VI}$, 5.48** Glc$^{V}$, 5.29* IdoUA$^{IV}$, 5.48** Glc$^{III}$, 5.22* IdoUA$^{II}$, 4.78** Glc$^{I}$

* and **: The signals may be interchanged.

Preparation of 3,3-diphenylpentyl (sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-6-O-sodium sulfonato-α-D-glucopyranosyl)-(1→4)-(sodium 2-O-sodium sulfonato-α-L-idopyranosyluronate)-(1→4)-(2-amino-2-deoxy-α-D-glucopyranosyl)-(1→4)-(sodium 2-O-sodium sulfonato-α-L-idopyranosyluronate)-(1→4)-2-amino-2-deoxy-β-D-glucopyranoside (No. 174)

Compound 170 (17.4 mg, 5.6 μmol) is treated according to a protocol similar to that described for the synthesis of 171, to give compound 174 (5.5 mg, 44%).
Chemical shifts of the anomeric protons (600 MHz, D$_2$O) δ 5.15 IdoUA$^{VIII}$, 5.42 Glc$^{VII}$, 5.23 IdoUA$^{VI}$, 5.40 Glc$^{V}$, 5.23 IdoUA$^{IV}$, 5.38 Glc$^{III}$, 5.19 IdoUA$^{II}$, 4.39 Glc$^{I}$

EXAMPLES OF COMPOUNDS ACCORDING TO THE INVENTION

Example 1

Pentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (Compound 1)

Example 2

Pentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)-amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-αβ-glucopyranosyl)-(1→4)-(sodium 2-O-sodium sulfonato-α-L-idopyranosyluronate)-(1→4)-2-deoxy-2-(1-oxobutyl)amino-6-O-sodium sulfonato-β-D-glucopyranoside (Compound 2)

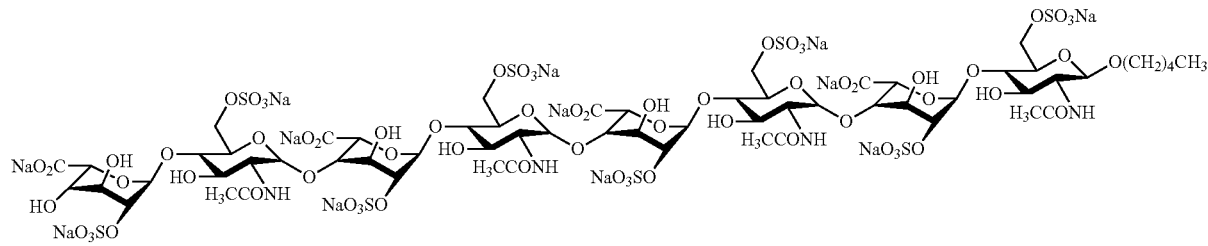

To a saturated aqueous sodium hydrogen carbonate solution (2.1 mL) of compound 43 (39 mg, 16.6 μmol) is added sodium hydrogen carbonate (223 mg, 2.66 mmol), followed

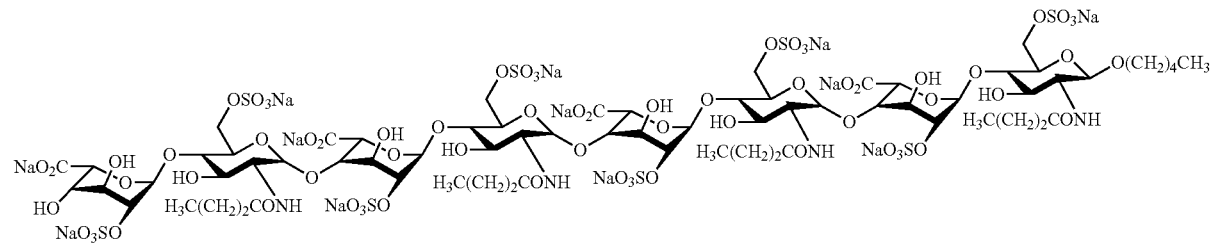

by dropwise addition, at 0° C., of acetic anhydride (126 μL, 1.33 mmol). After stirring vigorously for 3 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 1 (30 mg, 73%).

Chemical shifts of the anomeric protons (500 MHz, D$_2$O) δ 5.14 IdoUA$^{VIII}$, 5.13 Glc$^{VII}$, 5.16 IdoUA$^{VI}$, 5.13 Glc$^{V}$, 5.15 IdoUA$^{IV}$, 5.14 Glc$^{III}$, 5.17 IdoUA$^{II}$, 4.51 Glc$^{I}$ Mass: "ESI" method, negative mode: theoretical mass=2509.72; experimental mass: 2508.82±0.34 a.m.u.

To a solution of compound 43 (26 mg, 11.1 μmol) in a 7/3 mixture of N,N-dimethylformamide/water (2.9 mL) are added dropwise, at 0° C., diisopropylethylamine (33 μL, 17 molar equivalents) dissolved in N,N-dimethylformamide (100 μL) and N-hydroxysuccinimide butyrate (27.4 mg, 13 molar equivalents) dissolved in N,N-dimethylformamide (100 μL). Stirring is continued at room temperature for 4 hours, and the same amount of reagent is then added twice more under the same conditions. After a total of 18 hours of stirring at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 2 (26 mg, 89%).

Chemical shifts of the anomeric protons (600 MHz, D$_2$O) δ 5.14 IdoUA$^{VIII}$, 5.12* Glc$^{VII}$, 5.14 IdoUA$^{VI}$, 5.11* Glc$^{V}$, 5.14 IdoUA$^{IV}$, 5.10* Glc$^{III}$, 5.15 IdoUA$^{II}$, 4.50 Glc$^{I}$

Example 3

Pentyl (sodium 2-O-sodium sulfonato-α-L-idopyra-nosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-2-deoxy-2-(1-oxohexyl)amino-6-O-sodium sulfonato-β-D-glucopyranoside (Compound 3)

Example 4

Pentyl (sodium 2-O-sodium sulfonato-α-L-idopyra-nosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-2-[(cyclopentylcarbonyl)amino]-2-deoxy-6-O-sodium sulfonato-β-D-glucopyranoside (Compound 4)

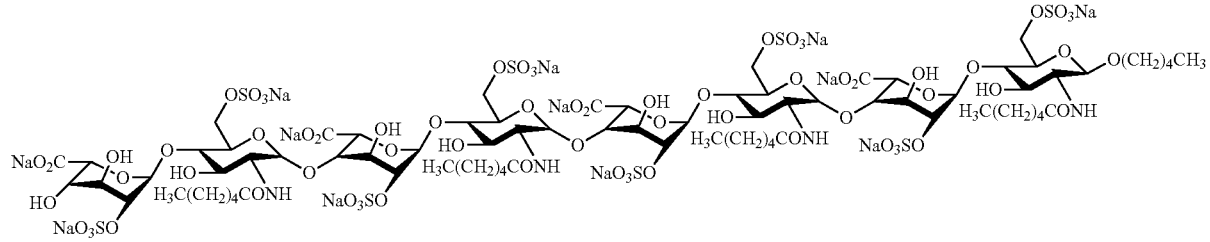

To a solution of compound 43 (10 mg, 4.27 µmol) in water (0.3 mL) are added dropwise, at 0° C., diisopropylethylamine (20 µL, 26.8 molar equivalents) dissolved in N,N-dimethylformamide (200 µL) and N-hydroxysuccinimide hexanoate (18.2 mg, 20 molar equivalents) dissolved in N,N-dimethyl-

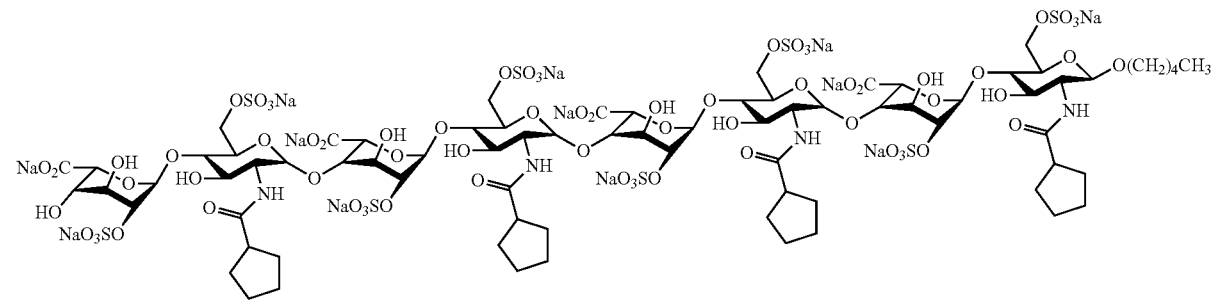

formamide (500 µL). Stirring is continued at 0° C. for 15 minutes and then at room temperature for 16 hours. The reaction medium is then applied to a Sephadex® G-25 column eluted with 0.2 M sodium chloride. The fractions containing the product are concentrated and desalified using the same column eluted with water. The fractions containing the product are then concentrated under high vacuum to give the desired compound 3 (4 mg, 34%).

Chemical shifts of the anomeric protons (600 MHz, $D_2O$) δ 5.11 IdoUA$^{VIII}$, 5.08 Glc$^{VII}$, 5.14 IdoUA$^{VI}$, 5.09 Glc$^{V}$, 5.13 IdoUA$^{IV}$, 5.10 Glc$^{III}$, 5.14 IdoUA$^{II}$, 4.47 Glc$^{I}$ "ESI" method, negative mode: multicharged ion detected m/z 627.6120 [M−4H]$^{4−}$ (acid form).

To a solution of compound 43 (9 mg, 3.84 µmol) in water (0.3 mL) are added dropwise, at 0° C., N,N-dimethylformamide (0.5 mL), diisopropylethylamine (7 µL, 2.6 molar equivalents per free amine) dissolved in N,N-dimethylformamide (50 µL) and N-hydroxysuccinimide cyclopentanecarboxylate (6.6 mg, 2 molar equivalents per free amine) dissolved in N,N-dimethylformamide (50 µL). Stirring is continued at room temperature for 2 hours, and the same amount of reagent is then added four more times under the same conditions. After a total of 18 hours of stirring at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 4 (5.6 mg, 55%). In the event of an incomplete reaction, the product obtained may be reused under the same conditions. If necessary, it may be purified by ion-exchange chromatography using a semi-preparative Dionex CarboPac® PA100 column (9×250 mm) with a gradient starting from an eluent A to an eluent B, eluent A consisting of a water/acetonitrile mixture (4/1)+0.01% of dimethyl sulfoxide, and eluent B consisting of a mixture of a 2N sodium chloride solution and acetonitrile (4/1). The fractions containing the product are then concentrated and desalified using a Sephadex® G-25 column eluted with water. The fractions containing the product are then concentrated under high vacuum to give the desired compound 4.

Chemical shifts of the anomeric protons (600 MHz, D$_2$O) δ 5.06* IdoUA$^{VIII}$, 5.05** Glc$^{VII}$, 5.08* IdoUA$^{VI}$, 5.03** Glc$^{V}$, 5.06* IdoUA$^{IV}$, 5.05** Glc$^{III}$, 5.08* IdoUA$^{II}$, 4.44** Glc$^{I}$

* and **: The signals may be interchanged.

$[\alpha]_D$ 15.4° (c 0.25; H$_2$O).

Example 5

Undecyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside
(Compound 5)

by dropwise addition, at 0° C., of acetic anhydride (100 μL, 1.05 mmol). After stirring vigorously for 2.5 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 5 (31 mg, 91%).

Chemical shifts of the anomeric protons (500 MHz, D$_2$O) δ 5.14 IdoUA$^{VIII}$, 5.13* Glc$^{VII}$, 5.14** IdoUA$^{VI}$, 5.13* Glc$^{V}$, 5.15** IdoUA$^{IV}$, 5.13* Glc$^{III}$, 5.16 IdoUA$^{II}$, 4.50 Glc$^{I}$

* and **: The signals may be interchanged.

$[\alpha]_D$ 18.6° (c 1; H$_2$O).

Example 6

5-phenylpentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside
(Compound 6)

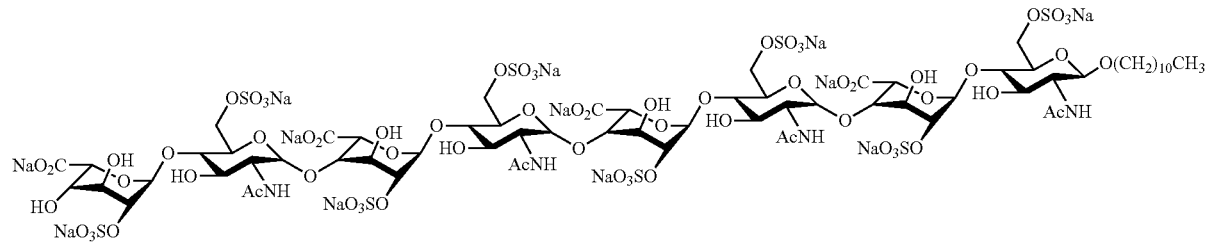

To a saturated aqueous sodium hydrogen carbonate solution (2.3 mL) of compound 52 (32 mg, 13.2 μmol) is added sodium hydrogen carbonate (174 mg, 2.08 mmol), followed

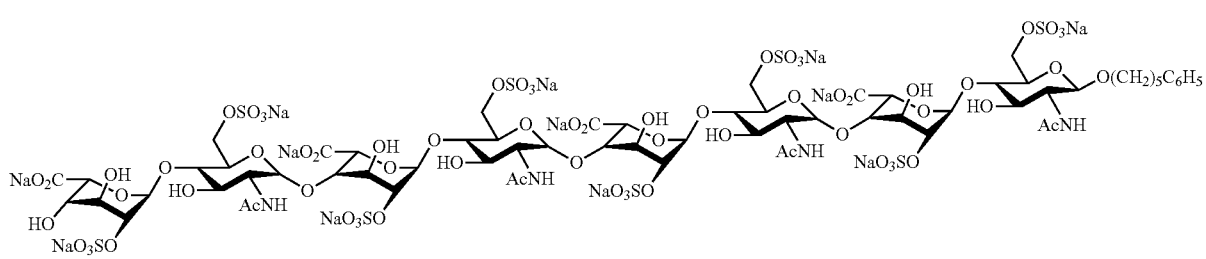

To a saturated aqueous sodium hydrogen carbonate solution (2.7 mL) of compound 53 (36 mg, 14.8 µmol) is added sodium hydrogen carbonate (199 mg, 2.38 mmol), followed by dropwise addition, at 0° C., of acetic anhydride (112 µL, 1.19 mmol). After stirring vigorously for 2.5 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 6 (25.6 mg, 68%). If necessary, it may be purified by ion-exchange chromatography using a semi-preparative Dionex CarboPac® PA100 column (9×250 mm) with a gradient starting from an eluent A to an eluent B, eluent A consisting of a water/acetonitrile mixture (4/1)+0.01% of dimethyl sulfoxide, and eluent B consisting of a mixture of a 2N sodium chloride solution and acetonitrile (4/1). The fractions containing the product are then concentrated and desalified using a Sephadex® G-25 column eluted with water. The fractions containing the product are then concentrated under high vacuum to give the desired compound 6.

Chemical shifts of the anomeric protons (500 MHz, D$_2$O) δ 5.14 IdoUA$^{VIII}$, 5.12 Glc$^{VII}$, 5.16 IdoUA$^{VI}$, 5.12 Glc$^{V}$, 5.16 IdoUA$^{IV}$, 5.12 Glc$^{III}$, 5.17 IdoUA$^{II}$, 4.48 Glc$^{I}$ "ESI" method, negative mode: multicharged ion detected m/z 579.0867 [M−4H]$^{4-}$ (acid form).

Example 7

Methyl (sodium 2-O-sodium sulfonato-α-L-idopyranosyluronate)-(1→4)-(2-acetamido-2-deoxy-6-O-sodium sulfonato-α-D-glucopyranosyl)-[(1→4)-(sodium 2-O-sodium sulfonato-α-L-idopyranosyluronate)-(1→4)-(2-acetamido-2-deoxy-6-O-sodium sulfonato-α-D-glucopyranosyl)]$_2$-(1→4)-(sodium 2-O-sodium sulfonato-α-L-idopyranosyluronate)-(1→4)-2-acetamido-2-deoxy-6-O-sodium sulfonato-α-D-glucopyranoside (Compound 7)

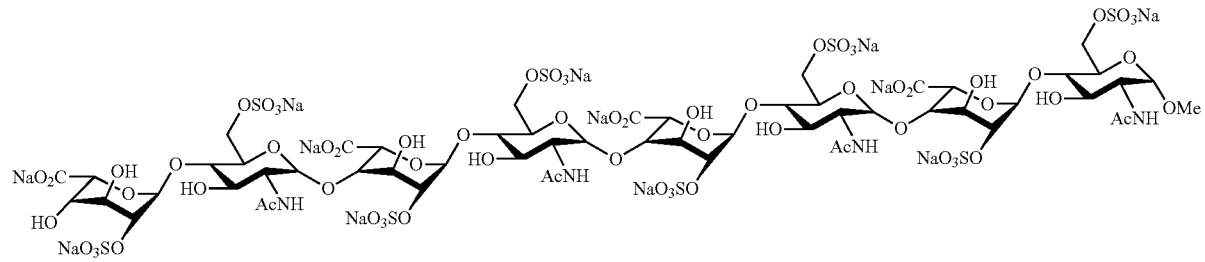

To a solution of compound 77 (10.8 mg, 4.73 µmol) in saturated sodium hydrogen carbonate solution (472 µL) are successively added, at 0° C. and under an inert atmosphere, solid sodium hydrogen carbonate (64 mg) and acetic anhydride (36 µL). After stirring for 18 hours at room temperature, the reaction mixture is filtered (Millipore® LSWP 5 µm filter) and then applied to a column of fine Sephadex® G-25 gel eluted with aqueous 0.2 M NaCl solution. The fractions containing the expected product are pooled and applied to a column of fine Sephadex® G-25 (95×2 cm) eluted with water, to give 6.7 mg of compound 7.

$^1$H NMR (D$_2$O) δ of the anomeric protons: 5.20; 5.18 (2H); 5.17 (2H); 5.16; 5.15; 4.78 ppm.

Mass: "ESI" method, negative mode: theoretical mass=2453.62; experimental mass: 2453.22±0.17 a.m.u.

Example 8

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (Compound 8)

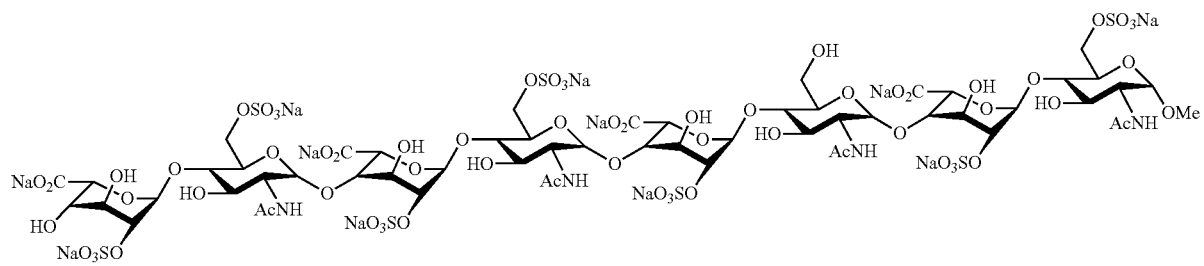

Compound 85 (23.0 mg, 11.1 μmol) is treated according to the same procedure as that described for the preparation of compound 7, to give compound 8 (25.2 mg).

$^1$H NMR (D$_2$O) δ of the anomeric protons: 5.45; 5.42 (2H); 5.22; 5.21; 5.20; 5.18; 5.03 ppm.

Mass: "ESI" method, negative mode: theoretical mass=2249.53; experimental mass: 2249.19±0.18 a.m.u.

Example 9

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-2-acetamido-2-deoxy-α-D-glucopyranoside (Compound 9)

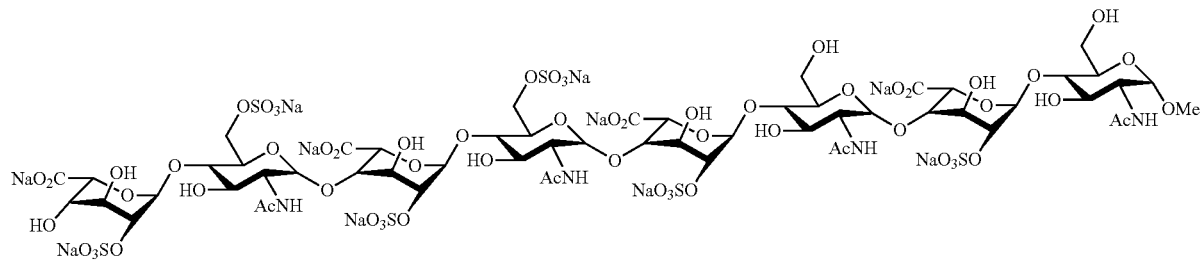

Compound 90 (52.1 mg, 23.9 μmol) is treated according to the same procedure as that described for the preparation of Example 7, to give compound 9 (50.7 mg).

$^1$H NMR (D$_2$O) δ of the anomeric protons: 5.18; 5.16 (2H); 5.14; 5.15; 5.13; 5.09; 4.75 ppm.

Mass: "ESI" method, negative mode: theoretical mass=2351.57; experimental mass: 2350.88±0.10 a.m.u.

Example 10

Methyl (sodium 2-O-sodium sulfonato-α-L-idopyranosyluronate)-4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (Compound 10)

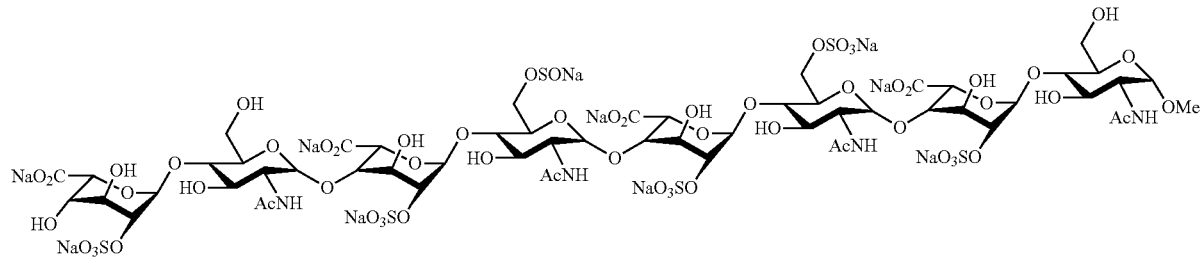

To a saturated aqueous sodium hydrogen carbonate solution (3.7 mL) of compound 100 (76 mg, 37 μmol) is added sodium hydrogen carbonate (497 mg, 5.92 mmol), followed by dropwise addition, at 0° C., of acetic anhydride (283 μL, 3.0 mmol). After stirring vigorously for 3 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 10 (61 mg, 73%).

Chemical shifts of the anomeric protons (600 MHz, D$_2$O) δ 5.13 IdoUA$^{VIII}$, 5.13 Glc$^{VII}$, 5.15 IdoUA$^{VI}$, 5.13 Glc$^{V}$, 5.16 IdoUA$^{IV}$, 5.10 Glc$^{III}$, 5.16 IdoUA$^{II}$, 4.75 Glc$^{I}$ Mass: "ESI" method, negative mode: theoretical mass=2249.53; experimental mass: 2249.02±0.35 a.m.u.

Example 11

Methyl (sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (Compound 11)

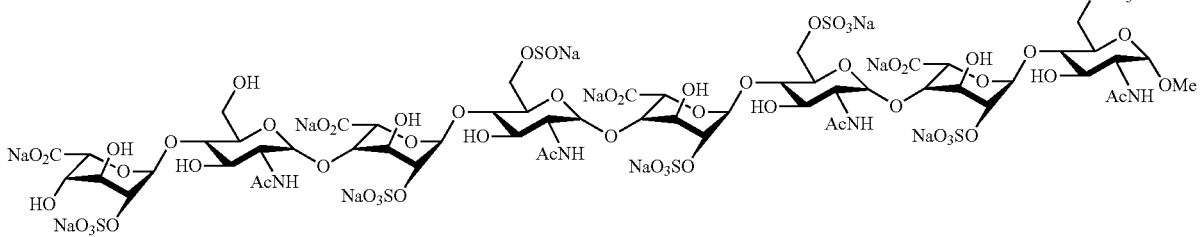

To a saturated aqueous sodium hydrogen carbonate solution (2.6 mL) of compound 105 (56 mg, 26 μmol) is added sodium hydrogen carbonate (349 mg, 4.16 mmol), followed by dropwise addition, at 0° C., of acetic anhydride (194 μL, 2.05 mmol). After stirring vigorously for 3 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 11 (45 mg, 74%).

Chemical shifts of the anomeric protons (600 MHz, D$_2$O) δ 5.13 IdoUA$^{VIII}$, 5.12 Glc$^{VII}$, 5.16 IdoUA$^{VI}$, 5.12 Glc$^{V}$, 5.15 IdoUA$^{IV}$, 5.13 Glc$^{III}$, 5.17 IdoUA$^{II}$, 4.72 Glc$^{I}$ Mass: "ESI" method, negative mode: theoretical mass=2351.57; experimental mass: 2351.13±0.06 a.m.u.

Example 12

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyl uronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (Compound 12)

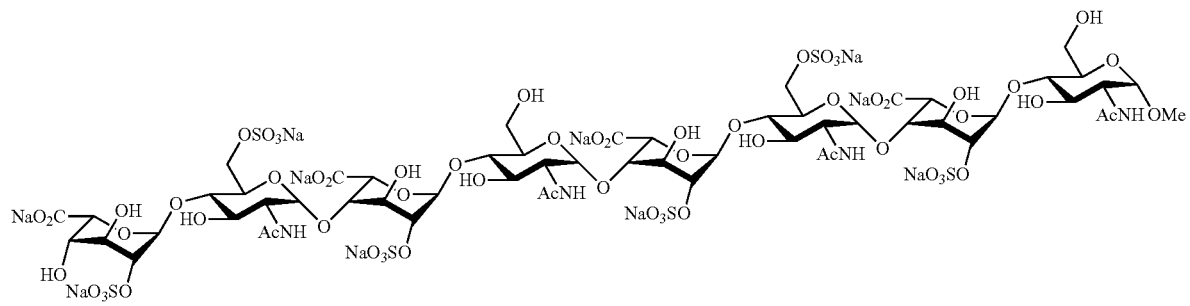

To a saturated aqueous sodium hydrogen carbonate solution (1.4 mL) of compound 113 (29.5 mg, 14 µmol) is added sodium hydrogen carbonate (188 mg, 2.24 mmol), followed by dropwise addition, at 0° C., of acetic anhydride (105 µL, 1.12 mmol). After stirring vigorously for 3 hours at 0° C. and then for 15 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 12 (29 mg, 92%).

Chemical shifts of the anomeric protons (600 MHz, $D_2O$) δ 5.12 IdoUA$^{VIII}$, 5.06 Glc$^{VII}$, 5.14 IdoUA$^{VI}$, 5.11 Glc$^{V}$, 5.13 IdoUA$^{IV}$, 5.09 Glc$^{III}$, 5.14 IdoUA$^{II}$, 4.73 Glc$^{I}$ $[α]_D$ 115.3° (c 0.3; $H_2O$).

Example 13

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (Compound 13)

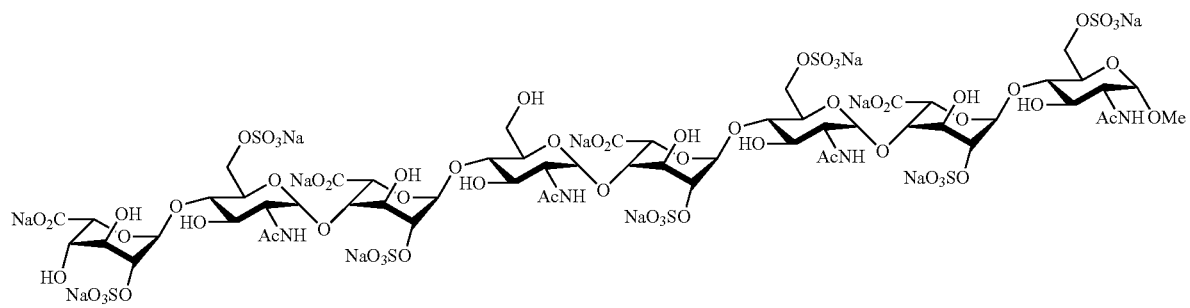

To a saturated aqueous sodium hydrogen carbonate solution (1.26 mL) of compound 118 (27 mg, 12.6 μmol) is added sodium hydrogen carbonate (169 mg, 2.02 mmol), followed by dropwise addition, at 0° C., of acetic anhydride (95 μL, 1.01 mmol). After stirring vigorously for 3 hours at 0° C. and then for 16 hours at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 13 (26.5 mg, 89%).

Chemical shifts of the anomeric protons (600 MHz, D$_2$O) δ 5.12 IdoUA$^{VIII}$, 5.05 Glc$^{VII}$, 5.13 IdoUA$^{VI}$, 5.10 Glc$^{V}$, 5.13 IdoUA$^{IV}$, 5.10 Glc$^{III}$, 5.14 IdoUA$^{II}$, 4.72 Glc$^{I}$ Mass: "ESI" method, negative mode: theoretical mass=2351.57; experimental mass: 2350.96±0.20 a.m.u.

Example 14

5-phenylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (Compound 14)

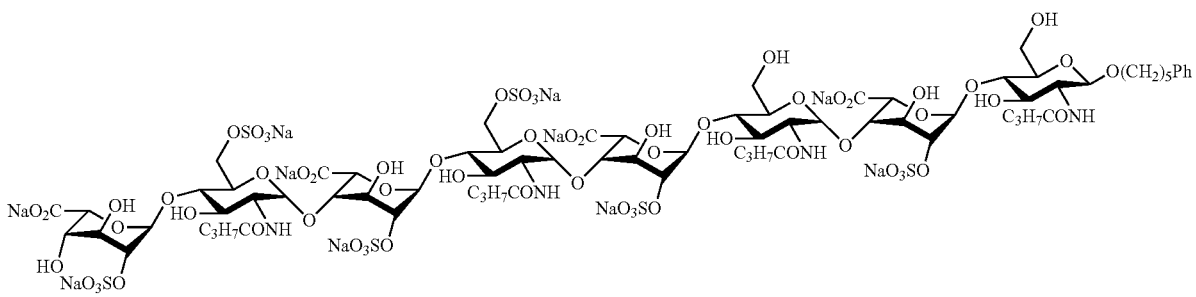

To a solution of compound 171 (126 mg, 56.9 µmol) in a 7/3 mixture of N,N-dimethylformamide/water (12.6 mL) are added dropwise, at 0° C., diisopropylethylamine (148 µL, 14.9 molar equivalents) dissolved in N,N-dimethylformamide (100 µL), and N-hydroxysuccinimide butyrate (116 mg, 11 molar equivalents) dissolved in N,N-dimethylformamide (100 µL). Stirring is continued at room temperature for 3 hours, and the same amount of reagent is then added three times under the same conditions. After a total of 23 hours of stirring at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 14 (133 mg, 93%).

Chemical shifts of the anomeric protons (600 MHz, $D_2O$)
δ 5.07 IdoUA$^{VIII}$, 4.99 Glc$^{VII}$, 5.09 IdoUA$^{VI}$, 5.04 Glc$^{V}$, 5.10 IdoUA$^{IV}$, 5.01 Glc$^{III}$, 5.06 IdoUA$^{II}$, 4.38 Glc$^{I}$ $[\alpha]_D$ 50.5° (c 1; $H_2O$).

Example 15

2-propylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (Compound 15)

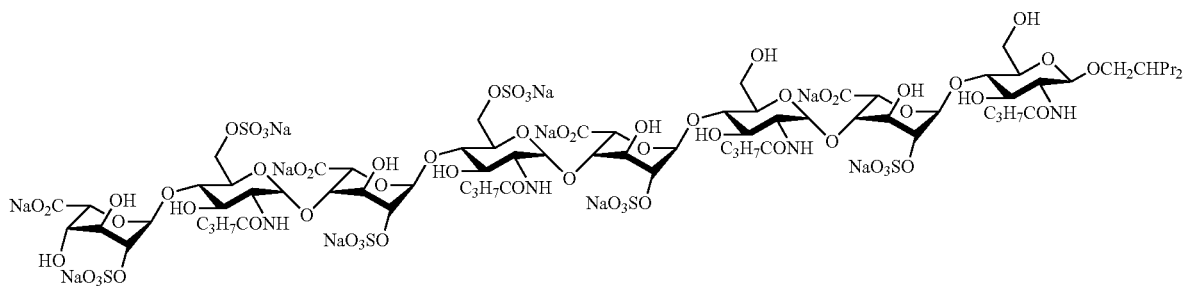

Compound 172 (47 mg, 22 µmol) is treated according to a protocol similar to that described for the synthesis of 14, to give compound 15 (46 mg, 85%).

Chemical shifts of the anomeric protons (600 MHz, $D_2O$) δ 5.33 IdoUA$^{VIII}$, 5.30 Glc$^{VII}$, 5.35 IdoUA$^{VI}$, 5.24 Glc$^V$, 5.36 IdoUA$^{IV}$, 5.27 Glc$^{III}$, 5.32 IdoUA$^{II}$, 4.63 Glc$^I$ $[α]_D$ 60° (c 1; $H_2O$).

Example 16

3-cyclohexylpropyl (sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-α-D-glucopyranosyl)-(1→4)-(sodium 2-O-sodium sulfonato-α-L-idopyranosyluronate)-(1→4)-2-deoxy-2-acetamido-β-D-glucopyranoside (Compound 16)

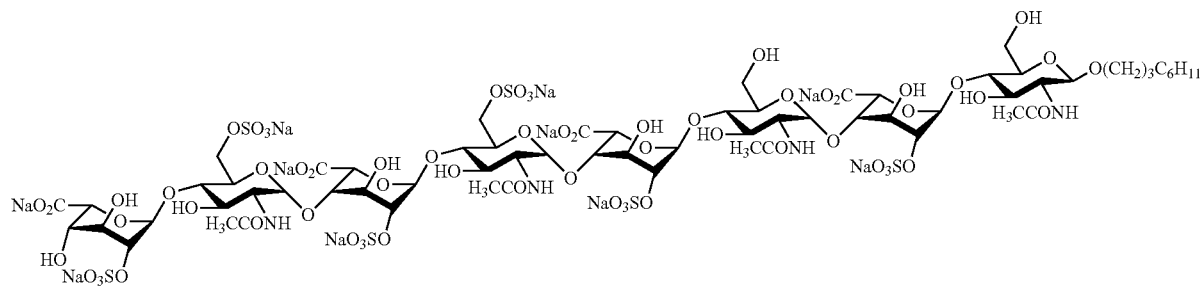

Compound 172 (10 mg, 4.56 µmol) is treated according to a protocol similar to that described for the synthesis of 13, to give compound 16 (8.8 mg, 82%).

Chemical shifts of the anomeric protons (600 MHz, $D_2O$) δ 5.15 IdoUA$^{VIII}$, 5.08 Glc$^{VII}$, 5.17 IdoUA$^{VI}$, 5.13 Glc$^V$, 5.17 IdoUA$^{IV}$, 5.11 Glc$^{III}$, 5.16 IdoUA$^{II}$, 4.50 Glc$^I$ $[α]_D$ +40.9° (c 0.88; $H_2O$).

Example 17

3-cyclohexylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)-amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (Compound 17)

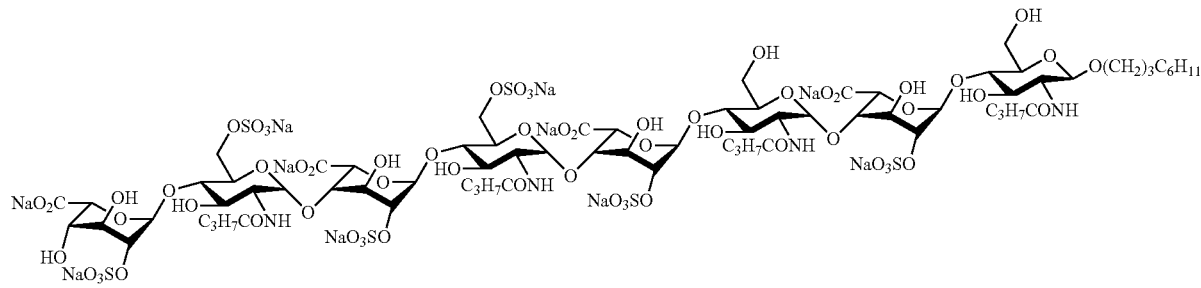

Compound 173 (10 mg, 4.56 μmol) is treated according to a protocol similar to that described for the synthesis of 14, to give compound 17 (7.7 mg, 69%).

Chemical shifts of the anomeric protons (600 MHz, $D_2O$) δ 5.23 IdoUA$^{VIII}$, 5.20 Glc$^{VII}$, 5.25 IdoUA$^{VI}$, 5.15 Glc$^{V}$, 5.26 IdoUA$^{IV}$, 5.17 Glc$^{III}$, 5.22 IdoUA$^{II}$, 4.57 Glc$^{I}$ $[α]_D$ +53.8° (c 0.77; $H_2O$).

Example 18

3,3-diphenylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)-amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (Compound 18)

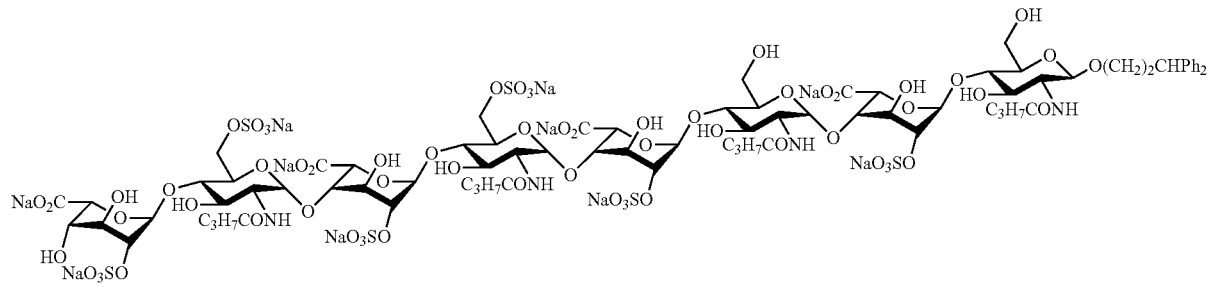

To a solution of compound 174 (5.5 mg, 2.4 μmol) in a 2/1 mixture of N,N-dimethylformamide/water (4.8 mL) are added dropwise, at 0° C., diisopropylethylamine (63 μL, 15 molar equivalents) dissolved in N,N-dimethylformamide (43 μL), and N-hydroxysuccinimide butyrate (49 mg, 11 molar equivalents) dissolved in N,N-dimethylformamide (43 μL). Stirring is continued at room temperature for 3 hours, and the same amount of reagent is then added three times under the same conditions. After a total of 24 hours of stirring at room temperature, the reaction medium is applied to a Sephadex® G-25 column eluted with 0.2 M sodium chloride. The fractions containing the product are concentrated and desalified using the same column eluted with water. The fractions containing the product are then concentrated under high vacuum to give the desired compound 18 (6 mg, 98%).

Chemical shifts of the anomeric protons (600 MHz, $D_2O$) δ 5.22 IdoUA$^{VIII}$, 5.19 Glc$^{VII}$, 5.23 IdoUA$^{VI}$, 5.13 Glc$^{V}$, 5.23 IdoUA$^{IV}$, 5.17 Glc$^{III}$, 5.20 IdoUA$^{II}$, 4.48 Glc$^{I}$ $[\alpha]_D$ +24° (c 0.48, $H_2O$).

Example 19

5-phenylpentyl (sodium 2-O-sodium sulfonato-α-L-idopyranosyluronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(3-methyl-1-oxobutyl)amino-α-D-glucopyranosyl)-(1→4)-(sodium 2-O-sodium sulfonato-α-L-idopyranosyluronate)-(1→4)-2-deoxy-2-(3-methyl-1-oxobutyl)amino-β-D-glucopyranoside (Compound 19)

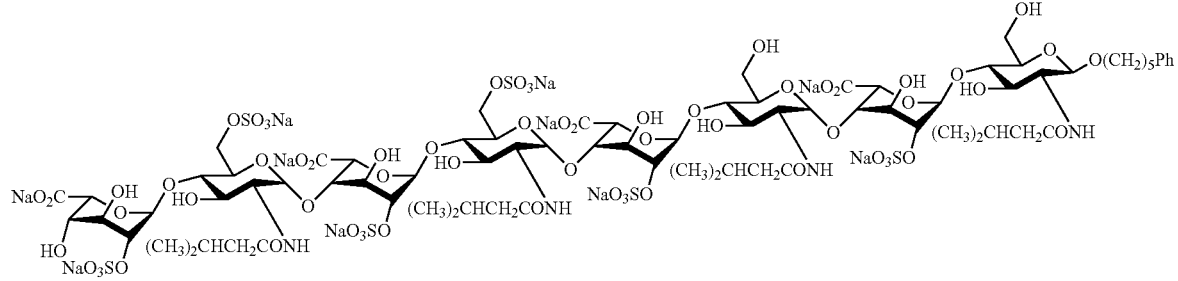

A solution of compound 171 (84 mg, 37.8 μmol) in a 7/3 mixture of N,N-dimethylformamide/water (8.4 mL) is treated with 1-[(3-methylbutanoyl)oxy]pyrrolidine-2,5-dione according to a process similar to the synthesis of compound 14, to give the desired compound 19 (41.8 mg, 43%). If necessary, it may be purified by ion-exchange chromatography using a semi-preparative Dionex CarboPac® PA100 column (9×250 mm) with a gradient starting from an eluent A to an eluent B, eluent A consisting of a water/acetonitrile mixture (4/1)+0.01% of dimethyl sulfoxide, and eluent B consisting of a mixture of a 2N sodium chloride solution and acetonitrile (4/1). The fractions containing the product are then concentrated and desalified using a Sephadex® G-25 column eluted with water. The fractions containing the product are then concentrated under high vacuum to give the desired pure compound 19.

Chemical shifts of the anomeric protons (600 MHz, $D_2O$) δ 5.23 IdoUA$^{VIII}$, 5.19 Glc$^{VII}$, 5.24 IdoUA$^{VI}$, 5.13 Glc$^{V}$, 5.25 IdoUA$^{IV}$, 5.17 Glc$^{III}$, 5.22 IdoUA$^{II}$, 4.55 Glc$^{I}$ "ESI" method, negative mode: multicharged ion detected m/z 581.3517 $[M-4H]^{4-}$ (acid form).

The compounds according to the invention underwent pharmacological trials to determine their agonist effect on the FGF receptors and their activity on angiogenesis and also on post-ischaemic revascularization.

Model of In Vitro Angiogenesis: Specific Activity Towards FGF2

The in vitro angiogenesis model corresponds to a rearrangement of human venous endothelial cells on a biological matrix. The matrix is made by dispensing, into each well of a 96-well plate (Becton Dickinson 353872), 60 μl of Matrigel® diluted to 1/3 (Growth factor reduced Matrigel®: Becton Dickinson 356230) in collagen (rat tail collagen, type I: Becton Dickinson 354249). The biological matrix hardens after 1 hour at 37° C.

Human venous endothelial cells (HUVEC ref: C-12200–Promocell) are seeded onto the biological matrix at 7800 cells/well in 120 μl of EBM® medium (Endothelial Basal Medium, Lonza C3121)+2% FCS (foetal calf serum–Lonza)+hEGF (Recombinant Human Epidermal Growth Factor–Lonza) 10 μg/ml. The cells are stimulated with FGF2 (R&D Systems/234–FSE–0 50) 10 ng/ml or with the products of the invention for 18 hours at 37° C. in the presence of 5% $CO_2$. After 24 hours, the cells are observed under a microscope (×4 objective lens) and analysis of the length of the pseudo-tubules is performed with the aid of image software (Biocom VisioLab 2000 software).

In this test of in vitro angiogenesis, the compounds of the invention have a specific activity of between $10^{-6}$ M and $10^{-12}$ M. For example, compounds 1 and 2 are active at $10^{-11}$ M.

Model of Cellulose Implant in Mice

This model is an adaptation of the model described by Andrade et al. (Microvascular Research, 1997, 54, 253-61) for testing pharmacological products capable of activating the onset of angiogenesis.

The animals (white consanguineous BALB/c J mice) are anaesthetized with a xylazine (Rompun®, 10 mg/kg)/ketamine (Imalgene® 1000, 100 mg/kg) mixture intraperitoneally. The animal's back is shaved and disinfected with Hexomedine®. An air pocket is created subcutaneously on the mouse's back by injecting 5 ml of sterile air. An incision of about 2 cm at the top of the animal's back is made in order to introduce a sterile cellulose implant (disk 1 cm in diameter, 2 mm thick, Cellspon® ref. 0501) impregnated with 50 μl of sterile solution containing the test product. The incision is then sutured and cleaned with Hexomedine®.

On the days following the insertion of the implant, the mice can receive the product into the implant via an injection through the skin (50 μl/implant/day) under gaseous anaesthesia (5% isoflurane (Aerrane®, Baxter)).

Seven days after inserting the sponge, the mice are sacrificed by means of a lethal dose of pentobarbital sodium (CEVA Santé Animale), administered intraperitoneally. The skin is then excised, about 1 cm around the sponge, while avoiding the scar, so as to release the skin and the sponge. The sponge is then cut into several pieces and placed in a Ribolyser® containing 1 ml of lysis buffer (Cell Death Detection ELISA, Roche). The tubes are shaken four times consecutively, for 20 seconds, at force 4, using a cell mill (FastPrep® FP 120). The tubes are then centrifuged for 10 minutes at 2000×g at 20° C. and the supernatants are frozen at −20° C. until the time of the haemoglobin assay. On the day of the assay, the tubes are again centrifuged after thawing and the haemoglobin concentration is measured with the Drabkin reagent (Sigma, volume for volume) by reading on a spectrophotometer at 405 nm against a standard range of bovine haemoglobin (Sigma).

The haemoglobin concentration in each sample is expressed in mg/ml from the polynomial regression produced from the range. The results are expressed as a mean value (±sem) for each group. The differences between the groups are tested with an ANOVA followed by a Dunnett test on the square root of the values.

In this in vivo test, the compounds of the invention revealed a specific activity of between 5 and 45 ng/site. For example, compounds 1 and 2 are active at 45 ng/site, and compound 7 is active at 15 ng/site.

For comparative purposes relative to a compound analogous to compound 7 according to the invention, but in which all the —NH-acyl groups are replaced with —NH—SO$_3$— groups, compound 7 according to the invention has in this test an activity of greater than 21% relative to the said fully sulfated analogue, which shows the importance of the N-acyl groups in the compounds according to the invention.

Pharmacokinetics

The pharmacokinetic profile of the compounds according to the invention is evaluated after cutaneous administration, to OF1 or C57/BL6 mice, at a concentration of 30 mg/kg. The systemic exposure of the compounds is evaluated after a single administration to the animal anaesthetized beforehand with pentobarbital. The blood is collected from the vena cava and then transferred into plastic tubes containing lithium heparin. After centrifugation (2000×g for 10 minutes at 8° C.), the concentration of the compounds in the plasma is quantified by LC/MS-MS.

In general, the test compounds have an improved pharmacokinetic profile (especially higher AUC and plasmatic concentration, and longer half-lives) relative to fully sulfated analogous compounds (replacement of the N-acyl groups with —NH—SO$_3$— groups). By way of example, the pharmacokinetic parameters of compounds 1, 6 and 7 according to the invention are described in the table that follows, in comparison with a fully sulfated analogue No. 175 having the following formula:

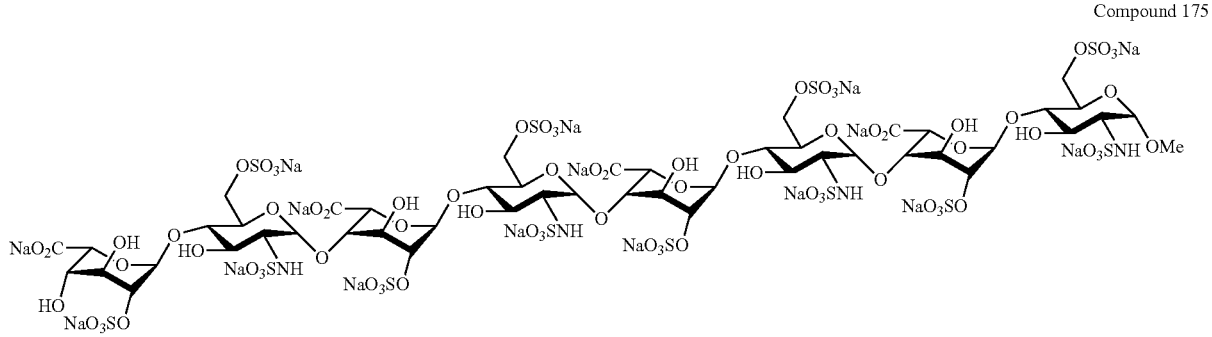

Compound 175

| Compound | AUC (0-Clast) (ng · h/mL) | $T_{1/2}$ (h) | Plasma conc., t = 4 h (ng/mL) |
|---|---|---|---|
| No. 1 | 18 000 | 1 | 924 |
| No. 6 | 95 000 | 0.46 | 5740 |
| No. 7 | 22 000 | 0.40 | 425 |
| No. 175 | 15 000 | 0.33 | 20 |

AUC (0-tlast): Area under the curve between time 0 (compound administration start time) and tlast (the time of the last measurement).
$T_{1/2}$ (h): half-life time
Plasma conc., t = 4 h: Plasmatic concentration at 4 hours These results show the importance of the N-acyl groups in the compounds according to the invention, which make them particularly suitable for use as medicaments.

It emerges from the foregoing that the compounds according to the invention have agonist activity on the FGF receptors and activity on angiogenesis, and also on post-ischaemic revascularization. The compounds according to the invention may thus be used for the preparation of medicaments, especially medicaments that are useful for treating diseases that require activation of the FGF receptors, or of medicaments that are useful in pathologies requiring activation of angiogenesis post-ischaemic revascularization.

Thus, according to another of its aspects, a subject of the invention is thus medicaments that comprise a compound of formula (I)/(I') according to the invention, or a pharmaceutically acceptable salt thereof.

These medicaments find their use in therapy, especially in the treatment of ischaemia (cardiac ischaemia, arterial ischaemia of the lower limbs), the treatment of diseases associated with narrowing or obstruction of the arteries or arterites, the treatment of angina pectoris, the treatment of thromboangitis obliterans, the treatment of atherosclerosis, the treatment of inhibition of restenosis after angioplasty or endoarterectomy, the treatment of cicatrization, muscle regeneration treatment, treatment for the survival of myoblasts, the treatment of peripheral neuropathy, the treatment of post-operative nerve damage, the treatment of nerve deficiencies such as Parkinson's disease, Alzheimer's disease, prion disease and neuronal degeneration in alcoholics, the treatment of dementias, treatment for improving the survival of a bioartificial pancreas graft in the case of diabetics, treatment for improving the revascularization of grafts and the survival of grafts, the treatment of retinal degeneration, the treatment of pigmentary retinitis, the treatment of osteoarthritis, the treatment of pre-eclampsia or the treatment of vascular lesions and of acute respiratory distress syndrome, treatment for cartilage repairing, treatment for repairing and protecting bones, treatment for repairing and protecting hair follicles and for protecting and regulating hair growth.

Ischaemia is a decrease in arterial circulation in an organ, leading to a decrease in oxygen concentration in the damaged tissues. In the mechanisms of post-ischaemic revascularization, two main mechanisms are involved: angiogenesis and arteriogenesis. Angiogenesis is the process of generating new blood capillaries from pre-existing vessels. Arteriogenesis contributes towards the development (increase in size and calibre) of the collateral vessels around the ischaemic or avascular area.

Among the growth factors involved in these revascularization processes, the FGF family and especially FGF-2 has been the most widely described (Post, M. J., Laham, R., Sellke, F. W. & Simons, M. Therapeutic angiogenesis in cardiology using protein formulations. Cardiovasc. Res. 49, 522-31, 2001). Thus, FGF2 and its receptors represent very pertinent targets for therapies directed towards inducing angiogenesis and arteriogenesis processes (Khurana, R. & Simons, M. Insights from angiogenesis trials using fibroblast growth factor for advanced arteriosclerotic disease. Trends Cardiovasc. Med. 13, 116-22, 2003).

One of the applications of the compounds of the invention is post-ischaemic treatment after heart occlusion or occlusion of the peripheral arteries. As regards the treatment of cardiac ischaemia, one of the most promising clinical tests is a clinical test in which FGF-2 was sequestered in alginate microspheres in the presence of heparin (Laham, R. J. et al. Local perivascular delivery of basic fibroblast growth factor in patients undergoing coronary bypass surgery: results of a phase I randomized, double-blind, placebo-controlled trial. Circulation 100, 1865-71, 1999). These microspheres were implanted close to the ischaemic locus in the myocardium. After 90 days, all the patients treated with FGF2 showed no ischaemic cardiac symptoms. In comparison, in the control group, three of the seven patients had persistent symptoms at 90 days and two patients required vascular surgery. Interestingly, the therapeutic benefit was maintained after 3 years of monitoring. These observations suggest that compounds that mimic FGF2 may represent a therapy of choice for treating the consequences of cardiac ischaemia.

Three clinical tests on the injection of FGF2 into the coronary artery were performed during treatment of narrowing of the coronary arteries (Laham, R. J. et al. Intracoronary basic fibroblast growth factor (FGF-2) in patients with severe ischemic heart disease: results of a phase I open-label dose escalation study. J. Am. Coll. Cardiol. 36, 2132-9, 2000; Simons, M. et al. Pharmacological treatment of coronary artery disease with recombinant fibroblast growth factor-2: double-blind, randomized, controlled clinical trial. Circulation 105, 788-93, 2002; Unger, E. F. et al. Effects of a single intracoronary injection of basic fibroblast growth factor in stable angina pectoris. Am. J. Cardiol. 85, 1414-9, 2000). The result of these three tests shows that intracoronary infusions of FGF2 are well tolerated and significantly improve the condition of the patients. Thus, the compounds described in the invention may find an application in the treatment of diseases associated with narrowing of the coronary arteries and especially in the treatment of angina pectoris.

Diseases of the distal arteries and especially arteritis of the lower limbs are caused by chronic obstruction of the arterioles that irrigate the extremities. These pathologies mainly affect the lower limbs. In a phase I clinical trial, patients with peripheral artery pathologies leading to claudication received injections of FGF2 (Lazarous, D. F. et al., Basic fibroblast growth factor in patients with intermittent claudication: results of a phase I trial. J. Am. Coll. Cardiol. 36, 1239-44, 2000). In this context, FGF2 was well tolerated in these patients and the clinical data suggest a beneficial effect of FGF2 and especially on improving walking. These clinical data suggest that the compounds of the invention represent a therapeutic tool of choice for the treatment of diseases associated with obstruction of the distal arteries.

Buerger's disease or thromboangitis obliterans affects the distal vascular structures and is characterized by distal arteritis of the legs, with pain and ulceration. In this context, an induction of angiogenesis and of vasculogenesis would represent a therapy for this pathology. The compounds of the said invention represent a therapy of choice for thromboangitis obliterans.

Peripheral neuropathy is an axonal or demyelinizing attack of the motor and/or sensory peripheral nerve which leads to desensitization of the distal limbs. One of the major secondary complications of diabetes is the chronic development of peripheral neuropathy. In this context, it has been demonstrated that FGF2 induces axonal regeneration, which might be a therapy of choice in the treatment of peripheral nerve lesion and thus in peripheral neuropathy (Basic fibroblast growth factor isoforms promote axonal elongation and branching of adult sensory neurons in vitro. Klimaschewski L, Nindl W, Feurle J, Kavakebi P, Kostron H. Neuroscience. 2004; 126(2):347-53). By virtue of the agonist activity on the FGF receptors, the compounds of the said invention would represent a treatment of choice in peripheral neuropathy in the case of healthy or diabetic patients.

It is clearly established that FGF2 is an activator of nerve cells during development. Recent results suggest that FGF2 is also a pivotal factor for promoting the regeneration of neurons in adults (Sapieha P S, Peltier M, Rendahl K G, Manning W C, Di Polo A., Fibroblast growth factor-2 gene delivery stimulates axon growth by adult retinal ganglion cells after acute optic nerve injury. Mol. Cell. Neurosci. 2003 November; 24(3):656-72.). By virtue of their agonist activities on the FGF receptors, the compounds of the said invention would represent a treatment of choice in repairing post-operative nerve damage, in repairing nerve deficiencies such as Parkinson's disease, Alzheimer's disease, prion disease and neuronal degeneration in alcoholics or in the case of dementia.

The proliferation and migration of vascular smooth muscle cells contributes towards intimal hypertrophy of the arteries and thus plays a predominant role in atherosclerosis and in restenosis after angioplasty and endoarterectomy. It has been demonstrated that an angiogenic factor, VEGF, significantly reduces the thickening of the intima by accelerating re-endothelialization (Van Belle, E., Maillard, L., Tio, F. O. & Isner, J. M. Accelerated endothelialization by local delivery of recombinant human vascular endothelial growth factor reduces in-stent intimal formation. Biochem. Biophys. Res. Commun. 235, 311-6, 1997). Thus, the compounds of the present invention, with pro-angiogenic activity, may be useful in treatment of atherosclerosis and in inhibiting restenosis after angioplasty or endoarterectomy.

The vascular network is essential to the development and maintenance of tissues. By promoting the delivery of nutrients, oxygen and cells, the blood vessels help to maintain the functional and structural integrity of tissues. In this context, angiogenesis and vasculogenesis make it possible to preserve and to perfuse tissues after ischaemia. The angiogenic growth factors such as VEGF and FGF2 thus promote revascularization for tissue regeneration. The compounds presented in the invention could represent a treatment of choice in muscle regeneration treatment.

The processes of muscle regeneration on dystrophic or normal muscles depend on the supply of cytokines and of angiogenic growth factors at the local level (Fibbi, G., D'Alessio, S., Pucci, M., Cerletti, M. & Del Rosso, M. Growth factor-dependent proliferation and invasion of muscle satellite cells require the cell-associated fibrinolytic system. Biol. Chem. 383, 127-36, 2002). It has been proposed that the FGF system is a critical system of muscle regeneration and of myoblast survival and proliferation (Neuhaus, P. et al. Reduced mobility of fibroblast growth factor (FGF)-deficient myoblasts might contribute to dystrophic changes in the musculature of FGF2/FGF6/mdx triple-mutant mice. Mol. Cell. Biol. 23, 6037-48, 2003). FGF2 and the compounds of the said invention could be exploited in order to promote cardiac regeneration. They would thus improve the perfusion of the myocardium after ischaemia (Hendel, R. C. et al. Effect of intracoronary recombinant human vascular endothelial growth factor on myocardial perfusion: evidence for a dose-dependent effect. Circulation 101, 118-21, 2000) and also the survival and progress of transplanted myoblasts, especially in Duchenne's muscular dystrophy.

Angiogenesis is an essential phenomenon during cutaneous cicatrization. The new vessels formed supply the oxygen and nutrients required for tissue repair. In the case of diabetics, cicatrization is a slow and difficult process presenting angiogenesis defects. FGFs are among the growth factors that are the most involved in angiogenesis processes during the cicatrization phase. Certain FGFs are highly overregulated in dermal cells after a cutaneous injury. On account of their agonist activity on the FGF receptors, the compounds of the said invention would represent a therapy of choice for the treatment of cicatrization in healthy or diabetic patients.

Bioartificial pancreas transplantation is a very promising technique for the treatment of certain types of diabetes. It has been demonstrated, in diabetic rats, that vascularization in bioartificial pancreases is much greater when the pancreases are impregnated with microspheres bearing FGF2 (Sakurai, Tomonori; Satake, Akira, Sumi, Shoichiro, Inoue, Kazutomo, Nagata, Natsuki, Tabata, Yasuhiko. The Efficient Prevascularization Induced by Fibroblast Growth Factor 2 With a Collagen-Coated Device Improves the Cell Survival of a Bioartificial Pancreas. Pancreas. 28(3):e70-e79, April 2004). This revascularization thus improves the survival of implanted bioartificial pancreases and consequently the survival of the graft. By virtue of their agonist activities on the FGF receptors, the compounds of the said invention would represent a therapy of choice in improving the survival of bioartificial pancreas grafts in diabetics and more generally in improving the revascularization of grafts and consequently the survival of the grafts.

Pigmentary retinitis is a pathology involving progressive degeneration of the retina characterized by degeneration of the photoreceptors and obliteration of the retinal vessels. Landenranta et al. (An anti-angiogenic state in mice and humans with retinal photoreceptor cell degeneration. Proc. Natl. Acad. Sci. USA 98, 10368-73, 2001) have proposed that angiogenic growth factors regulate the neural coordination and the associated vascularization of the retina by simultaneously functioning as photoreceptor survival factors and as endothelial cell regulators. In this context, the intra-vitreal injection of FGF2 retards the degeneration of the photoreceptors by acting on retinal survival and retinal angiogenesis (Faktorovich, E. G., Steinberg, R. H., Yasumura, D., Matthes, M. T. & LaVail, M. M. Basic fibroblast growth factor and local injury protect photoreceptors from light damage in the rat. J. Neurosci. 12, 3554-67, 1992). These observations demonstrate the interest of the compounds described in the invention as a therapy in retinal degeneration and especially in pigmentary retinitis.

In the field of osteoarthritis, many studies have been performed for restoring destroyed articular cartilage. In this context, it has been reported that the proliferation and differentiation of chondrocytes were stimulated by FGF2 in vitro (Kato Y, Gospodarowicz D. Sulfated proteoglycan synthesis by confluent cultures of rabbit costal chondrocytes grown in the presence of fibroblast growth factor. J. Cell Biol. 1985 February; 100(2):477-85). Furthermore, Cuevas et al. have shown that FGF2 induces cartilage repair in vivo (Cuevas P, Burgos J, Baird A. Basic fibroblast growth factor (FGF) promotes cartilage repair in vivo. Biochem. Biophys. Res. Commun. 1988 Oct. 31; 156(2):611-8). Takafuji et al. have also shown that FGF2 implants significantly improve temporomandibular cartilage in rabbits suffering from osteoarthritis (Takafuji H, Suzuki T, Okubo Y, Fujimura K, Bessho K Regeneration of articular cartilage defects in the temporomandibular joint of rabbits by fibroblast growth factor-2: a pilot study. Int. J. Oral Maxillofac. Surg. 2007 October; 36(10):934-7). These observations demonstrate the interest the compounds described in the invention as a therapy in treatment of osteoarthritis and cartilage repair.

In the field of bone repair, one of the essential needs is to find agents that stimulate bone formation. Among the main growth factors, it is established that the systemic administration of FGF2 facilitates bone repair (Acceleration of fracture healing in nonhuman primates by fibroblast growth factor-2. Kawaguchi H, Nakamura K, Tabata Y, Ikeda Y, Aoyama I, Anzai J, Nakamura T, Hiyama Y, Tamura M. J. Clin. Endocrinol. Metab. 2001 February; 86(2), 875-880). The local application of FGF2 in gelatin matrices accelerates bone repair in primates, suggesting the clinical utility of FGF2 in the treatment of fractures. By virtue of their agonist properties for the FGF receptors, the compounds of the said invention would represent a treatment of choice in bone repair.

Pre-eclampsia is a pathology of the placenta associated with a vascularization defect (Sherer, D. M. & Abulafia, O. Angiogenesis during implantation, and placental and early embryonic development. Placenta 22, 1-13, 2001). These vascularization defects are thought to be due to an angiogenesis defect and lead to placental disruptions that may result in the death of the fetus. The compounds of the invention may be a treatment of choice for overcoming an angiogenesis defect in pre-eclamptic placentas.

In addition to angiogenesis-inducing effects, growth factors such as VEGF or FGF2 protect endothelial cells against intrinsic and extrinsic apoptosis inducers. The intrinsic signalling pathway is activated by the mitochondria in response to a stress such as deprivation or DNA damage, whereas the extrinsic signalling pathway is induced by the binding of pro-apoptotic factors such as TNF-$\alpha$ or Fas. It is now clearly described that VEGF and FGF2 are two factors of endothelial cell survival (Role of Raf in Vascular Protection from Distinct Apoptotic Stimuli: A Alavi, J. D. Hood, R. Frausto, D. G. Stupack, D. A. Cheresh: Science 4 Jul. 2003: Vol. 301. No. 5629, pp. 94-96). Acute respiratory distress syndrome (ARDS) is characterized by cardiovascular and neuropsychiatric problems. In the context of the cardiovascular problems, the patients present major vascular lesions and especially a high induction of apoptosis of endothelial cells. Recently, Hamacher et al. have demonstrated that the bronchoalveolar lavage fluids of patients suffering from ARDS showed pro-apoptotic activity against lung microvascular endothelial cells (Tumor necrosis factor-alpha and angiostatin are mediators of endothelial cytotoxicity in bronchoalveolar lavages of patients with acute respiratory distress syndrome. Am. J. Respir. Crit. Care Med. 2002 Sep. 1; 166(5):651-6: Hamacher J., Lucas R., Lijnen H. R., Buschke S., Dunant Y., Wendel A., Grau G. E., Suter P. M., Ricou B.). By virtue of their activity on endothelial cell survival, the products of the invention might be a treatment of choice in the vascular improvement of patients suffering from vascular lesions and especially patients suffering from ARDS.

The endogenous overregulation of FGF7 (or KGF) and of FGF18 appears to be an important mechanism for promoting the proliferation, migration and protection of hair follicles in pathological cases or after a tumoral treatment (Comprehensive Analysis of FGF and FGFR Expression in Skin: FGF18 Is Highly Expressed in Hair Follicles and Capable of Inducing Anagen from Telogen Stage Hair Follicles. Mitsuko Kawano, Akiko Komi-Kuramochi, Masahiro Asada, Masashi Suzuki, Junko Oki, Ju Jiang and Toru Imamura). By virtue of their agonist activity on the FGF receptors, the compounds of the said invention might be a treatment of choice for repairing and protecting hair follicles and for protecting and regulating hair growth.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient. The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I)/(I') above or the salt thereof may be administered in a unit administration form, as a mixture with standard pharmaceutical excipients, to man and animals for the prevention or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

The injectable administration forms are particularly advantageous, conventionally comprising the active compound dissolved in water for injection, in the presence of sodium chloride. The unit dose of active compound should be suited to the desired therapeutic effect; it may be, for example, between 0.1 and 100 mg of active principle.

According to another of its aspects, the present invention also relates to a method for treating the pathologies indicated above, which comprises the administration to patients of an effective dose of a compound according to the invention or a pharmaceutically acceptable salt thereof.

What is claimed is:

1. An octasaccharide compound corresponding to formula (I):

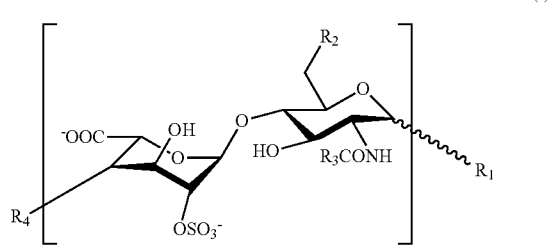

in which:
the wavy line denotes a bond located either below or above the plane of the pyranose ring of the glucosamine unit, $R_1$ represents a group O-alkyl, in which the alkyl group comprises from 1 to 16 carbon atoms and is optionally substituted with one or more groups, which may be identical or different, chosen from aryl and cycloalkyl groups, $R_2$ represents either a group $OSO_3^-$ or a hydroxyl group, $R_3$ represents an alkyl, cycloalkyl or alkyl-cycloalkyl group, and $R_4$ represents a disaccharide of formula (II):

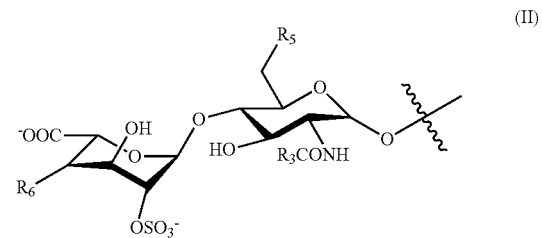

in which:
$R_3$ is as defined above, $R_5$ represents either a group $OSO_3^-$ or a hydroxyl group, and $R_6$ represents a disaccharide of formula (III):

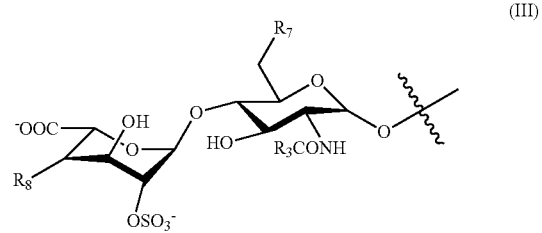

in which:
R$_3$ is as defined above,
R$_7$ represents either a group OSO$_3^-$ or a hydroxyl group, and
R$_8$ represents a disaccharide of formula (IV):

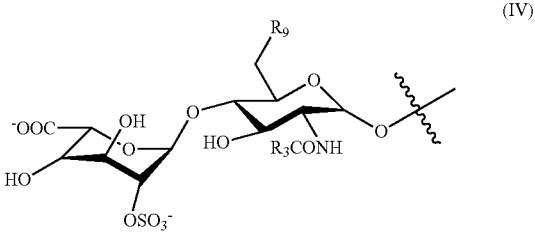

in which:
R$_3$ is as defined above,
R$_9$ represents either a group OSO$_3^-$ or a hydroxyl group,
in acid form or in the form of any pharmaceutically acceptable salt thereof.

2. A compound according to claim 1, in which R$_1$ represents:
either a group O-alkyl, in which the alkyl group comprises from 5 to 16 carbon atoms,
or a group O-alkyl, in which the alkyl group comprises from 1 to 8 carbon atoms and is substituted with 1 or 2 groups, which may be identical or different, chosen from aryl and cycloalkyl groups.

3. A compound according to claim 1, in which R$_1$ represents a group O-alkyl, in which the alkyl group comprises from 5 to 12 carbon atoms.

4. A compound according to claim 1, in which R$_1$ represents a group O-alkyl, in which the alkyl group comprises from 3 to 6 carbon atoms and is substituted with 1 or 2 groups, which may be identical or different, chosen from phenyl and cycloalkyl groups.

5. A compound according to claim 1, in which R$_3$ represents either an alkyl group comprising from 2 to 6 carbon atoms, or a cycloalkyl group.

6. A compound according to claim 1, in which at least one of the groups R$_2$, R$_5$, R$_7$ and R$_9$ represents a hydroxyl group.

7. A compound according to claim 1, in which at least one of the groups R$_2$, R$_5$, R$_7$ and R$_9$ represents a hydroxyl group and at least one of the groups R$_2$, R$_5$, R$_7$ and R$_9$ represents a group OSO$_3^-$.

8. A compound according to claim 1, selected from the group consisting of:
Pentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 1);
Pentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-2-deoxy-2-(1-oxobutyl)amino-6-O-sodium sulfonato-β-D-glucopyranoside (No. 2);
Pentyl (sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxohexyl)amino-6-O-sodium sulfonato-α-D-glucopyranosyl)-(1→4)-(sodium 2-O-sodium sulfonato-α-L-idopyranosyluronate)-(1→4)-2-deoxy-2-(1-oxohexyl)amino-6-O-sodium sulfonato-β-D-glucopyranoside (No. 3);
Pentyl (sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-(2-[(cyclopentylcarbonyl)amino]-2-deoxy-6-O-sodium sulfonato-α-D-glucopyranosyl)-(1→4)-(sodium 2-O-sodium sulfonato-α-L-idopyranosyluronate)-(1→4)-2-[(cyclopentylcarbonyl)amino]-2-deoxy-6-O-sodium sulfonato-β-D-glucopyranoside (No. 4);
Undecyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 5);
5-phenylpentyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-β-D-glucopyranoside (No. 6);
Methyl (sodium 2-O-sodium sulfonato-α-L-idopyranosyluronate)-(1→4)-(2-acetamido-2-deoxy-6-O-sodium sulfonato-α-D-glucopyranosyl)-[(1→4)-(sodium 2-O-sodium sulfonato-α-L-idopyranosyluronate)-(1→4)-(2-acetamido-2-deoxy-6-O-sodium sulfonato-α-D-glucopyranosyl)]$_2$-(1→4)-(sodium 2-O-sodium sulfonato-α-L-idopyranosyluronate)-(1→4)-2-acetamido-2-deoxy-6-O-sodium sulfonato-α-D-glucopyranoside (No. 7);
Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2- acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 8);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 9);

Methyl (sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (No. 10);

Methyl (sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 11);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-α-D-glucopyranoside (No. 12);

Methyl (sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-(2-acetamido-2-deoxy-α-D-glucopyranosyl)-(1→4)-(sodium 2-O-sodium sulfonato-α-L-idopyranosyluronate)-(1→4)-(2-acetamido-2-deoxy-6-O-sodium sulfonato-α-D-glucopyranosyl)-(1→4)-(sodium 2-O-sodium sulfonato-α-L-idopyranosyluronate)-(1→4)-2-acetamido-2-deoxy-6-O-sodium sulfonato-α-D-glucopyranoside (No. 13);

5-phenylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 14);

2-propylpentyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-8-D-glucopyranoside (No. 15);

3-cyclohexylpropyl (sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-6-O-sodium sulfonato-α-D-glucopyranosyl)-(1→4)-(sodium 2-O-sodium sulfonato-α-L-idopyranosyluronate)-(1→4)-(2-deoxy-2-acetamido-α-D-glucopyranosyl)-(1→4)-(sodium 2-O-sodium sulfonato-α-L-idopyranosyluronate)-(1→4)-2-deoxy-2-acetamido-β-D-glucopyranoside (No. 16);

3-cyclohexylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 17);

3,3-diphenylpropyl (sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(1-oxobutyl)amino-α-D-glucopyranosyl)-(1→4)-(sodium 2-O-sodium sulfonato-α-L-idopyranosyluronate)-(1→4)-2-deoxy-2-(1-oxobutyl)amino-β-D-glucopyranoside (No. 18); and 5-phenylpentyl (sodium 2-O-sodium sulfonato-α-L-idopyranosyluronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyl uronate)-(1→4)-(2-deoxy-2-(3-methyl-1-oxobutyl)amino-6-O-sodium sulfonato-α-D-glucopyranosyl)-(1→4)-(sodium 2-O-sodium sulfonato-α-L-idopyranosyluronate)-(1→4)-(2-deoxy-2-(3-methyl-1-oxobutyl)amino-α-D-glucopyranosyl)-(1→4)-(sodium 2-O-sodium sulfonato-α-L-idopyranosyluronate)-(1→4)-2-deoxy-2-(3-methyl-1-oxobutyl)amino-β-D-glucopyranoside (No. 19).

9. A pharmaceutical composition comprising a compound according to claim 1, or a pharmaceutically acceptable salt thereof, and at least one pharmaceutically acceptable excipient.

10. A compound of formula (VI):

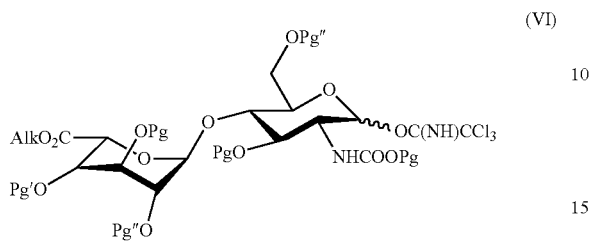

(VI)

in which Alk represents an alkyl group and Pg, Pg' and Pg", which may be identical or different, represent protecting groups.

11. A compound according to claim 10, in which Alk represents a methyl group and Pg, Pg' and Pg" represent, respectively, benzyl, levulinyl and acetyl groups.

* * * * *

UNITED STATES PATENT AND TRADEMARK OFFICE
CERTIFICATE OF CORRECTION

PATENT NO. : 9,012,413 B2  
APPLICATION NO. : 13/369675  
DATED : April 21, 2015  
INVENTOR(S) : Pierre Alexandre Driguez et al.

It is certified that error appears in the above-identified patent and that said Letters Patent is hereby corrected as shown below:

In the specification

In column 5, line 27, delete "pantyl" and insert -- pentyl --, therefor.

In column 14, line 33-34, delete "acetone-yclohexane" and insert -- acetone-cyclohexane --, therefor.

In column 46, line 47, delete "(1×4)" and insert -- (1→4) --, therefor.

In column 61, line 48, delete "1/00/1" and insert -- 1/0→0/1 --, therefor.

In column 62, line 17, delete "1/00/1" and insert -- 1/0→0/1 --, therefor.

In column 67, line 28, delete "(100/082/18" and insert -- (100/0→82/18 --, therefor.

In column 103, line 43, delete "3-D-glucopyranoside" and insert -- β-D-glucopyranoside --, therefor.

In column 103, line 61, delete "3-D-glucopyranoside" and insert -- β-D-glucopyranoside --, therefor.

In column 104, line 33, delete "3-D-glucopyranoside" and insert -- β-D-glucopyranoside --, therefor.

In column 104, line 47, delete "3-D-glucopyranoside" and insert -- β-D-glucopyranoside --, therefor.

In column 104, line 61, delete "3-D-glucopyranoside" and insert -- β-D-glucopyranoside --, therefor.

In column 105, line 4, delete "3-D-glucopyranoside" and insert -- β-D-glucopyranoside --, therefor.

In column 111, line 51, delete "δ-D-glucopyranoside" and insert -- β-D-glucopyranoside --, therefor.

In column 112, line 57, delete "δ-D-glucopyranoside" and insert -- β-D-glucopyranoside --, therefor.

In column 132, line 15, delete "αβ-glucopyranosyl" and insert -- α-D-glucopyranosyl --, therefor.

In the claims

In column 168, line 18, in claim 8, delete "8-D-glucopyranoside" and insert -- β-D-glucopyranoside --, therefor.

In column 168, line 60, in claim 8, delete "idopyranosyl uronate" and insert -- idopyranosyluronate --, therefor.

Signed and Sealed this  
Twenty-second Day of December, 2015

Michelle K. Lee  
*Director of the United States Patent and Trademark Office*